US006756384B2

(12) United States Patent
Andersen et al.

(10) Patent No.: US 6,756,384 B2
(45) Date of Patent: Jun. 29, 2004

(54) IMIDAZOLE COMPOUNDS

(75) Inventors: Knud Erik Andersen, Brondby (DK); Florencio Zaragoza Dorwald, Ballerup (DK); Bernd Peschke, Malov (DK); Ulla Grove Sidelmann, Vedbæk (DK); Klaus Rudolf, Warthausen (DE); Dirk Stenkamp, Biberach (DE); Rudolf Hurnaus, Biberach (DE); Stephan Georg Muller, Warthausen (DE); Bernd Krist, Ulm (DE); Birgitte Eriksen, Farum (DK)

(73) Assignees: Novo Nordisk A/S, Bagsvaerd (DK); Boehringer Ingelheim International GmbH, Ingelheim am Rhein (DE)

( * ) Notice: Subject to any disclaimer, the term of this patent is extended or adjusted under 35 U.S.C. 154(b) by 66 days.

(21) Appl. No.: 10/201,865

(22) Filed: Jul. 23, 2002

(65) Prior Publication Data

US 2003/0135056 A1 Jul. 17, 2003

Related U.S. Application Data

(63) Continuation of application No. 09/810,237, filed on Mar. 16, 2001, now Pat. No. 6,437,147.
(60) Provisional application No. 60/216,553, filed on Jul. 7, 2000, and provisional application No. 60/193,741, filed on Mar. 31, 2000.

(30) Foreign Application Priority Data

Mar. 17, 2000 (DK) .......................... 2000 00441
Jun. 29, 2000 (DK) .......................... 2000 01016

(51) Int. Cl.$^7$ ...................... A61K 31/44; C07D 453/02
(52) U.S. Cl. ...................... 514/305; 514/341; 514/387; 546/135; 546/302.7; 548/304.1
(58) Field of Search ...................... 514/305, 341, 514/387; 546/135; 548/302.7, 304.1

(56) References Cited

U.S. PATENT DOCUMENTS

| | | | |
|---|---|---|---|
| 3,920,678 A | 11/1975 | Butula | 260/309 |
| 4,767,778 A | 8/1988 | Arrang et al. | 514/397 |
| 5,578,616 A | 11/1996 | Aslanian et al. | 514/341 |
| 6,437,147 B1 * | 8/2002 | Andersen et al. | 548/304.1 |

FOREIGN PATENT DOCUMENTS

| | | |
|---|---|---|
| DE | 1948795 | 4/1971 |
| EP | 0 197 840 B1 | 10/1986 |
| EP | 0 214 058 A2 | 3/1987 |
| EP | 0 338 939 A1 | 10/1989 |
| EP | 0 376 624 A1 | 7/1990 |
| EP | 0 381 422 A1 | 8/1990 |
| EP | 0 458 661 A1 | 11/1991 |
| EP | 0 494 010 A1 | 7/1992 |
| EP | 0 531 219 A1 | 3/1993 |
| EP | 0 721 949 A1 | 7/1996 |
| WO | WO 91/17146 | 11/1991 |
| WO | WO 92/04343 | 3/1992 |
| WO | WO 92/15567 | 9/1992 |
| WO | WO 93/12093 | 6/1993 |
| WO | WO 93/12107 | 6/1993 |
| WO | WO 93/12108 | 6/1993 |
| WO | WO 93/14070 | 7/1993 |
| WO | WO 93/20061 | 10/1993 |
| WO | WO 94/17058 | 8/1994 |
| WO | WO 95/06037 | 3/1995 |
| WO | WO 95/09167 | 4/1995 |
| WO | WO 95/11894 | 5/1995 |
| WO | WO 95/14007 | 5/1995 |
| WO | WO 95/32965 | 12/1995 |
| WO | WO 96/25396 | 8/1996 |
| WO | WO 96/38141 | 12/1996 |
| WO | WO 96/38142 | 12/1996 |
| WO | WO 96/40126 | 12/1996 |

OTHER PUBLICATIONS

Japanese Patent Application No. 08–325234.
Japanese Patent Application No. 06–157518.
Japanese Patent Application No. 08–269050.
Japanese Patent Application 4–9372.
Japanese Patent Application No. 4–13666.
Ohta et al., Chem. Pharm. Bull, vol. 44, pp. 1000–1008 (1996).
Stark et al., Drugs of the Future, vol. 21, pp. 507–520 (1996).
Leurs et al., Progress in Drug Research, vol. 45, pp. 107–165 (1995).
Lovenberg et al., Molecular Pharmacology, vol. 55, pp. 1101–1107 (1999).
Morisset et al., Nature, vol. 408, pp. 860–864 (2000).
Ohta et al., Chem. Pharm. Bull, vol. 44, pp. 1707–1716 (1996).
Ohta et al., Chem. Pharm. Bull., vol. 44, pp. 991–999 (1996).
Utaka et al., Journal of the American Chemical Society, vol. 98, pp. 984–990 (1976).
I. Butula et al., Croatica Chemica Acta, vol. 45, pp. 297–312 (1973).
Abstract of Japanese Patent Application No. 04–009372.
Japanese Patent Application No. 8–325234.

* cited by examiner

Primary Examiner—Alan L. Rotman
Assistant Examiner—Kamal A Saeed
(74) Attorney, Agent, or Firm—Rosemarie R. Wilk-Orescan; Reza Green

(57) ABSTRACT

A novel class of imidazo heterocyclic compounds, pharmaceutical compositions comprising them and use thereof in the treatment and/or prevention of diseases and disorders related to the histamine H3 receptor. More particularly, the compounds are useful for the treatment and/or prevention of diseases and disorders in which an interaction with the histamine H3 receptor is beneficial.

13 Claims, No Drawings

IMIDAZOLE COMPOUNDS

CROSS-REFERENCE TO RELATED APPLICATIONS

This application is a continuation of U.S. application Ser. No. 09/810,237 filed Mar. 16, 2001, now U.S. Pat. No. 6,437,147, and claims priority under 35 U.S.C. 119 of U.S. provisional application No. 60/193,741 filed on Mar. 31, 2000; U.S. provisional application No. 60/216,553 filed on Jul. 7, 2000, Danish application no. PA 2000 00441 filed on Mar. 17, 2000 and Danish application No. PA 2000 01016 filed on Jun. 29, 2000, the contents of which are fully incorporated herein by reference.

FIELD OF THE INVENTION

The present invention relates to novel imidazo heterocyclic compounds, to the use of these compounds as pharmaceutical compositions, to pharmaceutical compositions comprising the compounds, and to a method of treatment employing these compounds and compositions. The present compounds show a high and selective binding affinity to the histamine H3 receptor indicating histamine H3 receptor antagonistic, inverse agnostic or agnostic activity. As a result, the compounds are useful for the treatment and/or prevention of diseases and disorders related to the histamine H3 receptor.

BACKGROUND OF THE INVENTION

The existence of the histamine H3 receptor has been known for several years and the receptor is of current interest for the development of new medicaments (see eg Stark, H.; Schäcker, E.; Schunack, W., *Drugs Fut.* 1996, 21, 507–520; Leurs, R.; Timmeman, H.; Vollinga, R. C., *Progress in Drug Research* 1995, 45, 107–165). Recently, the human histamine H3 receptor has been cloned, cf Lovenberg, T. W. et al, *Molecular Pharmacology*, June 1995, 55, 1101–1107. The histamine H3 receptor is a presynaptic autoreceptor located both in the central and the peripheral nervous system, the skin and in organs such as the lung, the intestine, probably the spleen and the gastrointestinal tract. Recent evidence suggests that the H3 receptor show intrinsic, constitutive activity, in vitro as well as in vivo (ie it is active in the absence of an agonist; see eg Morisset et al., *Nature* 2000, 408, 860–864). This activity can be inhibited by compounds acting as inverse agonists. The histamine H3 receptor has been demonstrated to regulate the release of histamine and also of other neurotransmitters such as serotonin and acetylcholine. A histamine H3 receptor antagonist or inverse agonist would therefore be expected to increase the release of these neurotransmitters in the brain. A histamine H3 receptor agonist, on the contrary, leads to an inhibition of the biosynthesis of histamine and an inhibition of the release of histamine and also of other neurotransmitters such as serotonin and acetylcholine. These findings suggest that histamine H3 receptor agonists, inverse agonists and antagonists could be important mediators of neuronal activity. Accordingly, the histamine H3 receptor is an important target for new therapeutics.

Several publications disclose the preparation and use of histamine H3 agonists and antagonists see eg U.S. Pat. No. 4,767,778 (corresponding to EP 214 058), EP 338 939, WO 93/14070, EP 531 219, E 458 661, EP 197 840, EP 494 010, WO 91/17146, WO 93/12108, WO 93/12107, WO 93/12093, U.S. Pat. No. 5,578,616 (corresponding to WO 95/14007), WO 96/38142, WO 96/38141, WO 95/11894, WO 93/20061, WO 96/40126, WO 95/06037, WO 92/15567 and WO 94/17058. These imidazole derivatives differ structurally from the present compounds.

Furthermore, several publications, ia JP 08269050, WO 96/25396, Chem. Pharm. Bull. 1996, 44(9), 1707–1716, Chem. Pharm. Bull. 1996, 44(5), 1000–1008, Pharm. Bull. 1996, 44(5), 991–999, WO 95/32965, WO 95/09167, JP 06157518, WO 92/04343, JP 04009372, EP 381 422, EP 376 624, Croat. Chem. Acta 1973, 45(2), 297–312, DE 1948795, U.S. Pat. No. 3,920,678, JP 08325234, J. Am. Chem. Soc. 1976, 98(4), 984–90 and JP 04013666, disclose imidazole derivatives. Some of these are stated to be useful for therapeutic purposes. However, they are not disclosed as histamine H3 receptor agonists, inverse agonists or antagonists.

In view of the art's interest in histamine H3 receptor agonists, inverse agonists and antagonists, novel compounds which interact with the histamine H3 receptor would be a highly desirable contribution to the art. The present invention provides such a contribution to the art being based on the finding that a novel class of imidazo heterocyclic compounds has a high and specific affinity to the histamine H3 receptor.

Due to their interaction with the histamine H3 receptor, the present compounds are useful in the treatment and/or prevention of a wide range of conditions and disorders in which an interaction wit the histamine H3 receptor is beneficial. Thus, the compounds may find use eg in the treatment of diseases of the central nervous system, the peripheral nervous system, the cardiovascular system, the pulmonary system, the gastrointestinal system and the endocrinological system.

DEFINITIONS

The following is a detailed definition of the terms used to describe the compounds of the invention.

"Halogen" designates an atom selected from the group consisting of F, Cl, Br and I.

The term "$C_{1-8}$-alkyl" in the present context designates a saturated, branched or straight hydrocarbon group having from 1 to 6 carbon atoms. Representative examples include, but are not limited to, methyl, ethyl, n-propyl, isopropyl, butyl, isobutyl, sec-butyl, tert-butyl, n-pentyl, isopentyl, neopentyl, tert-pentyl, n-hexyl, isohexyl and the like.

The term "$C_{2-6}$-alkenyl" as used herein represents a branched or straight hydrocarbon group having from 2 to 6 carbon atoms and at least one double bond. Examples of such groups includes, but are not limited to, vinyl, 1-propenyl, 2-propenyl, isopropenyl, 1,3-butadienyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 2-hexenyl, 3-hexenyl, 2,4-hexadienyl, 5-hexenyl and the like.

The term "$C_{2-8}$-alkynyl" as used herein represents a branched or straight hydrocarbon group having from 2 to 6 carbon atoms and at least one triple bond. Examples of such groups include, but are not limited to, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 5-hexynyl, 2,4-hexadiynyl and the like.

The term "$C_{1-6}$-alkoxy" in the present context designates a group —O—$C_{1-6}$-alkyl wherein $C_{1-8}$-alkyl is as defined above. Representative examples include, but are not limited to, methoxy, ethoxy, n-propoxy, isopropoxy, butoxy, isobutoxy, sec-butoxy, tert-butoxy, n-pentoxy, isopentoxy, neopentoxy, tert-pentoxy, n-hexoxy, isohexoxy and the like.

The term "$C_{1-8}$-alkylthio" in the present context designates a group —S—$C_{1-6}$-alkyl wherein $C_{1-8}$-alkyl is as defined above. Representative examples include, but are not limited to, methylthio, ethylthio, n-propylthio, isopropylthio, butylthio, isobutylthio, sec-butylthio, tert-butylthio, n-pentylthio, isopentylthio, neopentylthio, tert-pentylthio, n-hexylthio, isohexylthio and the like.

The term "$C_{1-8}$-alkylcarbonyl" in the present context designates a group —C(=O)-$C_{1-8}$-alkyl wherein $C_{1-6}$-alkyl is as defined above. Representative examples include, but are not limited to, methylcarbonyl, ethylcarbonyl, n-propylcarbonyl, isopropylcarbonyl, butylcarbonyl, isobutylcarbonyl, sec-butylcarbonyl, tert-butylcarbonyl, n-pentylcarbonyl, isopentylcarbonyl, neopentylcarbonyl, tert-pentylcarbonyl, n-hexylcarbonyl, isohexylcarbonyl and the like.

The term "$C_{1-6}$-alkylsulfonyl" in the present context designates a group —S(=O)$_2$—$C_{1-6}$-alkyl wherein $C_{1-6}$-alkyl is as defined above. Representative examples include, but are not limited to, methylsulfonyl, ethylsulfonyl, n-propylsulfonyl, isopropylsulfonyl, butylsulfonyl, isobutylsulfonyl, sec-butylsulfonyl, tert-butylsulfonyl, n-pentylsulfonyl, isopentylsulfonyl, neopentylsulfonyl, tert-pentylsulfonyl, n-hexylsulfonyl, isohexylsulfonyl and the like.

The term "$C_{3-10}$-cycloalkyl" as used herein represents a saturated mono-, bi-, tri- or spirocarbocyclic group having from 3 to 10 carbon atoms. Representative examples are cyclopropyl, cyclobutyl, cyclopentyl, cyclohexyl, cycloheptyl, cyclooctyl, cyclononyl, cyclodecyl, bicyclo[3.2.1]octyl, spiro[4.5]decyl, norpinyl, norbonyl, norcarbyl, adamantyl and the like.

The term "$C_{3-10}$-cycloalkylcarbonyl" as used herein represents a group —C(=O)—$C_{3-10}$-cycloalkyl wherein $C_{3-10}$-cycloalkyl is as defined above.

The term "$C_{3-8}$-heterocyclyl" as used herein represents a saturated 3 to 8 membered ring containing one or more heteroatoms selected from nitrogen, oxygen and sulfur. Representative examples are pyrrolidyl, piperidyl, piperazinyl, morpholinyl, thiomorpholinyl, aziridinyl, THFyl and the like.

The term "aryl" as used herein represents a carbocyclic aromatic ring system such as phenyl, biphenyl, naphthyl, anthracenyl, phenanthrenyl, fluorenyl, indenyl, pentalenyl, azuienyl, biphenylenyl and the like. Aryl is also intended to include the partially hydrogenated derivatives of the carbocyclic aromatic systems enumerated above. Non-limiting examples of such partially hydrogenated derivatives are 1,2,3,4-tetrahydronaphthyl, 1,4-dihydronaphthyl and the like.

The term "aroyl" as used herein represents a group —C(=O)-aryl wherein aryl is as defined above.

The term "arylthio" as used herein represents a group —S-aryl wherein aryl is as defined above.

The term "aryloxy" as used herein represents a group —O-aryl wherein aryl is as defined above.

The term "arylsulfonyl" as used herein represents a group —S(=O)$_2$-aryl wherein aryl is as defined above.

The term "arylamino" as used herein represents a group —NH-aryl wherein aryl is as defined above.

The term "aryl annulated with $C_{3-8}$-heterocyclyl" as used herein represents a ring system which contains an aryl group as defined herein to which a $C_{3-8}$-heterocyclyl group as defined herein is attached and which does not fall under the below definition of heteroaryl. The aryl group and the heterocyclyl group may form fused, bridged or spirocyclic ring systems. Representative examples are 2,3-methylenedioxyphenyl, 3,4-methylenedioxyphenyl, 2,4-methylenedioxyphenyl, 2,5-methylenedioxyphenyl, 3,5-methylenedioxyphenyl, 3,6-methylenedioxyphenyl, chromanyl, isochromanyl, 2,3-ethylenedioxyphenyl, 3,4-ethylenedioxyphenyl, 2,4-ethylenedioxyphenyl, 2,5-ethylenedioxyphenyl, 3,5-ethylenedioxyphenyl, 3,6-ethylenedioxyphenyl and the like.

The term "heteroaryl" as used herein represents a heterocyclic aromatic ring system containing one or more heteroatoms selected from nitrogen, oxygen and sulfur such as furanyl, thiophenyl, pyrrolyl, oxazolyl, thiazolyl, imidazolyl, isoxazolyl, isothiazolyl, 1,2,3-triazolyl, 1,2,4-triazolyl, pyranyl, pyridyl, pyridazinyl, pyrimidinyl, pyrazinyl, 1,2,3-triazinyl, 1,2,4-triazinyl, 1,3,5-triazinyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, thiadiazinyl, indolyl, isoindolyl, benzofuranyl, benzothiophenyl (thianaphthenyl), indazolyl, benzimidazolyl, benzthiazolyl, benzisothiazolyl, benzoxazolyl, benzisoxazolyl, purinyl, quinazolinyl, quinolizinyl, isoquinolinyl, quinoxalinyl, naphthylridinyl, pteridinyl, carbazolyl, azepinyl, diazepinyl, acridinyl and the like. Heteroaryl is also intended to include the partially hydrogenated derivatives of the heterocyclic systems enumerated above. Non-limiting examples of such partially hydrogenated derivatives are 2,3-dihydrobenzofuranyl, pyrrolinyl, pyrazolinyl, indolinyl, oxazolidinyl, oxazolinyl, oxazepinyl and the like.

The term "heteroaryl" as used herein represents a group —C(=O)-heteroaryl wherein heteroaryl is as defined above.

The term "heteroarylthio" as used herein represents a group —S-heteroaryl wherein heteroaryl is as defined above.

The term "heteroaryloxy" as used herein represents a group —O-heteroaryl wherein heteroaryl is as defined above.

The term "heteroarylsulfonyl" as used herein represents a group —S(=O)$_2$-heteroaryl wherein heteroaryl is as defined above.

The term "heteroarylamino" as used herein represents a group —NH-heteroaryl wherein heteroaryl is as defined above.

"Aryl-$C_{1-6}$-alkyl", "heteroaryl-$C_{1-6}$-alkyl" etc. means $C_{1-6}$-alkyl as defined above, substituted by an aryl or heteroaryl as defined above, for example.

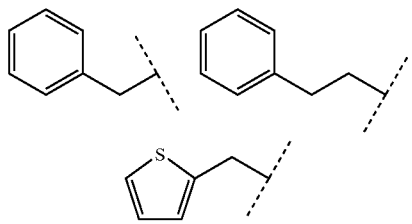

In connection with the terms "—C(=NOR$^7$)$C_{1-6}$-alkyl", "—C(=NOR$^7$)$C_{3-10}$-cycloalkyl", "—C(=NOR$^7$)aryl" and "—C(=NOR$^7$)heteroaryl" as used herein it should be understood that the substituents are attached via the carbon atom, for example as follows:

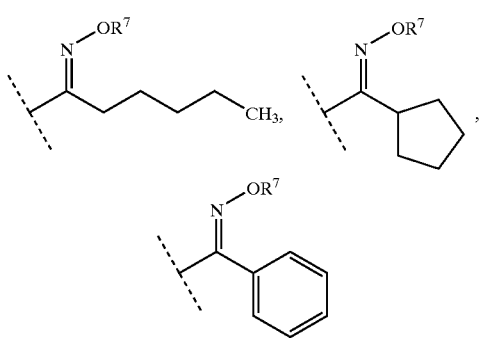

Certain of the above defined terms may occur more than once in the structural formulae, and upon such occurrence each term shall be defined independently of the other.

The term "optionally substituted" as used herein means that the groups in question are either unsubstituted or substituted with one or more of the substituents specified. When the groups in question are substituted with more than one substituent the substitutes may be the same or different.

As used herein, the phrase "a functional group which can be converted to hydrogen in vivo" is intended to include any group which upon administering the present compounds to the subjects in need thereof can be converted to hydrogen eg enzymatically or by the acidic environment in the stomach. Non-limiting examples of such groups are acyl, carbamoyl, monoalkylated carbamoyl, dialkylated carbamoyl, alkoxycarbonyl, alkoxyalkyl groups and the like such as $C_{1-6}$-alkylcarbonyl, aroyl, $C_{1-6}$-alkylcarbamoyl, di-$C_{1-6}$-alkylcarbamoyl, $C_{1-6}$-alkoxycarbonyl and $C_{1-8}$-alkoxy-$C_{1-8}$-alkyl.

As used herein, the phrase "diseases and disorders related to the histamine H3 receptor" is intended to include any disease or disorder in which an effect, either antagonistic or agnostic, on the histamine H3 receptor is beneficial.

DETAILED DESCRIPTION OF THE INVENTION

The present invention relates to compounds of the general formula (I):

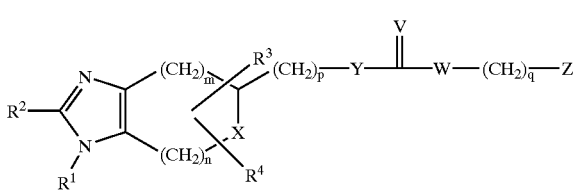

(I)

wherein
- $R^1$ is hydrogen or a functional group, which can be converted to hydrogen in vivo,
- $R^2$ is hydrogen, $C_{1-8}$-alkyl, $C_{1-8}$-alkoxy, $C_{1-6}$-alkylthio, halogen, cyano, trifluoromethyl, hydroxy, thiol or —$NR^5R^6$, wherein $R^5$ and $R^6$ independently are hydrogen or $C_{1-8}$-alkyl,
- $R^3$ and $R^4$ independently are hydrogen or $C_{1-8}$-alkyl, which is optionally substituted with aryl or heteroaryl, which are optionally substituted with one or more substituents selected from nitro, —$NR^7R^8$, —(=O)$_2$ $NR^7R^8$, —C(=O)$NR^7R^8$, hydroxy, halogen, cyano, trifluoromethyl, —$OCF_3$, —$OCHF_2$, —$OCH_2CHF_2$, $C_{1-6}$-alkyl, $C_{2-4}$-alkenyl, $C_{2-6}$-alkynyl, $C_{1-8}$-alkoxy, $C_{1-8}$-alkylthio, $C_{1-6}$-alkylsulfonyl, —C(=O)$OR^7$, $C_{1-6}$-alkylcarbonyl, —C(=$NOR^7$)$C_{1-8}$-alkyl, $C_{3-10}$-cycloalkyl, $C_{3-10}$-cycloalkylcarbonyl, —C(=$NOR^7$) $C_{3-10}$-cycloalkyl, aryl-$C_{1-6}$-alkyl, heteroaryl-$C_{1-6}$-alkyl, arylamino, heteroarylamino, aroyl, heteroaroyl, arylsulfonyl, heteroarylsulfonyl, —C(=$NOR^7$)aryl, —C(=$NOR^7$)heteroaryl, arylthio, heteroarylthio, aryloxy and heteroaryloxy, wherein $R^7$ and $R^8$ independently are hydrogen or $C_{1-6}$-alkyl, m is 0, 1 or 2, n is 1, 2, 3 or 4, X is a valence bond, —O—, —S—, —S(=O)—, —S(=O)$_2$— or —$CF_2$—, p is 0, 1, 2 or 3, Y is a valence bond, —O—, —S— or —$NR^9$—, wherein $R^9$ is hydrogen or $C_{1-6}$-alkyl, V is =O, =S or =$NR^{10}$, wherein $R^{10}$ is hydrogen, cyano, nitro or $C_{1-6}$-alkyl, W is a valence bond, —O—, —S— or —$NR^{11}$, wherein $R^{11}$ is hydrogen or $c_{1-6}$-alkyl, q is 0, 1, 2, or 3, Z is heteroaryl, aryl, aryloxy, $C_{3-10}$-cycloalkyl, $C_{3-8}$-heterocyclyl or aryl annulated with $C_{3-4}$-heterocyclyl, which are optionally substituted with one or more substituents selected from
- nitro, —$NR^{12}R^{13}$, —S(=O)$_2NR^{12}R^{13}$, —C(=O) $NR^{12}R^{13}$, hydroxy, halogen, cyano, trifluoromethyl, —$OCF_3$, —$OCHF_2$, —$OCH_2CHF_2$, $C_{1-6}$-alkyl, $C_{1-8}$-alkyl substituted with hydroxy, $C_{2-6}$-alkenyl, $C_{2-6}$-alkynyl, $C_{1-8}$-alkoxy, $C_{1-8}$-alkoxy substituted with hydroxy, $C_{1-6}$-alkylthio, $C_{1-8}$-alkylsulfonyl, —C(=O)$OR^{12}$, $C_{1-8}$-alkylcarbonyl, —C(=$NOR^{12}$) $C_{1-6}$-alkyl, $C_{3-10}$-cycloalkyl, $C_{3-10}$-cycloalkylcarbonyl, —C(=$NOR^{12}$)$C_{3-10}$-cycloalkyl, aryl-$C_{1-8}$-alkyl, heteroaryl-$C_{1-6}$-alkyl, arylamino, heteroarylamino, aroyl, heteroaroyl, arylsulfonyl, heteroarylsulfonyl, —C(=$NOR^{12}$) aryl, —C(=$NOR^{12}$)heteroaryl, arylthio, heteroarylthio and heteroaryloxy, wherein $R^{12}$ and $R^{13}$ independently are hydrogen or $C_{1-6}$-alkyl,
- aryl and aryloxy, which are optionally substituted with one or more substituents selected from $C_{1-8}$-alkoxy, $C_{1-6}$-alkoxy, halogen, —$OCF_3$ or —$CF_3$,
- $C_{1-6}$-alkyl, $C_{2-8}$-alkenyl or $C_{2-8}$-alkynyl, which are optionally substituted with one or more substituents selected from
- heteroaryl, aryl, aryloxy, aroyl, $C_{3-10}$-cycloalkyl, $C_{3-8}$-heterocyclyl and aryl annutated with $C_{3-8}$-heterocyclyl, which are optionally substituted with one or more substituents selected from
- nitro, —$NR^{12}R^{13}$, —S(=O)$_2NR^{12}R^{13}$, —C(=O) $NR^{12}R^{13}$, hydroxy, halogen, cyano, trifluoromethyl, —$OCF_3$, —$OCHF_2$, —$OCH_2CHF_2$, $C_{1-8}$-alkyl, $C_{1-8}$-alkyl substituted with hydroxy, $C_{2-6}$-alkenyl, $C_{2-8}$-alkynyl, $C_{1-8}$-alkoxy, $C_{1-8}$-alkoxy substituted with hydroxy, $C_{1-8}$-alkylthio, $C_{1-8}$-alkylsulfonyl, —C(=O) $OR^{12}$, $C_{1-8}$-alkylcarbonyl, —C(=$NOR^{12}$)$C_{1-8}$-alkyl, $C_{3-10}$-cycloalkyl, $C_{3-10}$-cycloalkylcarbonyl, —C(=$NOR^{12}$)$C_{3-10}$-cycloalkyl, aryl-$C_{1-8}$-alkyl, heteroaryl-$C_{1-8}$-alkyl arylamino, heteroarylamino, aroyl, heteroaroyl, arylsulfonyl, heteroarylsulfonyl, —C(=$NOR^{12}$)aryl, —C(=$NOR^{12}$)heteroaryl, arylthio, heteroarylthio and heteroaryloxy, wherein $R^{12}$ and $R^{13}$ independently are hydrogen or $C_{1-8}$-alkyl,
aryl and aryloxy, which are optionally substituted with one or more substituents selected from $C_{1-8}$-alkyl, $C_{1-8}$-alkoxy, halogen, —$OCF_3$ or —$CF_3$, with the provisos that when $R^3$ and $R^4$ are both hydrogen, m is 1, n is 2, p is 0, X is a valence bond, Y is a valence bond, V is =O, W is —$NR^{11}$—, q is 0, Z must not be unsubstituted or substituted aryl or unsubstituted or substituted heteroaryl, $R^3$ and $R^4$ are both hydrogen, m is 1, n is 2, p is 0, X is a valence bond, Y is a valence bond, V is =S, W is —NH—, q is 0, Z must not be unsubstituted or substituted aryl, $R^3$ and $R^4$ are both hydrogen, m is 1, n is 2, p is 0, X is a valence bond, Y is a valence bond, Vis =O, W is —O—, —$(CH_2)_q$-Z must not be unsubstituted methyl or ethyl, $R^3$ and $R^4$ are both hydrogen, m is 1, n is 2, p is 0, X is a valence bond, Y is a valence bond, V is =O, W is —$N(CH_3)$—, —$(CH_2)_q$Z must not be unsubstituted methyl, $R^3$ and $R^4$ are both hydrogen, m is 1, n is 2, p is 0, X is a valence bond, Y is a valence bond, V is =O, W is —NH—, —$(CH_2)_q$-Z must not be unsubstituted propyl, $R^3$ and $R^4$ are both hydrogen, m is 1, n is 2, p is 0, X is a valence bond, Y is a valence bond, V is =O, W is —$N(CH_2CH_3)$—, —$(CH_2)_q$-Z must not be unsubstituted ethyl, $R^3$ and $R^4$ are both hydrogen, m is 0, n is 3, p is 0, X is a valence bond, Y is a valence bond, V is =O, W is —O—, —$(CH_2)_q$-Z must not be unsubstituted methyl or ethyl, $R^3$ and $R^4$ are both hydrogen, m is 1, n is 2, p is 0, X is a valence bond, Y is —NH—, V is =O, W is a valence bond, q is 0, Z must not be 2-methoxy-4-amino-5-chlorophenyl, $R^3$ and $R^4$ are both hydrogen, m is 0, n is 3, p is 0 or 1, X is a valence bond, Y is —NH, V is =, W is a valence bond, q is 0, Z must not be unsubstituted or substituted aryl, $R^3$ and $R^4$ are both hydrogen, m is 0, n is 3, p is 1, X is a valence bond, Y is —O, V is =O, W is a valence bond, q is 0, Z must not be unsubstituted methyl, $R^3$ and $R^4$ are both hydrogen, m is 1, n is 2, p is 0, X is valence bond, Y is —NH, V is =O, W is —NH, q is 0, Z must not be unsubstituted or substituted aryl, $R^3$ and $R^4$ are both hydrogen, m is 1, n is 2, p is 0, X is a valence bond, Y is a valence bond, V is =O, W is a valence bond, q is 0, Z must not be unsubstituted or substituted morpholinyl, unsubstituted or substituted piperazinyl, unsubstituted or substituted indolyl, unsubstituted or substituted, 2,3-dihydroindolyl, unsubstituted or substituted indolizinyl, unsubstiuted or substituted benzoxazinyl, unsubstituted or substituted quinolinyl-1-yl, unsubstituted or substituted isoquinolinyl, unsubstituted or substituted benzo[b]thiophen-3-yl, unsubstituted or substituted benzofuran-3-yl, unsubstituted or substituted pyrrolidinyl, unsubstituted or substituted phenothiazinyl, unsubstituted or substituted thien-2-yl, or unsubstituted or substituted pyrrol-2-yl, as well as any optical or geometric isomer or tautomeric form thereof including mixtures of these or a pharmaceutically acceptable salt thereof.

In another aspect the present invention relates to compounds of the general formula (I")

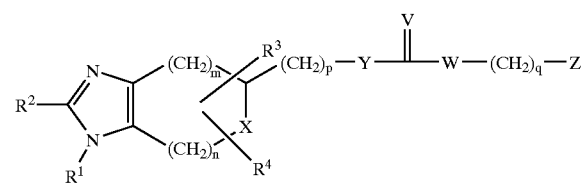

wherein $R^1$ is hydrogen or a functional group, which can be converted to hydrogen in vivo, $R^2$ is hydrogen, $C_{1-6}$-alkyl, $C_{1-6}$-alkoxy, $C_{1-6}$-alkylthio, halogen, cyano, trifluoromethyl, hydroxy, thiol or —$NR^5R^6$, wherein $R^5$ and $R^6$ independently are hydrogen or $C_{1-6}$-alkyl, $R^3$ and $R^4$ independently are hydrogen or $C_{1-6}$-alkyl, which is optionally substituted with aryl or heteroaryl, which are optionally substituted with one or more substituents selected from nitro, —$NR^7R^8$, —$S(=O)_2NR^7R^8$, —$C(=O)NR^7R^8$, hydroxy, halogen, cyano, trifluoromethyl, —$OCF_3$, —$OCHF_2$, —$OCH_2CHF_2$, $C_{1-6}$-alkyl, $C_{2-6}$-alkenyl, $C_{2-6}$-alkynyl, $C_{1-8}$-alkoxy, $C_{1-6}$-alkylthio, $C_{1-8}$-alkylsulfonyl, —(=O)$OR^7$, $C_{1-6}$-alkylcarbonyl, —$C(=NOR^7)C_{1-6}$-alkyl, $C_{3-10}$-cycloalkyl, $C_{3-10}$-cycloalkylcarbonyl, —$C(=NOR^7)C_{3-10}$-cycloalkyl, aryl-$C_{1-6}$-alkyl, heteroaryl-$C_{1-6}$-alkyl, arylamino, heteroarylamino, aroyl, heteroaroyl, arylsulfonyl, heteroarylsulfonyl, —$C(=NOR^7)$aryl, —$C(=NOR^7)$heteroaryl, arylthio, heteroarylthio, aryloxy and heteroaryloxy, wherein $R^7$ and $R^8$ independently are hydrogen or $C_{1-6}$-alkyl, m is 0, 1 or 2, n is 1, 2, 3 or 4, X is a valence bond, —O—, —S—, —$S(=O)$—, —$S(=O)_2$— or —$CF_2$—, p is 0, 1, 2 or 3, Y is a valence bond, —O—, —S— or —$NR^9$—, wherein $R^9$ is hydrogen or $C_{1-6}$-alkyl, V is =O, =S or =$NR^{10}$, wherein $R^{10}$ is hydrogen, cyano, nitro or $C_{1-8}$-alkyl, W is a valence bond, —O—, —S— or —$NR^{11}$—, wherein $R^{11}$ is hydrogen or $C_{1-6}$-alkyl, q is 0, 1, 2 or 3, Z is heteroaryl, aryl, $C_{3-10}$-cycloalkyl, $C_{3-8}$-heterocyclyl or aryl annulated with $C_{3-8}$-heterocyclyl,
which are optionally substituted with one or more substituents selected from
nitro, —$NR^{12}R^{13}$, —$S(=O)_2NR^{12}R^{13}$, —$C(=O)NR^{12}R^{13}$, hydroxy, halogen, cyano, trifluoromethyl, —$OCF_3$, —$OCHF_2$, —$OCH_2CHF_2$, $C_{1-6}$-alkyl, $C_{2-8}$-alkenyl, $C_{2-8}$-alkynyl, $C_{1-8}$-alkoxy, $C_{1-8}$-alkoxy substituted with hydroxy, $C_{1-6}$-alkylthio, $C_{1-6}$-alkylsulfonyl, —$C(=O)OR^{12}$, $C_{1-6}$-alkylcarbonyl, —$C(=NOR^{12})C_{1-6}$-alkyl, $C_{3-10}$-cycloalkyl, $C_{3-10}$-cycloalkylcarbonyl, arylamino, aroyl, heteroaroyl, arylsulfonyl, heteroarylsulfonyl, —$C(=NOR^{12})$aryl, —$C(=NOR^{12})$heteroaryl, arylthio, heteroarylthio, aryloxy and heteroaryloxy, wherein $R^{12}$ and $R^{13}$ independently are hydrogen or $C_{1-6}$-alkyl, aryl, which is optionally substituted with one or more substituents selected from $C_{1-6}$-alkyl, $C_{1-6}$-alkoxy, halogen or —$CF_3$, $C_{1-6}$-alkyl, $C_{2-8}$-alkenyl or $C_{2-6}$-alkynyl,
which are optionally substituted with one or more substituents selected from $C_{3-10}$-cycloalkyl, aryl, $C_{3-8}$-heterocyclyl and heteroaryl, which are optionally substituted with one or more substituents selected from nitro, —$NR^{14}R^{15}$, —$S(=O)_2 NR^{14}R^{15}$, —$(=O)NR^{14}R^{15}$, hydroxy, halogen, cyano, trifluoromethyl, —$OCF_3$, —$OCHF_2$, —$OCH_2CHF_2$, $C_{1-6}$-alkyl, $C_{2-6}$-alkenyl, $C_{2-6}$-alkynyl, $C_{1-8}$-alkoxy, $C_{1-8}$-alkylthio, $C_{1-6}$-alkylsulfonyl, —$C(=O)OR^{14}$, $C_{1-6}$-alkylcarbonyl, —$C(=NOR^{14})C_{1-6}$-alkyl, $C_{3-10}$-cycloalkyl, $C_{3-10}$-cycloalkylcarbonyl, —$C(=NOR^{14})C_{3-10}$-cycloalkyl, aryl-$C_{1-6}$-alkyl, heteroaryl-$C_{1-6}$-alkyl, arylamino, heteroarylamino, aroyl, heteroaroyl, arylsulfonyl, heteroarylsulfonyl, —$C(=NOR^{14})$aryl, —$C(=NOR^{14})$heteroaryl, arylthio, heteroarylthio, aryloxy and heteroaryloxy, wherein $R^{14}$ and $R^{15}$ independently are hydrogen or $C_{1-6}$-alkyl, with the provisos that when $R^3$ and $R^4$ are both hydrogen, m is 1, n is 2, p is 0, X is a valence bond, Y is a valence bond, V is =O, W is —$NR^{11}$, q is 0, Z must not be unsubstituted or substituted aryl or unsubstituted or substituted heteroaryl, $R^3$ and $R^4$ are both hydrogen, m is 1, n is 2, p is 0, X is a valence bond, Y is a valence bond, V is =S, W is —NH, q is 0, Z must not be unsubstituted or substituted aryl, $R^3$ and $R^4$ are both hydrogen, m is 1, n is 2, p is 0, X is a valence bond, Y is a valence bond, V is =O, W is —O—, —$(CH_2)_q$-Z must not be unsubstituted methyl or ethyl, $R^3$ and $R^4$ are both hydrogen, m is 1, n is 2, p is 0, X is a valence bond, Y is a valence bond, V is =O, W is —$N(CH_3)$—, q is 0, Z must not be unsubstituted methyl, $R^3$ and $R^4$ are both hydrogen, m is 1, n is 2, p is 0, X is a valence bond, Y is a valence bond, V is =O, W is —NH—, q is 0, Z must not be unsubstituted propyl, $R^3$ and $R^4$ are both hydrogen, m is 1, n is 2, p is 0, X is a valence bond, Y is a valence bond, V is =O, W is —$N(CH_2CH_3)$—, —$(CH_2)_q$-Z must not be unsubstituted ethyl, $R^3$ and $R^4$ are both hydrogen, m is 0, n is 3, p is 0, X is a valence bond, Y is a valence bond, V is =O, W is —O—, —$(CH_2)_q$-Z must not be unsubstituted methyl or ethyl, $R^3$ and $R^4$ are both hydrogen, m is 1, n is 2, p is 0, X is a valence bond, Y is —NH—, V is =O, W is a valence bond, q is 0, Z must not be unsubstituted or substituted aryl, $R^3$ and $R^4$ are both hydrogen, m is 0, n is 3, p is 0 or 1, X is a valence bond, Y is —NH—, V is =O, W is a valence bond, q is 0, Z must not be unsubstituted or substituted aryl, $R^3$ and $R^4$ are both hydrogen, m is 0, n is 3, p is 1, X is a valence bond, Y is —O—, V is =O, W is a valence bond, q is 0, Z must not be unsubstituted methyl, $R^3$ and $R^4$ are both hydrogen, m is 1, n is 2, p is 0, X is a valence bond, Y is —NH—, V is =O, W is —NH—, q is 0, Z must not be unsubstituted or substituted aryl, $R^3$ and $R^4$ are both hydrogen, m is 1, n is 2, p is 0, X is a valence bond, Y is a valence bond, V is =O, W is a valence bond, q is 0, Z must not be unsubstituted or substituted morpholinyl, unsubstituted or substituted piperazinyl, unsubstituted or substituted indolyl, unsubstituted or substituted 2,3-dihydroindolyl, unsubstituted or substituted indolizinyl, unsubstituted or substituted benzoxazinyl, unsubstituted or substituted quinolin-1-yl, unsubstituted or substituted isoquinolinyl, unsubstituted or substituted benzo[b]thiophen-3-yl, unsubstituted or substituted benzofuran-3-yl, unsubstituted or substituted pyrrolidinyl, unsubstituted or substituted phenothiazinyl, unsubstituted or substituted thien-2-yl, or unsubstituted or substituted pyrrol-2-yl, as well as any optical or geometric isomer or tautomeric form thereof including mixtures of these or a pharmaceutically acceptable salt thereof.

In yet another aspect the invention relates to a compound of the general formula (I'''):

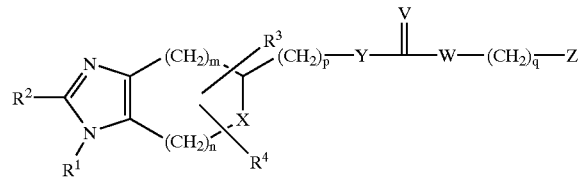

wherein $R^1$ is hydrogen or a functional group, which can be converted to hydrogen in vivo, $R^2$ is hydrogen, $C_{1-6}$-alkyl, $C_{1-6}$-alkoxy, $C_{1-8}$-alkylthio, halogen, cyano, trifluoromethyl, hydroxy, thiol or —$NR^5R^6$, wherein $R^5$ and $R^6$ independently are hydrogen or $C_{1-6}$-alkyl, $R^3$ and $R^4$ independently are hydrogen or $C_{1-6}$-alkyl, which is optionally substituted with aryl or heteroaryl, which are optionally substituted with one or more substituents selected from nitro, —$NR^7R^8$, —$S(=O)_2 R^7R^8$, —$C(=O)R^7R^8$, hydroxy, halogen, cyano, trifluoromethyl, —$OCF_3$, —$OCHF_2$, —$OCH_2CHF_2$, $C_{1-6}$-alkyl, $C_{2-8}$-alkenyl, $C_{2-6}$-alkynyl, $C_{1-6}$-alkoxy, $C_{1-8}$-alkylthio, $C_{1-6}$-alkylsulfonyl, —$C(=O)OR^7$, $C_{1-6}$-alkylcarbonyl, —$C(=NOR^7)C_{1-6}$-alkyl, $C_{3-10}$-cycloalkyl, $C_{3-10}$-cycloalkylcarbonyl, —$C(=NOR^7)C_{3-10}$-cycloalkyl, aryl-$C_{1-8}$-alkyl, heteroaryl-$C_{1-6}$-alkyl, arylamino, heteroarylamino, aroyl, heteroaroyl, arylsulfonyl, heteroarylsulfonyl, —$C(=NOR^7)$aryl, —$C(=NOR^7)$heteroaryl, arylthio, heteroarylthio, aryloxy and heteroaryloxy, wherein $R^7$ and $R^8$ independently are hydrogen or $C_{1-8}$-alkyl, m is 0, 1 or 2, n is 1, 2, 3 or 4, X is a valence bond, —O—, —S—, —$S(=O)$—, —$S(=O)_2$— or —$CF_2$—, p is 0, 1, 2 or 3, Y is a valence bond, —O—, —S— or —$NR^9$—, wherein $R^9$ is hydrogen or $C_{1-8}$-alkyl, V is =O, =S or =$NR^{10}$, wherein $R^{10}$ is hydrogen, cyano, nitro or $C_{1-6}$-alkyl, W is a valence bond, —O—, —S— or —$NR^{11}$, wherein $R^{11}$ is hydrogen or $C_{1-6}$-alkyl, with the proviso that Y and W are not simultaneously a valence bond, q is 0, 1, 2 or 3, Z is heteroaryl, aryl, $C_{3-10}$-cycloalkyl, $C_{3-8}$-heterocyclyl or aryl annulated with $C_{3-8}$-heterocyclyl, which are optionally substituted with one or more substituents selected from nitro, —$NR^{12}R^{13}$, —$S(=O)_2NR^{12}R^{13}$, —$C(=O)NR^{12}R^{13}$, hydroxy, halogen, cyano, trifluoromethyl, —$OCF_3$, —$OCHF_2$, —$OCH_2CHF_2$, $C_{1-8}$-alkyl, $C_{2-8}$-alkynyl, $C_{1-8}$-alkoxy, $C_{1-6}$-alkylthio, $C_{1-8}$-alkylsulfonyl, —$C(=O)OR^{12}$, $C_{1-6}$-alkylcarbonyl, —$C(=NOR^{12})C_{1-6}$-alkyl, $C_{3-10}$-cycloalkyl, $C_{3-10}$-cycloalkylcarbonyl, —$C(=NOR^{12})C_{3-10}$-cycloalkyl, aryl-$C_{1-6}$-alkyl, heteroaryl-$C_{1-6}$-alkyl, arylamino, heteroarylamino, aroyl, heteroaroyl, arylsulfonyl, heteroarylsulfonyl, —$C(=NOR^{12})$aryl, —$C(=NOR^{12})$heteroaryl, arylthio, heteroarylthio, aryloxy and heteroaryloxy, wherein $R^{12}$ and $R^{13}$ independently are hydrogen or $C_{1-8}$-alkyl, $C_{1-8}$-alkyl, $C_{2-8}$-alkenyl or $C_{2-8}$-alkynyl, which are optionally substituted with one or more substituents selected from $C_{3-10}$-cycloalkyl, aryl, $C_{3-8}$-heterocyclyl and heteroaryl, which are optionally substituted with one or more substituents selected from nitro, —$NR^{14}R^{15}$, —$S(=O)_2NR^{14}R^{15}$, —$C(=O)NR^{14}R^{15}$, hydroxy, halogen, cyano, trifluoromethyl, —$OCF_3$, —$OCHF_2$, —$OCH_2CHF_2$, $C_{1-8}$-alkyl, $C_{2-6}$-alkenyl, $C_{2-6}$-alkynyl, $C_{1-8}$-alkoxy, $C_{1-8}$-alkylthio, $C_{1-6}$-alkylsulfonyl, —$(=O)OR^{14}$, $C_{1-8}$-alkylcarbonyl, —$C(=NOR^{14})C_{1-6}$-alkyl, $C_{3-10}$-cycloalkyl, $C_{3-10}$-cycloalkylcarbonyl, —$C(=NOR^{14})C_{3-10}$-cycloalkyl, aryl-$C_{1-6}$-alkyl, heteroaryl-$C_{1-8}$-alkyl, arylamino, heteroarylamino, aroyl, heteroaroyl, arylsulfonyl, heteroarylsulfonyl, —$C(=NOR^{14})$aryl, —$(=NOR^{14})$heteroaryl, arylthio, heteroarylthio, aryloxy and heteroaryloxy, wherein $R^{14}$ and $R^{15}$ independently are hydrogen or $C_{1-6}$-alkyl, with the provisos that when $R^3$ and $R^4$ are both hydrogen, m is 1, n is 2, p is 0, X is a valence bond, Y is a valence bond, V is =O, W is —$NR^{11}$—, q is 0, Z must not be aryl or heteroaryl, $R^3$ and $R^4$ are both hydrogen, m is 1, n is 2, p is 0, X is a valence bond, Y is a valence bond, V is =S, W is —NH—, q is 0, Z must not be aryl, $R^3$ and $R^4$ are both hydrogen, m is 1, n is 2, p is 0, X is a valence bond, Y is a valence bond, V is =O, W is —O—, —$(CH_2)_q$—Z must be methyl or ethyl, $R^3$ and $R^4$ are both hydrogen, m is 1, n is 2, p is 0, X is a valence bond, Y is a valence bond, V is =O, W is —$N(CH_3)$—, q is 0, Z must not be methyl, $R^3$ and $R^4$ are both hydrogen, m is 1, n is 2, p is 0, X is a valence bond, Y is a valence bond, V is =O, W is —NH—, q is 0, Z must not be propyl, $R^3$ and $R^4$ are both hydrogen, m is 1, n is 2, p is 0, X is a valence bond, Y is a valence bond, V is =O, W is —$N(CH_2CH_3)$—, —$(CH_2)_q$-Z must not be ethyl, $R^3$ and $R^4$ are both hydrogen, m is 0, n is 3, p is 0, X is a valence bond, Y is a valence bond, V is =O, W is —O—, —$(CH_2)_q$-Z must not be methyl or ethyl, $R^3$ and $R^4$ are both hydrogen, m is 1, n is 2, p is 0, X is a valence bond, Y is —NH—, V is =O, W is a valence bond, q is 0, Z must not be aryl, $R^3$ and $R^4$ are both hydrogen, m is 0, n is 3, p is 0 or 1, X is a valence bond, Y is —NH—, V is =O, W is a valence bond, q is 0, Z must not be aryl, $R^3$ and $R^4$ are both hydrogen, m is 0, n is 3, p is 1, X is a valence bond, Y is —O—, V is =O, W is a valence bond, q is 0, Z must not be methyl, $R^3$ and $R^4$ are both hydrogen, m is 1, n is 2, p is 0, X is a valence bond, Y is —NH—, V is =O, W is —NH—, q is 0, Z must not be aryl, as well as any optical or geometric isomer or tautomeric form thereof including mixtures of these or a pharmaceutically acceptable salt thereof.

Preferably, $R^1$ is hydrogen.

Preferably, $R^2$ is also hydrogen.

Preferably, $R^3$ and $R^4$ are both hydrogen.

In a preferred embodiment m is 1 and n is 2.

In another preferred embodiment m is 0 and n is 3.

Preferably, X is a valence bond.

Preferably, p is 0 or 1.

In a preferred embodiment, Y is a valence bond or —O—.

Preferably, V is =O or =S.

In a preferred embodiment, W is —$NR^{11}$—, wherein $R^{11}$ is as defined for formula (I). $R^{11}$ is preferably hydrogen or methyl.

In another preferred embodiment W is a valence bond.

q is preferably 0, 1 or 2.

In a preferred embodiment Z is selected from $C_{1-8}$-alkyl, $C_{2-8}$-alkenyl, aryl, aryloxy, heteroaryl, $C_{3-10}$-cycloalkyl, $C_{3-8}$-heterocyclyl and aryl annulated with $C_{3-8}$-heterocyclyl, which are optionally substituted as defined for formula (I).

In another preferred embodiment Z is aryl, aryloxy, heteroaryl, $C_{3-10}$-cycloalkyl, $C_{3-8}$-heterocyclyl or aryl annulated with $C_{3-8}$-heterocyclyl, which is optionally substituted as defined for formula (I), or $C_{1-6}$-alkyl or $C_{2-6}$alkenyl, which is substituted with
aryl, aroyl, aryloxy, heteroaryl, $C_{3-10}$-cycloalkyl, $C_{3-8}$-heterocyclyl or aryl annutated with $C_{3-8}$-heterocyclyl, which is optionally substituted as defined for formula (I).

In still another preferred embodiment Z is aryl, aryloxy, heteroaryl, $C_{3-10}$-cycloalkyl, $C_{3-8}$-heterocyclyl or aryl annulated with $C_{3-8}$-heterocyclyl, which is optionally substituted as defined for formula (I), or $C_{1-6}$-alkyl or $C_{2-8}$-alkenyl, which is substituted with
aryl, aryloxy, aroyl, heteroaryl, $C_{3-10}$-cycloalkyl, $C_{3-8}$-heterocyclyl or aryl annutated with $C_{3-8}$-heterocyclyl, which is optionally substituted as defined for formula (I).

In yet another preferred embodiment thereof Z is phenyl, phenoxy, naphthyl, naphthyloxy, cyclopentyl, cyclohexyl, piperidyl, quinolinyl, pyridyl, thienyl, thiazolyl, 2,3-dihydrobenzofuranyl, benzofuranyl, benzo[1,3]dioxolyl, bicyclo[2.2.1]-heptyl, adamantyl, benzimidazol, benzotriazolyl or benzothiophenyl, which is optionally substituted as defined for formula (I), or $C_{1-6}$-alkyl or $C_{2-6}$-alkenyl, which is substituted with
phenyl, phenoxy, naphthyl, naphthyl, naphthyloxy, benzoyl, cyclopentyl, cyclohexyl, piperidyl, quinolinyl, pyridyl, thienyl, thiazolyl, 2,3-dihhydrobenzofuranyl, benzofuranyl, benzo[1,3]dioxolyl, bicyclo[2.2.1]heptyl, adamantyl, benzimidazol, benzotriazolyl or benzothiophenyl, which is optionally substituted as defined for formula (I).

In yet another preferred embodiment Z is phenyl, phenoxy, napthyl, naphthyloxy, cyclopentyl, cyclohexyl, piperidyl, pyridyl, thiazolyl, 2,3- dihydrobenzofuranyl, benzo[1,3]dioxolyl or bicyclo [2.2.1]heptyl, which is optionally substituted as defined for formula (I) or $C_{1-6}$-alkyl or $C_{2-6}$-alkenyl, which is substituted with phenyl, phenoxy, naphthyl, naphthyloxy, benzoyl, cyclopentyl, cyclohexyl, piperidyl, pyridyl, thiazolyl, 2,3-dihydrobenzofuranyl, benzo[1,3]dioxolyl or bicyclo[2.2.1]heptyl, which is optionally substituted as defined for formula (I).

In still a further preferred embodiment Z is phenyl, phenoxy, naphthyl or naphthyloxy, which is optionally substituted as defined for formula (I), or $C_{1-6}$-alkyl or $C_{2-8}$-alkenyl, which is substituted with
phenyl, phenoxy, naphthyl, benozyl or naphthyloxy, which is optionally substituted as defined for formula (I).

In yet a further preferred embodiment Z is phenyl, which is optionally substituted as defined form formula (I).

Z is preferably unsubstituted or substituted with one or two substituents selected from $C_{1-6}$-alkylsulfonyl, hydroxy, $C_{1-6}$-alkyl, $C_{1-6}$-alkoxy, halogen, —$OCF_3$, —$CF_3$, —$N(C_{1-6}alkyl)_2$, $C_{1-8}$-alkylthio, $C_{1-8}$-alkoxy substituted with hydroxy and $C_{1-8}$-alkyl substituted with hydroxy, phenyl and phenoxy, which are optionally substituted as defined for formula (I).

More preferably, Z is unsubstituted or substituted with one or two substituents selected from $C_{1-8}$-alkyl, $C_{1-8}$-alkoxy, —$CF_3$, —$OCF_3$, phenoxy and halogen.

In a preferred embodiment the invention relates to a compound of the general formula (Ih):

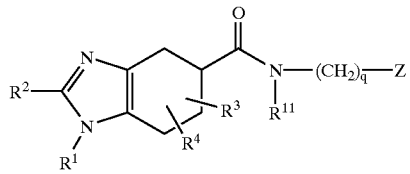

(Ih)

wherein q is 1, 2 or 3, Z, $R^1$, $R^2$, $R^3$, $R^4$ and $R^{11}$ are as defined for formula (I) or in any of the above preferred embodiments, or q is 0, Z is $C_{3-8}$-cycloalkyl or $C_{3-8}$-heterocyclyl, which is optionally substituted as defined defined for formula (I) or in any of the above preferred embodiments, and $R^1$, $R^2$, $R^3$, $R^4$ and $R^{11}$ are as defined for formula (I) or in any of the above preferred embodiments as well as any optical or geometric isomer or tautomeric form thereof including mixtures of these or a pharmaceutically acceptable salt thereof.

In another preferred embodiment the invention relates to a compound of the general formula (Ii):

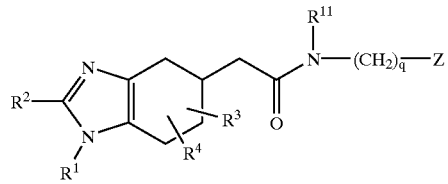

(Ii)

wherein $R^1$, $R^2$, $R^3$, $R^4$, $R^{11}$, q and Z are as defined for formula (I) or in any of the above preferred embodiments as well as any optical or geometric isomer or tautomeric form thereof including mixtures of these or a pharmaceutically acceptable salt thereof.

In still another preferred embodiment the invention relates to a compound of the general formula (Ij):

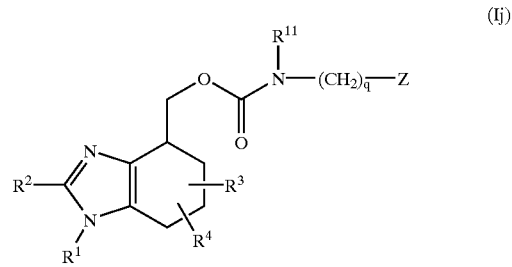

(Ij)

wherein $R^1$, $R^2$, $R^3$, $R^4$, $R^{11}$, q and Z are as defined for formula (I) or in any of the above preferred embodiments as well as any optical or geometric isomer or tautomeric form thereof including mixtures of these or a pharmaceutically acceptable salt thereof.

In yet another preferred embodiment the invention relates to a compound of the general formula (Ik):

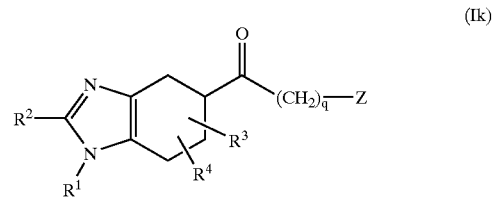

(Ik)

wherein q is 1, 2 or 3, and $R^1$, $R^2$, $R^3$, $R^4$ and Z are as defined for formula (I) or in any of the above preferred embodiments, or q is 0, Z is phenyl, phenoxy, naphthyl or naphthyloxy, which is optionally substituted as defined for formula (I) or in any of the above preferred embodiments as well as any optical or geometric isomer or tautomeric form thereof including mixtures of these or a pharmaceutically acceptable salt thereof.

In a further preferred embodiment the invention relates to a compound of the general formula (Im):

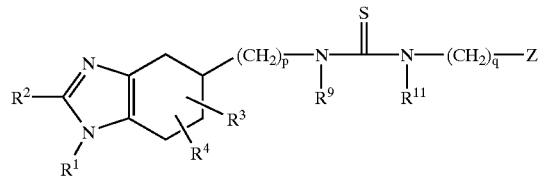

(Im)

wherein p is 0 or 1, $R^1$, $R^2$, $R^3$, $R^4$, q, $R^9$, $R^{11}$ and Z are as defined for formula (I) or in any of the above preferred embodiments as well as any optical or geometric isomer or tautomeric form thereof including mixtures of these or a pharmaceutically acceptable salt thereof.

In still a further preferred embodiment the invention relates to a compound of the general formula (In):

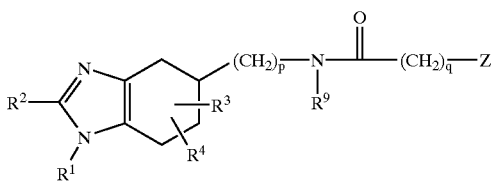

(In)

wherein p is 0, 1 or 2, $R^1$, $R^2$, $R^3$, $R^4$, q, $R^9$ and Z are as defined for formula (I) or in any of the above preferred embodiments with the proviso that when p is 0, $R^9$ is hydrogen and q is 0, Z must not be 2-methoxy-4-amino-5-chlorophenyl, as well as any optical or geometric isomer or tautomeric form thereof including mixtures of these or a pharmaceutically acceptable salt thereof.

In yet a further preferred embodiment the invention relates to a compound of the general formula (Io):

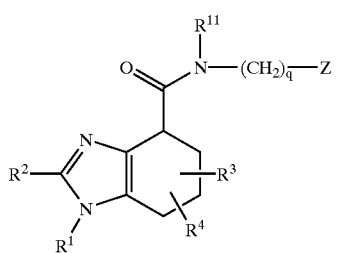

(Io)

wherein $R^1$, $R^2$, $R^3$, $R^4$, q, $R^{11}$ and Z are as defined for formula (I) or in any of the above preferred embodiments.

as well as any optical or geometric isomer or tautomeric form thereof including mixtures of these or a pharmaceutically acceptable salt thereof.

In still another preferred embodiment the invention relates to a compound of the general formula (Ip):

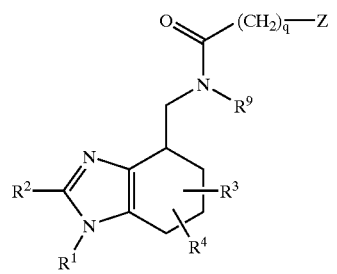

(Ip)

wherein $R^1$, $R^2$, $R^3$, $R^4$, q, $R^9$ and Z are as defined for formula (I) or in any of the above preferred embodiments as well as any optical or geometric isomer or tautomeric form thereof including mixtures of these or a pharmaceutically acceptable salt thereof.

The following compounds are within the scope of the present invention:
4,5,6,7-tetrahydro-1H-benzimidazole-5-carboxylic acid ((1S)-(naphth-1-yl)ethyl)amide,
4,5,6,7-tetrahydro-1H-benzimidazole-5-carboxylic acid ((1R)-(naphth-1-yl)ethyl)amide,
4,5,6,7-tetrahydro-1H-benzimidazole-5-carboxylic acid (naphth-1-ylmethyl)amide,
4,5,6,7-tetrahydro-1H-benzimidazole-5-carboxylic acid (cyclohexylmethyl)amide,
4,5,6,7-tetrahydro-1H-benzimidazole-5-carboxylic acid (2-chlorobenzyl)amide,
4,5,6,7-tetrahydro-1H-benzimidazole-5-carboxylic acid (4-chlorobenzyl)amide,
4,5,6,7-tetrahydro-1H-benzimidazole-5-carboxylic acid (3,4-difluorobenzyl)amide,
4,5,6,7-tetrahydro-1H-benzimidazole-5-carboxylic acid (3-methoxybenzyl)amide,
4,5,6,7-tetrahydro-1H-benzimidazole-5-carboxylic acid benzylamide,
4,5,6,7-tetrahydro-1H-benzimidazole-5-carboxylic acid 2-phenylethylamide,
4,5,6,7-tetrahydro-1H-benzimidazole-5-carboxylic acid N-(2-naphthylmethyl)-N-methylamide,
4,5,6,7-tetrahydro-1H-benzimidazole-5-carboxylic acid N-methyl-N-(2-(2-naphthyl)ethyl)amide,
4,5,6,7-tetrahydro-1H-benzimidazole-5-carboxylic acid N-methyl-N-((1-naphthyl)methyl)amide,
4,5,6,7-tetrahydro-1H-benzimidazole-5-carboxylic acid ((2,3-dihydrobenzofuran-7-yl)methyl)amide,
4,5,6,7-tetrahydro-1H-benzimidazole-5-carboxylic acid 4-trifluoromethoxybenzylamide,
4,5,6,7-tetrahydro-1H-benzimidazole-5-carboxylic acid 4-trifluoromethylbenzylamide,
4,5,6,7-tetrahydro-1H-benzimidazole-5-carboxylic acid (benzo[b]thiophen-5-ylmethyl)amide,
4,5,6,7-tetrahydro-1H-benzimidazole-5-carboxylic acid ((benzo[b]thiphen-2-yl)methyl)amide,
4,5,6,7-tetrahydro-1H-benzimidazole-5-carboxylic acid 3-trifluoromethyl-benzylamide,
piperidine-1-carboxylic acid 4,5,6,7-tetrahydro-1H-benzimidazol-4-ylmethyl ester,
N-cyclohexyl-N-methyl carbamic acid 4,5,6,7-tetrahydro-1H-benzimidazol-4-ylmethyl ester N-benzyl-N-methyl carbamic acid 4,5,6,7-tetrahydro-1H-benzimidazol-4-ylmethyl ester,
N-benzylcarbamic acid 4,5,6,7-tetrahydro-1H-benzimidazol-4-ylmethyl ester,
4,5,6,7-tetrahydro-1H-benzimidazole-5-carboxylic acid bicyclo[2.2.1]hept-2-ylamide,
4,5,6,7-tetrahydro-1H-benzimidazole-5-carboxylic acid N-methyl-N-(4-(trifluoromethyl)benzyl)amide,
4,5,6,7-tetrahydro-1H-benzimidazole-5-carboxylic acid N-(2-chloro-6-phenoxy-benzyl)amide,
4,5,6,7-tetrahydro-1H-benzimidazole-5-carboxylic acid (4-trifluoromethylcyclohexylmethyl)amide,
4,5,6,7-tetrahydro-1H-benzimidazole-5-carboxylic acid 4-methanesulfonylbenzylamide,
4,5,6,7-tetrahydro-1H-benzimidazole-5-carboxylic acid N-methyl-N-((4'-trifluoromethyl)biphenyl-2-yl)methyl)amide,
4,5,6,7-tetrahydro-1H-benzimidazole-5-carboxylic acid (3-chloro-4-trifluoromethylbenzyl)amide,
isobutyl-(4,5,6,7-tetrahydrobenzimidazol-5-yl)methanone,
4-phenoxyphenyl-(4,5,6,7-tetrahydrobenzimidazol-5-yl)methanone,
phenyl-(4,5,6,7-tetrahydrobenzimidazol-5-yl)methanone,
benzyl-(4,5,6,7-tetradhydrobenzimidazol-5-yl)methanone,
(5-methyl-2-pyridyl)-(4,5,6,7-tetrahydrobenzimidazol-5-yl)methanone,
(cyclohexylmethyl)-(4,5,6,7-tetrahydrobenzimidazol-5-yl)methanone,
4-methoxy-(4,5,6,7-tetrahydrobenzimidazol-5-yl)methanone,
4-dimethylaminophenyl-(4,5,6,7-tetrahydrobenzimidazol-5-yl)methanone,
1-naphthyl-(4,5,6,7-tetrahydrobenzimidazol-5-yl)methanone, 2-naphthyl-(4,5,6,7-tetrahydrobenzimidazol-5-yl)
  methanone,
4-tert-butylphenyl-(4,5,6,7-tetrahydrobenzimidazol-5-yl)
  methanone,
cyclopentyl-(4,5,6,7-tetrahydrobenzimidazol-5-yl)
  methanone,
2-thiazolyl-(4,5,6,7-tetrahydrobenzimidazol-5-yl)
  methanone,
4-fluorophenyl-(4,5,6,7-tetrahydrobenzimidazol-5-yl)
  methanone,
(5-methyl-2-thienyl)-(4,5,6,7-tetrahydrobenzimidazol-5-yl)
  methanone,
(4-methyl-3-thienyl)-(4,5,6,7-tetrahydrobenzimidazol-5-yl)
  methanone,
(2-phenylethyl)-(4,5,6,7-tetrahydrobenzimidazol-5-yl)
  methanone,
4-chlorophenyl-(4,5,6,7-tetrahydrobenzimidazol-5-yl)
  methanone,
benzofuran-5-yl-(4,5,6,7-tetrahydrobenzimidazol-5-yl)
  methanone,
benzo[1,3]dioxol-5-yl-(4,5,6,7-tetrahydrobenzimidazol-5-yl)methanone,
(4-(1-hydroxyethyl)phenyl)-(4,5,6,7-tetrahydrobenzimidazol-5-yl)methanone,
quinolin-3-yl-(4,5,6,7-tetrahydro-benzimidazol-5-yl)
  methanone,
4-trifluoromethylphenyl-(4,5,6,7-tetrahydrobenzimidazol-5-yl)methanone,
4-methylphenyl-(4,5,6,7-tetrahydrobenzimidazol-5-yl)
  methanone,
4-ethylphenyl-(4,5,6,7-tetrahydrobenzimidazol-5yl)
  methanone,
4-ethoxyphenyl-(4,5,6,7-tetrahydrobenzimidazol-5-yl)
  methanone,
4-(methylsulfanyl)phenyl-(4,5,6,7-tetrahydrobenzimidazol-5-yl)methanone,
6-methoxynaphthalen-2-yl-(4,5,6,7-tetrahydrobenzimidazol-5-yl)methanone,
(5-chloro-3-methylbenzo[b]thiphen-2-yl)-(4,5,6,7-tetrahydrobenzimidazol-5-yl)methanone,
(4-(2-hydroxyethyloxy)phenyl)-(4,5,6,7-tetrahydrobenzimidazol-5-yl)methanone,
4,5,6,7-tetrahydro-1H-benzimidazole-5-carboxylic acid
  (2,2-diphenylethyl)amide,
4,5,6,7-tetrahydro-1H-benzimidazole-5-carboxylic acid [2-(3,4-dichlorophenyl)ethyl]amide,
4,5,6,7-tetrahydro-1H-benzimidazole-5-carboxylic acid [2-(4-chlorophenyl)ethyl]amide,
4,5,6,7-tetrahydro-1H-benzimidazole-5-carboxylic acid
  (thiophen-2-ylmethyl)amide,
4,5,6,7-tetrahydro-1H-benzimidazole-5-carboxylic acid
  (4-tert-butylcyclohexyl)amide,
4,5,5,7-tetrahydro-1H-benzimidazole-5-carboxylic acid
  3-fluorobenzylamide,
4,5,6,7-tetrahydro-1H-benzimidazole-5-carboxylic acid
  (3,3-diphenylpropyl)amide,
4,5,6,7-tetrahydro-1H-benzimidazole-5-carboxylic acid
  (3-phenylpropyl)amide,
4,5,6,7-tetrahydro-1H-benzimidazole-5-carboxylic acid
  2-fluoro-6-(4-methoxy-phenoxy)benzylamide,
  hydrochloride,
4,5,6,7-tetrahydro-1H-benzimidazole-5-carboxylic acid
  phenylamide
5-cyclohexylpentanoic acid (4,5,6,7-tetrahydro-1H-benzimidazol-5-yl)amide,
N-(4,5,6,7-Tetrahydro-1H-benzimidazol-5-yl)-2-(4-trifluoromethoxyphenyl)acetamide,
3-cyclohexyl-N-(4,5,6,7-tetrahydro-1H-benzimidazol-5-yl)
  propionamide,
2-(4-chlorophenyl)-N-(4,5,6,7-tetrahydro-1H-benzimidazol-5-yl)acetamide,
N-(4,5,6,7-tetrahydro-1H-benzimidazol-5-yl)-4-trifluoromethoxybenzamide,
N-(4,5,6,7-tetrahydro-1H-benzimidazol-5-yl)-3-(4-trifluoromethoxyphenyl)acrylamide,
2-naphth-1-yl-N-(4,5,6,7-tetrahydro-1H-benzimidazol-5-yl)
  acetamide,
3-(4-chlorophenyl)-N-(4,5,6,7-tetrahydro-1H-benzimidazol-5-yl)acrylamide,
2-phenoxy-N-(4,5,6,7-tetrahydro-1H-benzimidazol-5-yl)
  benzamide,
3-(4-chlorophenyl)-N-(4,5,6,7-tetrahydro-1H-benzimidazol-5-yl)propionamide,
2-cyclohexyl-N-(4,5,6,7-tetrahydro-1H-benzimidazol-5-yl)
  acetamide,
4-(4-chlorophenyl)-N-(4,5,6,7-tetrahydro-1H-benzimidazol-5-yl)butyramide,
4-chloro-N-(4,5,6,7-tetrahydro-1H-benzimidazol-5-yl)
  benzamide hydrochloride,
5-phenylpentanoic acid (4,5,6,7-tetrahydro-1H-benzimidazol-5-yl)amide,
2-adamantan-1-yl-N-(4,5,6,7-tetrahydro-1H-benzimidazol-5-yl)acetamide,
2-bicyclo[2.2.1]hept-2-yl-N-(4,5,6,7-tetrahydro-1H-benzimidazol-5-yl)acetamide,
2-chloro-6-phenoxy-N-(4,5,6,7-tetrahydro-1H-benzimidazol-5-yl)benzamide,
1-phenyl-3-(4,5,6,7-tetrahydro-1H-benzimidazol-5-yl)
  thiourea,
1-cyclohexyl-3-(4,5,6,7-tetrahydro-1H-benzimidazol-5-yl)
  thiourea,
N-[2-(4-chlorophenyl)ethyl]-2-(4,5,6,7-tetrahydro-1H-benzimidazol-5-yl)acetamide,
N-[2-(4,5,6,7-tetrahydro-1H-benzimidazol-5-yl)-ethyl]-2-(4-trifluoromethoxyphenyl)acetamide,
naphthalene-1-carboxylic acid [2-(4,5,6,7-tetrahydro-1H-benzimidazol-5-yl)ethyl]amide,
4,5,6,7-tetrahydro-1H-benzimidazole-5-carboxylic acid
  N-[4-(4-chlorophenyl)butyl]-N-methylamide,
4,5,6,7-tetrahydro-1H-benzimidazole-5-carboxylic acid
  N-methyl-N-(2-phenoxybenzyl)amide,
4,5,6,7-tetrahydro-1H-benzimidazole-5-carboxylic acid
  N-[4-(4-fluorophenyl)butyl]-N-methylamide,
4,5,6,7-tetrahydro-1H-benzimidazole-5-carboxylic acid
  N-methyl-N-[2-(1-naphthyloxy)ethyl]amide,
4,5,6,7-tetrahydro-1H-benzimidazole-5-carboxylic acid
  N-methyl-N-[2-(3-trifluoromethylphenyl)ethyl]amide,
4,5,6,7-tetrahydro-1H-benzimidazole-5-carboxylic acid
  N-[2-(2-chlorophenyl)ethyl]-N-methylamide,
4,5,6,7-tetrahydro-1H-benzimidazole-5-carboxylic acid
  propylamide,
1-cyclohexyl-3-((4,5,6,7-tetrahydro-1H-benzimidazol-5-yl)
  methyl)thiourea,
3-(4-chlorophenyl)-N-((4,5,6,7-tetrahydro-1H-benzimidazol-5-yl)methyl)propionamide,
2-(4-chlorophenyl)-N-((4,5,6,7-tetrahydro-1H-benzimidazol-5-yl)methyl)acetamide,
4-(4-chlorophenyl)-N-((4,5,6,7-tetrahydro-1H-benzimidazol-5-yl)methyl)butyramide,
4,5,6,7-tetrahydro-1H-benzimidazole-5-carboxylic acid [3-(4-chlorophenyl)propyl]amide,
4,5,6,7-tetrahydro-1H-benzimidazole-5-carboxylic acid
  (2-benzimidazol-1-yl-ethyl)amide,
4,5,6,7-tetrahydro-1H-benzimidazole-5-carboxylic acid
  (3-benzimidazol-1-yl-propyl)amide, 4,5,6,7-tetrahydro-1H-benzimidazole-5-carboxylic acid (3-phenylallyl)amide,
4,5,6,7-tetrahydro-1H-benzimidazole-5-carboxylic acid (5-phenylpentyl)amide,
4,5,6,7-tetrahydro-1H-benzimidazole-5-carboxylic acid (4-phenoxybutyl]amide,
4,5,6,7-tetrahydro-1H-benzimidazole-5-carboxylic acid [3-(4-chlorophenoxy)propyl]amide,
4,5,6,7-tetrahydro-1H-benzimidazole-5-carboxylic acid [3-(3-chlorophenoxy)propyl]amide,
4,5,6,7-tetrahydro-1H-benzimidazole-5-carboxylic acid [4-(4-methylphenoxy)butyl]amide,
4,5,6,7-tetrahydro-1H-benzimidazole-5-carboxylic acid [4-(3-methylphenoxy)butyl]amide,
4,5,6,7-tetrahydro-1H-benzimidazole-5-carboxylic acid (5-phenoxypentyl)amide,
4,5,6,7-tetrahydro-1H-benzimidazole-5-carboxylic acid [5-(naphth-1-yloxy)pentyl]amide,
4,5,6,7-tetrahydro-1H-benzimidazole-5-carboxylic acid (2-benzimidazol-1-ylethyl)methylamide,
4,5,6,7-tetrahydro-1H-benzimidazole-5-carboxylic acid (3-benzimidazol-1-ylpropyl)methylamide,
4,5,6,7-tetrahydro-1H-benzimidazole-5-carboxylic acid (3-benzotriazole-1-ylpropyl)methylamide,
4,5,6,7-tetrahydro-1H-benzimidazole-5-carboxylic acid [3-(4-chlorophenyl)propyl]methylamide,
4,5,6,7-tetrahydro-1H-benzimidazole-5-carboxylic acid methyl(5-phenylpentyl)amide,
4,5,6,7-tetrahydro-1H-benzimidazole-5-carboxylic acid [3-(4-chlorophenoxy)propyl]methylamide,
4,5,6,7-tetrahydro-1H-benzimidazole-5-carboxylic acid [3-(3-chlorophenoxy)propyl]methylamide,
4,5,6,7-tetrahydro-1H-benzimidazole-5-carboxylic acid (4-phenoxybutyl]methylamide,
4,5,6,7-tetrahydro-1-H-benzimidazole-5-carboxylic acid [4-(4-methylphenoxy)pentyl]methylamide,
4,5,6,7-tetrahydro-1-H-benzimidazole-5-carboxylic acid methyl-(4-(4-methylphenoxy)butyl)amide,
4,5,6,7-tetrahydro-1H-benzimidazole-5-carboxylic acid methyl-(4-(3-methylphenoxy)butyl)amide,
4,5,6,7-tetrahydro-1H-benzimidazole-5-carboxylic acid methyl-[5-(naphth-1-yloxy)pentyl]amide,
4,5,6,7-tetrahydro-1H-benzimidazole-5-carboxylic acid 2-chlorobenzylamide,
4,5,6,7-tetrahydro-1H-benzimidazole-5-carboxylic acid benzylmethylamide,
7-oxo-7-phenylheptanoic acid [2-(4,5,6,7-tetrahydro-1H-benzimidazol-4-yl)ethyl]amide,
3-(4-chlorophenyl)-N-[2-(4,5,6,7-tetrahydro-1H-benzimidazol-4-yl)ethyl]propionamide,
4-(4-chlorophenyl)-N-[2-(4,5,6,7-tetrahydro-1H-benzimidazol-4-yl)ethyl]butyramide,
6-phenylhexanoic acid [2-(4,5,6,7-tetrahydro-1H-benzimidazol-4-yl)ethyl]amide,
2-(2-chlorophenyl-N-[2-(4,5,6,7-tetrahydro-1H-benzimidazol-4-yl)ethyl]acetamide,
4-chloro-N-[2-(4,5,6,7-tetrahydro-1H-benzimidazol-4-yl)ethyl]benzamide,
2-naphth-2-yl-N-[2-(4,5,6,7-tetrahydro-1H-benzimidazol-4-yl)ethyl]acetamide,
5-phenylpentanoic acid [2-(4,5,6,7-tetrahydro-1H-benzimidazol-4-yl)-ethyl]amide,
2-(4-chlorophenyl)-N-[2-(4,5,6,7-tetrahydro-1H-benzimidazol-4-yl)ethyl]acetamide,
2-naphth-1-yl-N-[2-(4,5,6,7-tetrahydro-1H-benzimidazol-1-yl)ethyl]acetamide,
7-oxo-7-phenylheptanoic acid (4,5,6,7-tetrahydro-1H-benzimidazol-4-ylmethyl)amide,
3-(4-chlorophenyl)-N-(4,5,6,7-tetrahydro-1H-benzimidazol-4-ylmethyl)propionamide,
4-(4-chlorophenyl)-N-(4,5,6,7-tetrahydro-1H-benzimidazol-4-ylmethyl)butyramide,
6-phenylhexanoic acid (4,5,6,7-tetrahydro-1H-benzimidazol-4-ylmethyl)amide,
2-(2-chlorophenyl)-N-(4,5,6,7-tetrahydro-1H-benzimidazol-4-ylmethyl)acetamide,
4-chloro-N-(4,5,6,7-tetrahydro-1H-benzimidazol-4-ylmethyl)benzamide,
2-naphth-2-yl-N-(4,5,6,7-tetrahydro-1H-benzimidazol-4-ylmethyl)acetamide,
5-phenylpentanoic acid (4,5,6,7-tetrahydro-1H-benzimidazol-4-ylmethyl)amide,
2-(4-chlorophenyl)-N-(4,5,6,7-tetrahydro-1H-benzimidazol-4-ylmethyl)acetamide, as well as any optical or geometric isomer or tautomeric form thereof including mixtures of these or a pharmaceutically acceptable salt thereof.

The compounds of the present invention may have one or more asymmetric centres and it is intended that any optical isomers, as separated, pure or partially purified optical isomers or racemic mixtures thereof are included within the scope of the invention.

Furthermore, when a double bond or a fully or partially saturated ring system is present in the molecule geometric isomers may be formed. It is intended that any geometric isomers, as separated, pure or partially purified geometric isomers or mixtures thereof are included within the scope of the invention. Likewise, molecules having a bond with restricted rotation may form geometric isomers. These are also intended to be included within the scope of the present invention.

Furthermore, some of the compounds of the present invention may exist in different tautomeric forms and it is intended that any tautomeric forms, which the compounds are able to form, are included within the scope of the present invention.

The present invention also encompasses pharmaceutically acceptable salts of the present compounds. Such salts include pharmaceutically acceptable acid addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, tactic, maleic, malic, malonic, mandelic, oxalic, ploric, pyruvic, salicylic, succinic, methanesulfonic, ethanesulfonic tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like.

Also intended as pharmaceutically acceptable acid addition salts are the hydrates, which the present compounds are able to form.

The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

The compounds of the present invention may form solvates with standard low molecular weight solvents using methods well known to the person skilled in the art. Such solvates are also contemplated as being within the scope of the present invention.

The invention also encompasses prodrugs of the present compounds, which on administration undergo chemical conversion by metabolic processes before becoming active pharmacological substances. In general, such prodrugs will be functional derivatives of the present compounds, which are readily convertible in vivo into the required compound of the formula (I). Conventional procedures for the selection and preparation of suitable prodrug derivatives are described, for example, in "Design of Prodrugs", ed. H. Bundgaard, Elsevier, 1985.

The invention also encompasses active metabolites of the present compounds.

The compounds of the present invention interact with the histamine H3 receptor and are accordingly useful for the treatment and/or prevention of a wide variety of conditions and disorders in which histamine H3 receptor interactions are beneficial.

Accordingly, in another aspect the present invention relates to a compound of the general formula (I) or any optical or geometric isomer or tautomeric form thereof including mixtures of these or a pharmaceutically acceptable salt thereof for use as a pharmaceutical composition.

The invention also relates to pharmaceutical compositions comprising, as an active ingredient, at least one compound of the formula (I) or any optical or geometric isomer or tautomeric form thereof including mixtures of these or a pharmaceutically acceptable salt thereof together with one or more pharmaceutically acceptable carriers or diluents.

Furthermore, the invention relates to the use of a compound of the general formula (I'):

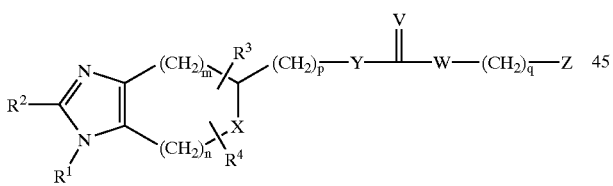

(I')

wherein $R^1$ is hydrogen or a functional group, which can be converted to hydrogen in vivo.

$R^2$ is hydrogen, $C_{1-8}$-alkyl, $C_{1-8}$-alkoxy, $C_{1-8}$-alkylthio, halogen, cyano, trifluoromethyl, hydroxy, thiol or —$NR^5R^6$, wherein $R^5$ and $R^8$ independently are hydrogen or $C_{1-8}$-alkyl, $R^3$ and $R^4$ independently are hydrogen or $C_{1-8}$-alkyl, which is optionally substituted with aryl or heteroaryl, which are optionally substituted with one or more substituents selected from nitro, —$NR^7R^8$, —$S(=O)_2$ $NR^7R^8$, —(=O)$NR^7R^8$, hydroxy, halogen, cyano, trifluoromethyl, —$OCF_3$, —$OCHF_2$, —$OCH_2CHF_2$, $C_{1-8}$-alkyl, $C_{2-8}$-alkenyl, $C_{2-8}$-alkynyl, $C_{1-8}$-alkoxy, $C_{1-8}$-alkylthio, $C_{1-8}$-alkylsulfonyl, —C(=O)$OR^7$, $C_{1-8}$-alkylcarbonyl, —C(=$NOR^7$)$C_{1-8}$-alkyl, $C_{3-10}$-cycloalkyl, $C_{3-10}$-cycloalkylcarbonyl, —C(=$NOR^7$)$C_{3-10}$-cycloalkyl, aryl-$C_{1-8}$-alkyl, heteroaryl-$C_{1-8}$-alkyl, arylamino, heteroarylamino, aroyl, heteroaryl, arylsulfonyl, heteroarylsulfonyl, —C(=$NOR^7$)aryl, —C(=$NOR^7$)heteroaryl, arylthio, heteroarylthio, aryloxy and heteroaryloxy, wherein $R^7$ and $R^8$ independently are hydrogen or $C_{1-8}$-alkyl, m is 0, 1 or 2, n is 1, 2, 3 or 4, X is a valence bond, —O—, —S—, —S(=O)—, —S(=O)$_2$— or —$CF_2$—, p is 0, 1, 2 or 3, Y is a valence bond, —O—, —S— or —$NR^9$—, wherein $R^9$ is hydrogen or $C_{1-8}$-alkyl, V is =O, =S or =$NR^{10}$, wherein $R^{10}$ is hydrogen, cyano, nitro or $C_{1-8}$-alkyl, W is a valence bond, —O—, —S— or —$NR^{11}$—, wherein $R^{11}$ is hydrogen or $C_{1-8}$-alkyl, q is 0, 1, 2 or 3, Z is heteroaryl, aryl, aryloxy, $C_{3-10}$-cycloalkyl, $C_{3-8}$-heterocyclyl or aryl annulated with $C_{3-8}$-heterocyclyl, which are optionally substituted with one or more substituents selected from nitro, —$NR^{12}R^{13}$, —$S(=O)_2NR^{12}R^{13}$, —C(=O) $NR^{12}R^{13}$, hydroxy, halogen, cyano, trifluoromethyl, —$OCF_3$, —$OCHF_2$, —$OCH_2CHF_2$, $C_{1-8}$-alkyl, $C_{1-8}$-alkyl substituted with hydroxy, $C_{2-8}$-alkenyl, $C_{2-8}$-alkynyl, $C_{1-8}$-alkoxy, $C_{1-8}$-alkoxy substituted with hydroxy, $C_{1-8}$-alkylthio, $C_{1-8}$-alkylsulfonyl, —C(=O)$OR^{12}$, $C_{1-8}$-alkylcarbonyl, —C(=$NOR^{12}$) $C_{1-8}$-alkyl, $C_{3-10}$-cycloalkyl, $C_{3-10}$-cycloalkylcarbonyl, —C(=$NOR^{12}$)$C_{3-10}$-cycloalkyl, aryl-$C_{1-8}$-alkyl, heteroaryl-$C_{1-8}$-alkyl, arylamino, heteroarylamino, aroyl, heteroaryl, arylsulfonyl, heteroarylsulfonyl, —C(=$NOR^{12}$) aryl, —C(=$NOR^{12}$)heteroaryl, arylthio, heteroarylthio and heteroaryloxy, wherein $R^{12}$ and $R^{13}$ independently are hydrogen or $C_{1-8}$-alkyl, aryl and aryloxy, which are optionally substituted with one or more substituents selected from $C_{1-8}$-alkyl, $C_{1-8}$-alkoxy, halogen, —$OCF_3$ or —$CF_3$, $C_{1-8}$-alkyl, $C_{2-8}$-alkenyl or $C_{2-8}$-alkynyl, which are optionally substituted with one or more substituents selected from heteroaryl, aryl, aryloxy, aroyl, $C_{3-10}$-cycloalkyl, $C_{3-8}$-heterocyclyl and aryl annulated with $C_{3-8}$-heterocyclyl, which are optionally substituted with one or more substituents selected from nitro, —$NR^{12}R^{13}$, —$S(=O)_2NR^{12}R^{13}$, hydroxy, halogen, cyano, trifluoromethyl, —$OCF_3$, —$OCHF_2$, —$OCH_2CHF_2$, $C_{1-8}$-alkyl, $C_{1-8}$-alkyl substituted with hydroxy, $C_{2-8}$-alkenyl, $C_{2-8}$-alkynyl, $C_{1-8}$-alkoxy, $C_{1-8}$-alkoxy substituted with hydroxy, $C_{1-8}$-alkylthio, $C_{1-8}$-alkylsulfonyl, —C(=O)$OR^{12}$, $C_{1-8}$-alkylcarbonyl, —C(=$NOR^{12}$)$C_{1-8}$-alkyl, $C_{3-10}$-cycloalkyl, $C_{3-10}$-cycloalkylcarbonyl, —C(=$NOR^{12}$)$C_{3-10}$-cycloalkyl, aryl-$C_{1-8}$-alkyl, heteroaryl-$C_{1-8}$-alkyl, arylamino, heteroarylamino, aroyl, heteroaryl, arylsulfonyl, heteroarylsulfonyl, —C(=$NOR^{12}$) aryl, —C(=$NOR^{12}$)heteroaryl, arythio, heteroarylthio and heteroaryloxy, wherein $R^{12}$ and $R^{13}$ independently are hydrogen or $C_{1-8}$-alkyl, aryl and aryloxy, which are optionally substituted with one or more substitutents selected from $C_{1-8}$- alkyl, $C_{1-8}$-alkoxy, halogen, —$OCF_3$ or —$CF_3$, as well as any optical or geomtric isomer or tautomeric form thereof including mixtures of these or a pharmaceutically acceptable salt thereof for the preparation of a pharmaceutical composition for the treatment and/or prevention of disorders and diseases related to the histamine H3 receptor.

In still another aspect, the invention relates to a method for the treatment and/or prevention of diseases and disorders related to the histamine H3 receptor the method comprising administering to a subject in need thereof an effective amount of a compound of the formula (I') or any optical or geometric isomer or tautomeric form thereof including mixtures of these or a pharmaceutically acceptable salt thereof or a pharmaceutical composition comprising the same.

In one aspect the invention relates to compounds with histamine H3 receptor antagonistic activity or inverse agonistic activity which may accordingly be useful in the treatment of a wide range of conditions and disorders in which histamine H3 receptor blockade is beneficial.

In another aspect the invention relates to compounds with histamine H3 receptor agonistic activity and which may accordingly be useful in the treatment of a wide range of conditions and disorders in which histamine H3 receptors activation is beneficial.

In a preferred embodiment of the invention the present compounds are used for the preparation of a pharmaceutical composition for the reduction of weight.

In a preferred embodiment of the invention the present compounds are used for the preparation of a pharmaceutical composition for the treatment and/or prevention of overweight or obesity.

In another preferred embodiment of the invention the present compounds are used for the preparation of a pharmaceutical composition for the suppression of appetite or satiety induction.

In a further preferred embodiment of the invention the present compounds are used for the preparation of a pharmaceutical composition for the prevention and/or treatment of disorders and diseases related to overweight or obesity such as atherosclerosis, hypertension, IGT (impaired glucose tolerance), diabetes, especially Type 2 diabetes (NIDDM (non-insulin dependent diabetes mellitus)), dyslipidaemia, coronary heart disease, gallbladder disease, osteroarthritis and various types of cancer such as endometrial, breast, prostate and colon cancers.

In yet a further preferred embodiment of the invention the present compounds are used for the preparation of a pharmaceutical composition for the prevention and/or treatment of eating disorders such as bulimia and binge eating.

In a further preferred embodiment of the invention the present compounds are used for the preparation of a pharmaceutical composition for the treatment and/or prevention of IGT.

In a further preferred embodiment of the invention the present compounds are used for the preparation of a pharmaceutical composition for the treatment and/or prevention of Type 2 diabetes.

In another preferred embodiment of the invention the present compounds are used for the preparation of a pharmaceutical composition for the delaying or prevention of the progression from IGT to Type 2 diabetes.

In a further preferred embodiment of the invention the present compounds are used for the preparation of a pharmaceutical composition for the delaying or prevention of the progression from non-insulin requiring Type 2 diabetes to insulin requiring Type 2 diabetes.

The compounds of the present invention may also be used for the treatment of airway disorders such as asthma, as anti-diarrhoeals and for the modulation of gastric acid secretion.

Furthermore, the compounds of the present invention may be used for the treatment of diseases associated with the regulation of sleep and wakefulness and for the treatment of narcolepsy and attention deficit disorders.

Moreover, the compounds of the invention may be used as CNS stimulants or as sedatives.

The present compounds may also be used for the treatment of conditions associated with epilepsy. Additionally, the present compounds may be used for the treatment of motion sickness and vertigo. Furthermore, they may be useful as regulators of hypothalamohypophyseal secretion, antidepressants, modulators of cerebral circulation, and in the treatment of irritable bowel syndrome.

Further, the compounds of the present invention may be used for the treatment of dementhia and Alzheimer's disease.

The compounds of the present invention may also be useful for the treatment of allergic rhinitis, ulcer or anorexia.

The compounds of the present invention may furthermore be useful for the treatment of migraine, see R. L. McLeod et al., *The Journal of Pharmacology and Experimental Therapeutics* 287 (1998), 43–50, and for the treatment of myocardial infarction, see C. J. Mackins and R. Levi, *Expert Opinion on Investigational Drugs* 9 (2000), 2537–2542.

The present novel compounds may also interact with the vanilloid receptors, the serotonin receptors, and the adrenergic receptors and may be useful for the treatment of diseases associated with these receptors. Hence, the compounds of the present invention may be vanilloid receptor agonists, and thus be useful for the treatment of obesity by enhancement of the metabolic rate and energy expenditure. Further, by virtue of their interaction with the vanilloid receptor the compounds of the present invention may be useful for the treatment of pain or neurogenic inflammation or inflammatory painful conditions.

In a further preferred embodiment of the invention the present compounds are used for the preparation of a pharmaceutical composition for the treatment and/or prevention of diseases and disorders related to the vanilloid receptor, such as for the treatment and/or prevention of pain, neurogenic inflammation or obesity.

Furthermore, the present compounds may interact with the 5-HT3 receptor (serotonin-3-receptor) and may accordingly be useful as antiemetics, in particular the chemotherapy-induced emesis. Further potential applications of 5-HT3 antagonists include treatment of central nervous system disorders such as anxiety, schizophrenia, drug abuse and withdrawal symptoms, and pathological and age-associated amnesia.

In a further preferred embodiment of the invention the present compounds are used for the preparation of a pharmaceutical composition for the treatment and/or prevention of diseases and disorders related to the serotonin-3 receptor (5-HT3), such as for the treatment of emesis.

Furthermore, the present compounds may interact with the adrenergic alpha-2 receptor and thus be useful for the treatment of hypertension and of a conditions associated with overexpression or hypersensitization of the adrenergic alpha-2 receptor, especially obesity, withdrawal symptoms to an adrenergic alpha-2 agonist, neurological disorders (especially orthostatic hypotension), multiple system atrophy, diabetes mellitus, benigh prostatic hyperplasia or drug induced sensitization of the adrenergic alpha-2 receptor. Moreover, the compounds of the present invention, by virtue of their interaction with the alpha-2 receptor, may be useful as sedatives and hypnotics (sleep inducing agents) or as stimulants.

In a further preferred embodiment of the invention the present compounds are used for the preparation of a pharmaceutical composition for the treatment and/or prevention of diseases and disorders related to the alpha-2 adrenergic receptor, such as for use as a sleep inducing agent.

In a further aspect of the invention the present compounds are combined with diet and/or exercise.

In a further aspect of the invention the present compounds may be administered in combination with one or more further pharmaceutical active substances in any suitable ratios. Such further active agents may be selected from antibesity agents, antidiabetics, antihypertensive agents, agents for the treatment and/or prevention of complications resulting from or associated with diabetes and agents for the treatment and/or prevention of complications and disorders resulting from or associated with obesity.

Thus, in a further aspect of the invention the present compounds may be administered in combination with one or more antiobesity agents or appetite regulating agents.

Such agents may be selected from the group consisting of CART (cocaine amphetamine regulated transcript) agonists. NPY (neuropeptide Y) antagonists, MC4 (melanocortin 4) agonists, MC3 (melanocortin 3) agonists, orexin antagonists. TNF (tumor necrosis factor) agonists, CRF (coricotropin releasing factor) agonists, CRF BP (coritcotropin releasing factor binding protein) antagonists, urocortin agonists, β3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline reuptake inhibitors, mixed serotonin and nonadrenergic compounds, 5HT (serotonin) agonists, bombesin agonists, galanin antagonists, growth hormone, growth factors such as prolactin or placental lactogen, growth hormone releasing compounds. TRH (thyreotropin releasing hormone) agonists, UCP 2 or 3 (uncoupling protein 2 or 3) modulators, leptin agonists, DA agonists (bromocriptin, doprexin), lipase/amylase inhibitors, PPAR (peroxisome proliferator-activated receptor) modulators, RXR (retinoid X receptor) modulators, TR β agonists, AGRP (Agouti related protein) inhibitors, opioid antagonists (such as naltrexone), exendin-4, GLP-1 and ciliary neurotrophic factor.

In one embodiment of the invention the antiobesity agent is leptin.

In another embodiment the antiobesity agent is dexamphetamine or amphetamine.

In another embodiment the antiobesity agent is fenfluramine or dexfenfluramine.

In still another embodiment the antiobesity agent is sibutramine.

In a further embodiment the antiobesity agent is orlistat.

In another embodiment the antiobesity agent is mazindol or phentermine.

In still another embodiment the antiobesity agent is phendimetrazine, diethylpropion, fluoxetine, bupropion, topiramate or ecopipam.

Suitable antidiabetics comprise insulin, GLP-1 (glucagon like peptide-1) derivatives such as those disclosed in VO98/08871 to Novo Nordisk A/S, which is incorporated herein by reference as well as orally active hypoglycaemic agents.

The orally active hypoglycaeimic agents preferably comprise imidazolines, sulphonylureas, biguanides, meglitinides, oxadiazolidinediones, thiazolidinediones, insulin sensitizers, α-glucosidase inhibitors, agents acting on the ATP-dependent potassium channel of the β-cells eg potassium channel openers such as those disclosed in VO97/26265, WO 99/03861 and WO 00/37474 (Novo Nordisk A/S) which are incorporated herein by reference, nateglinide, glucagon antagonists such as those disclosed in WO 99/01423 and WO 00/39088 (Novo Nordisk A/S and Agouron Pharmaceuticals, Inc.), which are incorporated herein by reference, GLP-1 agonists such as those disclosed in WO 00/42026 (Novo Nordisk A/S and Agouron Pharmaceuticals, Inc.), which are incorporated herein by reference, DPP-IV (dipeptidyl peptidase-IV) inhibitors, PTPase (protein tyrosine phosphatase) inhibitors, inhibitors of hepatic enzymes involved in stimulation of gluconeogenesis and/or glycogenolysis, glucose uptake modulators, GSK-3 (glycogen synthase kinase-3) inhibitors, compounds modifying the lipid metabolism such as antilipidemic agents, compounds lowering food intake, PPAR (peroxisome proliferator-activated receptor) and RXR (retinoid X receptor) agonists.

In one embodiment of the invention the present compounds are administered in combination with insulin.

In a further embodiment of the invention the present compounds are administered in combination with a sulphonylurea eg tolbutamide, glibenclamide, glipizide, glimepiride, glicazide or glyburide.

In another embodiment of the invention the present compounds are administered in combination with a biguanide eg metformin.

In yet another embodiment of the invention the present compounds are administered in combination with a meglitinide eg repaglinide or senaglinide.

In still another embodiment of the invention the present compounds are administered in combination with a thiazolidinedione eg trogiltazone, ciglitazone, pioglitazone, rosiglitazone or the compounds disclosed in WO 97/41097, WO 97/41119, WO 97/41120, WO 00/41121 and WO 98/45292 (Dr. Reddy's Research Foundation), which are incorporated herein by reference.

In still another embodiment of the invention the present compounds may be administered in combination with an insulin sensitizer eg such as those disclosed in WO 99/19313, WO 00/50414, WO 00/63191, WO 00/63192, WO 00/63193 (Dr. Reddy's Research Foundation) and WO 00/23425, WO 00/23415, WO 00/23451, WO 00/23445, WO 00/23417, WO 00/23416, WO 00/63153, WO 00/63196, WO 00/63209, WO 00/63190 and WO 00/63189 (Novo Nordisk A/S), which are incorporated herein by reference.

In a further embodiment of the invention the present compounds are administered in combination with an α-glucosidase inhibitor eg miglitol or acarbose.

In another embodiment of the invention the present compounds are administered in combination with an agent acting on the ATP-dependent potassium channel of the β-cells eg tolbutamide, glibenclamide, glipizide, glicazide or repaglinde.

In yet another embodiment of the invention the present compounds may be administered in combination with nateglinide.

In still another embodiment of the invention the present compounds are administered in combination with an antilipidemic agent eg cholestyramine, colestipol, clofibrate, gemfibrozil, lovastatin, pravastalin, simvastatin, probucol or dextrothyroxine.

In another aspect of the invention, the present compounds are administered in combination with more than one of the above-mentioned compounds eg in combination with metformin and a sulphonylurea such as glyburide; a sulphonylurea and acarbose; nateglinide and metformin; acarbose and meformin; a sulfoylurea, metformin and troglitazone; insulin and a sulfonylurea; insulin and metformin; insulin, metformin and a sulfonylurea; insulin and troglitazone, insulin and lovastatin; etc.

Furthermore, the present compounds may be administered in combination with one or more antihypertensive agents. Examples of antihypertenisve agents are β-blockers such as alprenolol, atenolol, timoki, pindolol, propranolol and metoproiol ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19$^{th}$ Edition, Gennaro, Ed., Mack Publishing Co., Easton, Pa. 1985.

It should be understood that any suitable combination of the compounds according to the invention with diet and/or exercise, one or more of the above-mentioned compounds and optionally one or more other active substances are considered to be within the scope of the present invention.

PHARMACEUTICAL COMPOSITIONS

The compounds of the invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: the Science and Practice of Pharmacy, 19$^{th}$ Edition, Gennaro, Ed., Mack Publishing Co. Easton, Pa. 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings such as enteric coatings or they can be formulated so as to provide controlled release of the active ingredient such as sustained or prolonged release according to methods well known in the art.

Liquid dosage forms for oral administration include solutions, emulsions, suspensions, syrups and elixirs.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. Depot injectable formulations are also contemplated as being within the scope of the present invention.

Other suitable administration forms include suppositories, sprays, ointments, cremes, gels, inhalants, dermal patches, implants etc.

A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain of from 0.05 to about 1000 mg, preferably from about 0.1 to about 500 mg, and more preferred from about 0.5 mg to about 200 mg.

For parenteral routes, such as intravenous, intrathecal, intramuscular and similar administration, typically doses are in the order of about half the dose employed for oral administration.

The compounds of this invention are generally utilized as the free substance or as a pharmaceutically acceptable salt thereof. One example is an acid addition salt of a compound having the utility of a free base. When a compound of the formula (I) contains a free base such salts are prepared in a conventional manner by treating a solution or suspension of a free base of the formula (I) with a chemical equivalent of a pharmaceutically acceptable acid, for example, inorganic and organic acids. Representative examples are mentioned above. Physiologically acceptable salts of a compound with a hydroxy group include the anion of said compound in combination with a suitable cation such as sodium or ammonium ion.

For parenteral administration, solutions of the novel compounds of the formula (I) in sterile aqueous solution, aqueous propylene glycol or sesame or peanut oil may be employed. Such aqueous solutions should be suitable buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid or lower alkyl enters of cellulose. Examples of liquid carriers are syrup, peanut oil, olive oil, phospholipids, fatty acids, fatty acid amines, polyoxyethylene or water. Similarly, the carrier or diluent may include any sustained release material known in the art, such as glyceryl monosterate or glyceryl distearate, alone or mixed with a wax. The pharmaceutical compositions formed by combining the novel compounds of the formula (I) and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. These formulations may be in the form of powder or granules, as a solution or suspension in an aqueous or non-aqueous liquid, or as an oil-in-water or water-in-oil liquid emulsion.

If a solid carrier is used for oral administration, the preparation may be tabletted, placed in a hard gelatine capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

A typical tablet, which may be prepared by conventional tabletting techniques, may contain:

| Core: | |
|---|---|
| Active compound (as free compound or salt thereof) | 5.0 mg |
| Lactosum Ph. Eur. | 67.8 mg |
| Cellulose, microcryst. (Avicel) | 31.4 mg |
| Amberlite ® IRP88* | 1.0 mg |
| Magnesii stearas Ph. Eur. | q.s. |
| Coating: | |
| Hydroxypropyl methylcellulose | approx. 9 mg |
| Mywacett 9–40 T** | approx. 0.9 mg |

*Polacrillin potassium NF, tablet disintegrant, Rohm and Haas.
**Acylated monoglyceride used as plasticizer for film coating.

If desired, the pharmaceutical composition of the invention may comprise the compound of the formula (I) in combination with further pharmacologically active substances such s those described in the foregoing.

The preparation of the compounds of this invention can be realised in many different ways. The starting imidazole derivatives of the formulae (II), (IX) and (XIV) may be prepared according to procedures described in literature (see eg Croat. Chem. Acta. 1973, 45, 297. J. Am. Chem. Soc. 1976, 98, 984). The other reactants are either known compounds or compounds that may be prepared in analogy with the preparation of similar known compounds.

Method A

Compounds of the formula (Ia) according to the invention wherein m, n, p, $R^{11}$, q and Z are as defined for formula (I) can be prepared as outlined below:

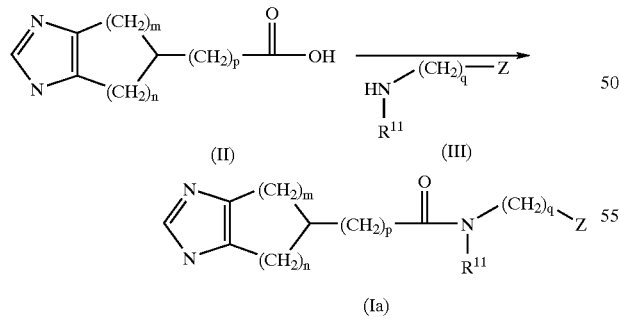

The carboxylic acid group of a compound of the formula (II) wherein m, n and p are as defined above may be activated and reacted with a compound of the formula (III) wherein $R^{11}$, q and Z are as defined above. This amidation reaction may be carried out in a suitable solvent like eg DCM at a temperature of up to reflux for the solvent used for eg 1–200 hours.

Method B

Compounds of the formula (Ib) according to the invention wherein m, n, p, q and Z are as defined for formula (I) can be prepared as outlined below:

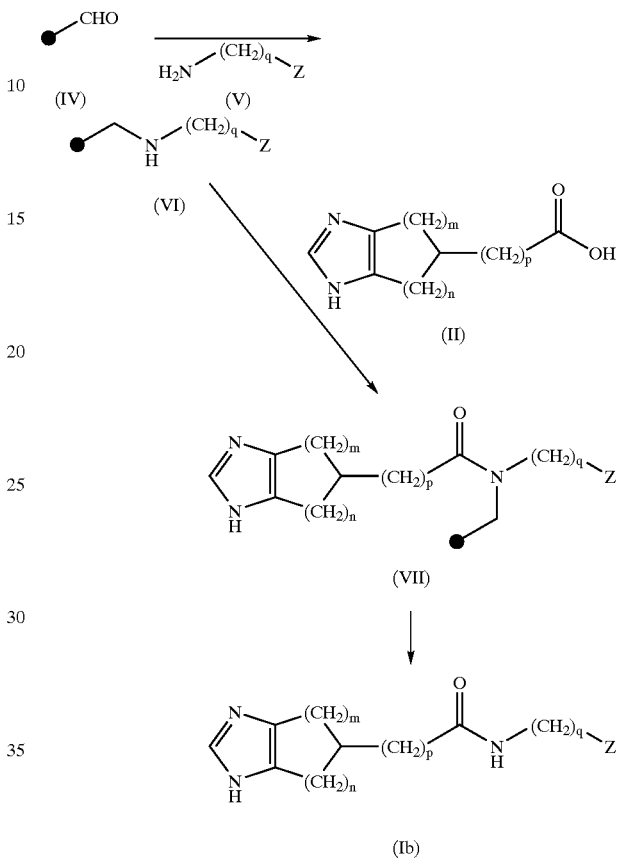

A primary amine of the formula (V) wherein q and Z are as defined above can be attached to a functionalised polystyrene via reductive amination to give a secondary solid supported amine of the formula (VI). The secondary amine of the formula (VI) can then be acylated with an activated carboxylic acid of the formula (II) wherein m, n and p are as defined above to give solid supported amide of the formula (VII). The amide of the formula (VII) may then be cleaved from the solid support to give the amide of the formula (Ib).

Method C

Compounds of the formula (Ic) according to the invention wherein m, n, p, q and Z are as defined for formula (I) can be prepared as outlined below:

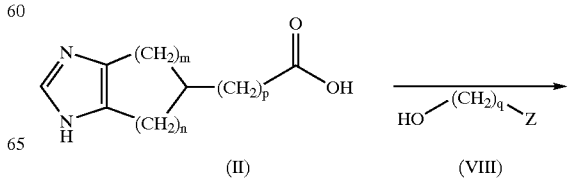

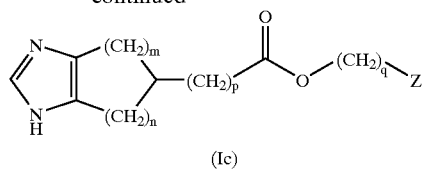

(Ic)

The carboxylic acid group in a compound of the formula (II) wherein m, n and p are as defined above may be activated and reacted with a compound of the formula (VIII) wherein q and Z are as defined above.

Method D

Compounds of the formula (Id) according to the invention wherein m, n, p, $R^{11}$, q and Z are as defined for formula (I) can be prepared as outlined below:

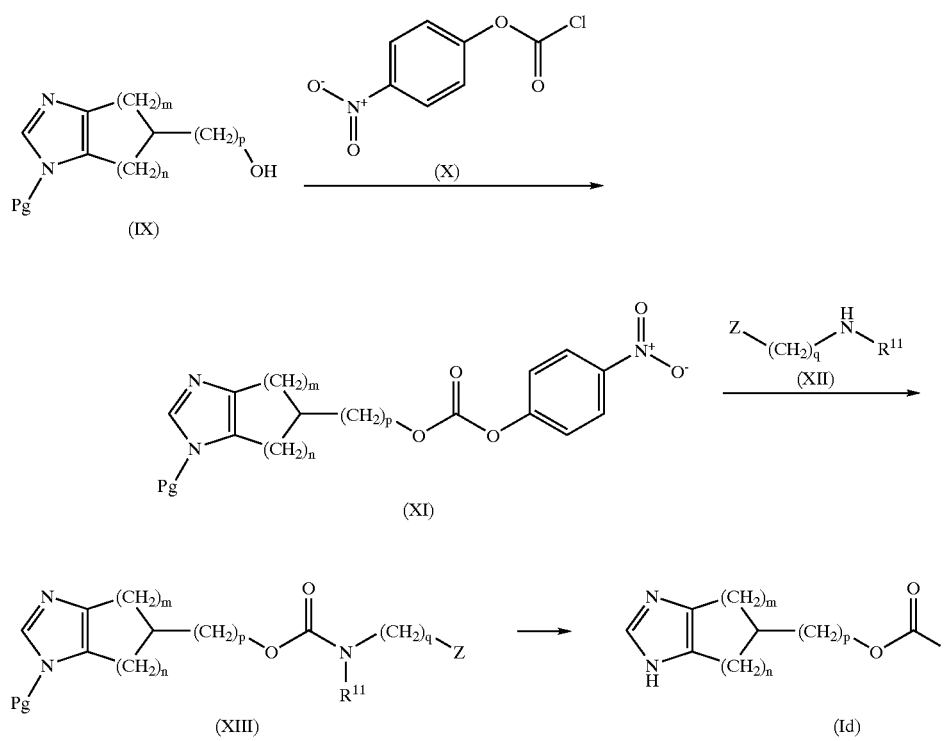

The alcohol group in a compound of the formula (IX) wherein m, n and p are as defined above and Pg represents a protecting group like eg triphenylmethyl (trityl) may be reacted with a double activated formate compound of the formula (X) like eg 4-nitrophenyl chloroformate to give an activated carbonate derivative of the formula (XI). The activated carbonate derivative of the formula (XI) may then be reacted with amines of the formula (XII) wherein $R^{11}$, q and Z are as defined above to give a carbamate of the formula (XIII). Removal of the protecting group from a compound of the formula (XIII) is accomplished with dilute acid to give a compound of the formula (Id).

Method E

Compounds of the formula (Ie) according to the invention wherein q and Z are as defined for formula (I) can be prepared as outlined below:

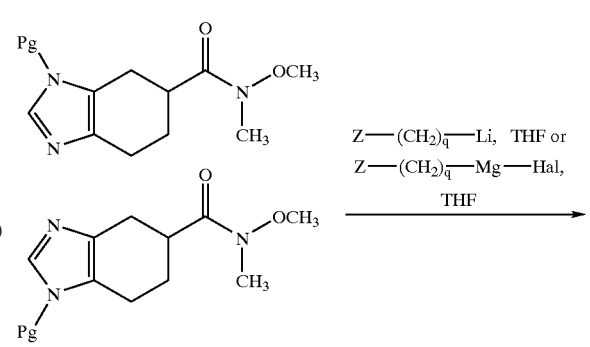

(XIV)

-continued

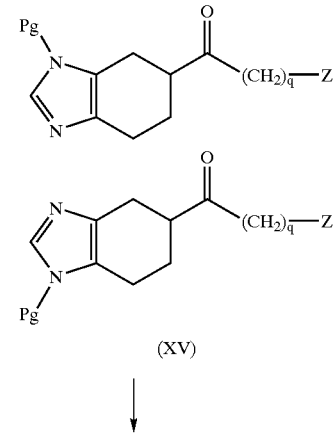

(XV)

(Ie)

The Weinreb amide in a compound of the formula (XIV) wherein Pg represents a protecting group like eg triphenylmethyl (trityl) may be reacted with a lithium or Grignard salt to give a ketone of the formula (XV). Removal of the protecting group from a compound of the formula (XV) is accomplished with dilute acid to give a compound of the formula (Ie).

Method F

Compounds of the formula (If) according to the invention wherein m, n, p, q and Z are as defined for formula (I) can be prepared as outlined below:

(XVI)

(If)

The amino group in a compound of the formula (XVI) wherein m, n and p are as defined above may be reacted with an activated carboxylic acid of formula (XVII) wherein q and Z are as defined above to give an amide of the formula (If). Activation of the carboxylic acid may be accomplished using CDI or HOAt/DIC. Alternatively, the carboxylic acid may be activated as the acid chloride by thionyl chloride. Activation of the carboxylic acid may be carried out in a suitable solvent like eg DC or DMA at a temperature of up to reflux for the solvent used for eg 1–200 hours.

Method G

Compounds of the formula (g) according to the invention wherein m, n, p, q, V and Z are as defined for formula (I) can be prepared as outlined below:

(XVIII)

(Ig)

The amino group in a compound of the formula (XVII) wherein m, n and p are as defied above may be reacted with an isocyanate or isothiocyanate of formula (XIX) wherein q, V and Z are as defined above to give an urea or thiourea of the formula (Ig). This reaction may be carried out in a suitable solvent like e.g. an alcohol at a temperature of up to reflux for the solvent used for e.g. 1–200 hours.

The present invention is further illustrated by the following representative examples, which are, however, not intended to limit the scope of the invention in any way.

EXAMPLES

In the examples the following terms are intended to have the following, general meanings:

CDI: carbonyldiimidazole

DBU: 1,8-diazabicyclo[5.4.0]undec-7-ene

DCM: dichloromethane, methylenechloride

DEAD: diethyl azodicarboxylate

DIC: diisopropylcarbodiimide

DIPEA: diisopropylethylamine

DMA: N,N-dimethylacetamide

DMF: N,N-dimethylformamide

DMSO: dimethyl sulfoxide

NMP: N-methylpyrrolidin-2-one

TFA: trifluoroacetic acid

THF: tetrahydrofuran

HOAt: 1-hydroxy-7-azabenzotriazole

NMR spectra were recorded on Bruker 300 MHz and 400 MHz instruments. HPLC-MS was performed on a Perkin Elmer Instrument (API 100), and HPLC-systems from Merck-Hitachi or Waters.

HPLC method A

Hibar™ RT 250-4, Lichrosorb™ RP-18, 5.0 µm, 4.0×125 mm; gradient elution, 5% to 80% solvent B (0.1% TFA in acetonitrile) in solvent A (0.1% TFA in water) with 15 min, 2.0 ml/min, detection at 214 nm, temperature 35° C.

HPLC method B

LiChroCART LiChrospher™ 100 RP-18, 5.0 µm, 4.0×250 mm; gradient elution, 25% to 80% solvent B (0.1% TFA in acetonitrile) in solvent A (0.1% TFA in water) within 20 min, 2.0 ml/min, detection at 214 nm, temperature 35° C.

HPLC method C

218TP54 C-18 silica column, 4.6 mm×150 mm; linear gradient elution from 5% acetonitrile, 85% water and 10% of a solution of 0.5% TFA in water to 90K acetonitrile and 10% of a solution of 0.5% TFA in water within 15 min, 1 ml/min, detection at 214 nm, temperature 42° C.

HPLC method D

Hibar™ RT 250-4, Lichrosorb™ RP-18, 5.0 µm, 4.0×250 mm; gradient elution, 20% to 80% solvent B (0.1% TFA in acetonitrile) in solvent A (0.1% TFA in water) within 30 min, 1.0 ml/min, detection at 214 nm, temperature 30° C.

HPLC method E

Hibar™ RT 125-4, 5.0 µm, 4.0×125 mm; gradient elution, 5% to 80% solvent B (0.1% TFA in acetonitrile) in solvent A (0.1% TFA in water) within 10 min, 2.0 ml/min, detection at 214 nm, temperature 35° C.

Example 1

4,5,6,7-Tetrahydro-1H-benzimidazole-5-carboxylic acid ((1S)-(naphth-1-yl)ethyl-amide

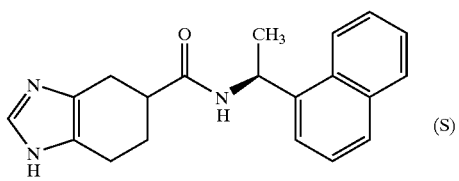

Step 1: 4,5,6,7-Tetrahydro-1H-benzimidazole-5-carboxylic acid, hydrochloride salt

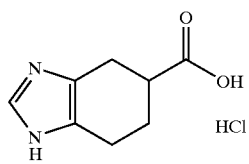

A solution of benzimidazole-5-carboxylic acid (10 g, 62 mmol) in 1 N hydrochloric acid (70 ml) and $H_2O$ (30 ml) was hydrogenated at 100 bar and 80° C. in the presence of 10% palladium on carbon (2.5 g) for 2 days. The mixture was filtered and the solvent was evaporated. The residue was stirred with acetone (100 ml) and the solid was isolated and dried. This afforded 10.6 g (79%) of 4,5,6,7-tetrahydro-1H-benzimidazole-5-carboxylic acid hydrochloride. Mp. 248–250° C.; Lit Mp. 247–248° C. (Croat. Chem. Acta. 1973, 45, 297). HPLC method A; elution at 1.99 min. $^1$H NMR (400 MHz, DMSO-$d_6$) δ 1.8–1.9 (m, 1H), 2.1–2.2 (m, 1H), 2.65 (m, 2H), 2.7–2.9 (m, 3H), 8.90 (s, 1H), 12.6 (brs), 14.5 (brs).

Step 2:

To a suspension of 4,5,6,7-tetrahydro-1H-benzimidazole-5-carboxylic acid, hydrochloride (1.1 g, 5 mmol) in CDM (40 ml), DIPEA (1.3 ml, 7.5 mmol), DIC (1.2 ml, 7.5 mmol) and HOAt (0.75 g, 5.5 mmol) were added and the mixture was stirred for 1 hour under an atmosphere of nitrogen. (S)-(−)-1-(Naphth-1-yl)ethylamine (0.86 g, 5 mmol) was added and the mixture was stirred at room temperature for 2 days. DCM (25 ml), $H_2O$ (100 ml) and 1 N hydrochloric acid were added until pH 1. The phases were separated and the organic phase was extracted with $H_2O$ (3×50 ml). The organic phase was discarded and the acidic aqueous extracts were combined and 12 N sodium hydroxide was added until pH 11–12. The resulting mixture was extracted with ethyl acetate (300 ml) and the separated organic phase was dried (magnesium sulphate). Oxalic acid (0.5 g) dissolved in ethyl acetate was added to the dried ethyl acetate solution to give an oily precipitate. The solvent was decanted and the oily residue was dissolved in $H_2O$ (300 ml) and 1 N sodium hydroxide was added until pH 11. The alkaline mixture was extracted with ethyl acetate (150 ml) and the organic extract was dried (magnesium sulphate). The solvent was evaporated to give a solid residue, which was stirred with diethyl ether. The resulting solid was isolated to give 0.6 g of the title compound. The last drying filtercake was dissolved in $H_2O$ (50 ml) and the resulting solid was isolated by filtration and dried to give another 0.65 g of the title compound. Total yield: 1.25 g (78%). Mp. 158–160° C. HPLC method B: elution at 6.12 min. LC-MS: Calc for MH$^+$: 320.4; Found: 320.6. $^1$H NMR (400 MHz, DMSO-$d_6$) δ 1.52 (d, 3H), 1.6–1.8 (m, 1H), 1.85–2.05 (m, 1H), 2.45–2.65 (m, 5H), 5.75 (m, 1H), 7.38 (s, 1H), 7.48–7.60 (m, 4H), 7.83 (d, 1H), 7.95 (d, 1H), 8.10 (d, 1H), 8.5 (brs, 1H), 11.6 (brs).

Example 2

4,5,6,7-Tetrahydro-1H-benzimidazole-5-carboxylic acid ((1R)-(naphth-1-yl)-ethyl)amide, hydrochloride salt

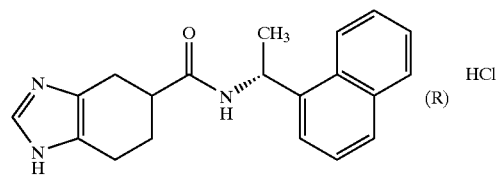

By a similar procedure as described in Example 1 the title compound was prepared. Mp. 84–85° C. (amorph.), HPLC method B: elution at 5.90 min. LC-MS: Calc for MH$^+$: 320.4; Found: 320.6. $^1$H NMR (400 MHz, DMSO-$d_6$) δ 1.52 (d, 3H), 1.75–1.95 (m, 1H), 1.95–2.15 (m, 1H), 2.5–2.7 (m, 5H), 5.72 (m, 1H), 7.48–7.58 (m, 4H), 7.83 (d, 1H), 7.95 (d, 1H), 8.09 (d, 1H), 8.75 (2×d, 1H), 8.87 (s, 1H), 14.3 (brs).

Example 3

4,5,6,7-Tetrahydro-1H-benzimidazole-5-carboxylic acid (naphth-1-ylmethyl)-amide, hydrochloride salt

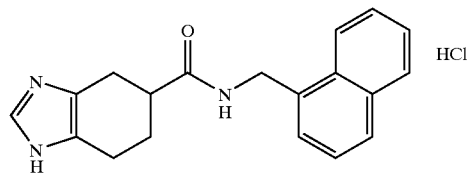

By a similar procedure as described in Example 1 using 4,5,6,7-tetrahydro-1H-benzimidazole-5-carboxylic acid, hydrochloride (2.2 g, 10 mmol) and 1-(naphth-1-yl)ethylamine (1.6 g, 10 mmol), 4,5,6,7-tetrahydro-1H-benzimidazole-5-carboxylic acid (naphth-1-ylmethyl)amide (2.0 g, 67%) was obtained. The free base was dissolved in 1 N hydrochloric acid (5 ml) and the mixture was diluted with $H_2O$ (10 ml). On standing a precipitate was formed which was isolated and dried to give the title compound (0.95 g).

Mp. 142–144° C. HPLC method B: elution at 5.38 min. LC-MS: Calc for MH$^+$: 306.4: Found: 306.4. $^1$H NMR (400 MHz, DMSO-$d_6$) δ 1.85 (m, 1H), 2.0–2.1 (m, 1H), 2.5–2.8 (m, 5H), 4.76 (dq, 2H), 7.45–7.60 (m, 4H), 7.85 (d, 1H), 7.97 (d, 1H), 8.06 (d, 1H), 8.65 (t, 1H), 8.88 (s, 1H), 14.3 (brs).

Example 4

Solid Phase Synthesis of Carboxamides

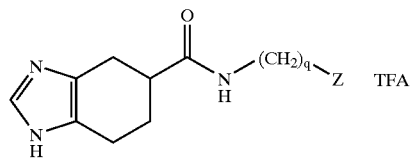

The each reactor in an array of six, 2-formyl-5-methoxyphenoxyethylpolystyrene (100 mg, 0.55 mmol/g) and NMP (2 ml) were added and the array was shaken for 15 min. To each reactor $H_2O$ (0.2 ml) was added followed by a primary amine (0.55 mmol, Z-$(CH_2)_q$-$NH_2$ as listed below). To each reactor a mixture of sodium cyanoborohydride (36 mg, 0.57 mmol) in THF (2 ml) were added and the array was shaken vigorously. Acetic acid (0.04 ml) was added to each reactor and the array was shaken for 2 days. Each reactor was washed with methanol (3×), NMP (3×), DCM (3×), methanol (3×) and DCM (3×). NMP (1.0 ml) was added to each reactor followed by the activated acid (2.5 ml of a mixture prepared from 4,5,6,7-tetrahydro-1H-benzimidazole-5-carboxylic acid, hydrochloride (1.1 g, 5 mmol), DCM (15 ml), NMP (5 ml), triethylamine (0.7 ml), DIC (1.17 ml) and HOAt (1.0 g) that was stirred at room temperature for 1h) and the array was shaken for 4 days. Each reactor was washed with NMP (3×), THF (3×), methanol (3×), DCM (3×), methanol (3×) and DCM (3×). To each reactor DCM (2.5 ml) and TFA (1.2 ml) were added and the array was shaken for 3 hours. The cleavage mixtures were isolated and the volatiles were removed under reduced pressure to give the following six amides, identified by their MH+ (LC-MS):

| Example | Z—$(CH_2)_q$— | Yield mg | MH+ (calcd) | MH+ (found) |
|---|---|---|---|---|
| 4-001 | 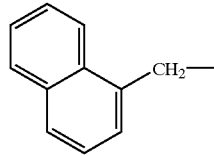 | 11.4 | 306.4 | 306.4 |
| 4-002 | 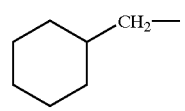 | 4.5 | 262.4 | 262.4 |
| 4-003 | 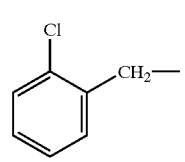 | 8.6 | 290.8 | 290.4 |
| 4-004 | 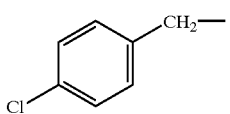 | 1.4 | 290.8 | 290.4 |
| 4-005 | 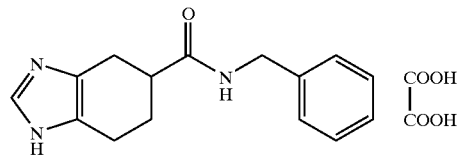 | 10.4 | 292.3 | 292.4 |
| 4-006 | 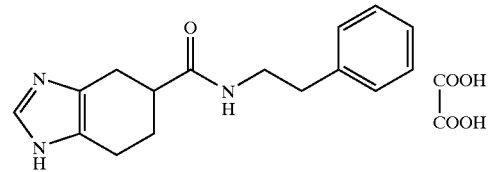 | 5.4 | 286.4 | 286.4 |

Example 5

4,5,6,7-Tetrahydro-1H-benzimidazole-5-carboxylic acid benzylamide, oxalic acid salt By a similar procedure as described in Example 1 the title compound was prepared. Mp. 130–132° C. HPLC method A: elution at 4.14 min. LC-MS: Calc for MH+: 256.3; Found: 256.4. $^1$H NMR (400 MHz, DMSO-$d_6$) δ 1.75–1.85 (m, 1H), 2.0–2.1 (m, 1H), 2.5–2.8 (m, 5H), 4.30 (dq, 2H), 7.2–7.50 (m, 5H), 8.53 (s, 1H), 8.56 (t, 1H).

Example 6

4,5,6,7-Tetrahydro-1H-benzimidazole-5-carboxylic acid 2-phenylethylamide, oxalic acid By a similar procedure as described in Example 1 the title compound was prepared. Mp. 197–199° C. HPLC method A: elution at 4.65 min. LC-MS: Calc for MH+: 270.4; Found: 270.6. $^1$H NMR (400 MHz, DMSO-$d_6$) δ 1.65–1.75 (m, 1H), 1.85–1.95 (m, 1H), 2.4–2.6 (m, 5H), 2.72 (t, 2H), 3.30 (m, 2H), 7.15–7.35 (m, 5H), 7.74 (s, 1H), 8.00 (t, 1H).

Example 7

4,5,6,7-Tetrahydro-1H-benzimidazole-5-carboxylic acid (N-(2-naphthylmethyl)-N-methylamide

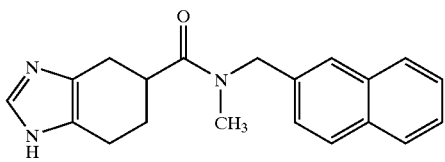

By a similar procedure as described in Example 1 the title compound was prepared. HPLC method C: elution at 8.48 min. LC-MS: Calc for MH$^+$: 320; Found: 320. $^1$H NMR (400 MHz, DMSO-d$_6$, two rotamers, 2:1): δ 1.65–2.10 (m, 2H), 2.34–2.70 (m, 4H), 2.94 and 3.05 (both s, together 3H), 3.00–3.15 (m, 1H), 4.70 and 4.87 (both AB, together 2H), 7.30–7.60 (m, 4H), 7.70 and 7.74 (both s, together 1H), 7.80–8.00 (m, 3H), 11.5 (brs, 1H).

Example 8

4,5,6,7-Tetrahydro-1H-benzimidazole-5-carboxylic acid N-methyl-N(2-(2-naphthyl)ethyl)amide

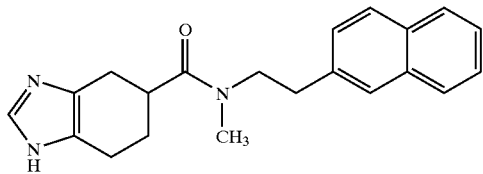

By a similar procedure as described in Example 1 the title compound was prepared. HPLC method C: elution at 8.58 min. LC-MS: Calc for MH$^+$: 334; Found: 334. $^1$H NMR (400 MHz, DMSO-d$_6$, two rotamers, 1:1): δ 1.60, 1.80, 2.05, 2.25–2.70 (all m, together 6H), 3.05 and 3.20 (both s, together 3H), 3.05–3.25 (m, 3H), 3.70–4.00 (m, 2H), 7.50–7.70 (m, 4H), 7.90 (s, 1H), 7.95–8.10 (m, 3H), 11.85 (br, 1H).

Example 9

4,5,6,7-Tetrahydro-1H-benzimidazole-5-carboxylic acid N-methyl-N-((1-naphthyl)methylamide

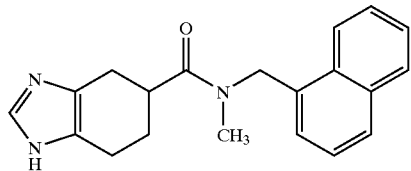

By a similar procedure as described in Example 1 the title compound was prepared. HPLC method C: elution at 8.42 min. LC-MS: Calc for MH$^+$: 320; Found: 320. $^1$H NMR (400 MHz, CDCl$_3$, two rotamers, 2:1): δ 2.10 (m, 2H), 2.40–3.10 (m, 5H), 2.92 and 3.22 (both s, together 3H), 5.10 and 5.11 (both AB, together 2H), 7.10–8.10 (m, together 9H).

Example 10

4,5,6,7-Tetrahydro-1H-benzimidazole-5-carboxylic acid ((2,3-dihydrobenzofuran-7-yl)methyl)amide

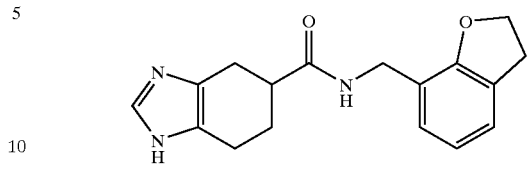

Step 1: 2,3-Dihydrobenzofuran-7-carboxylic acid amide

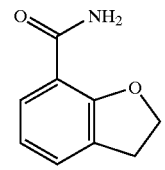

2,3-Dihydrobenzofuran-7-carboxylic acid (15.0 g, 91 mmol) was dissolved in DCM (150 ml) and DMF (150 ml). 1-Hydroxybenzotriazole (12.3 g, 91 mmol) was added. The solution was cooled to 0° C. N-(3-Dimethylaminopropyl)-N'-ethylcarbodiimide hydrochloride (17.5 g. 91 mmol) was added. The reaction mixture was stirred for 20 min at 0° C. A 1 N solution of ammonia in methanol (200 ml, 200 mmol) was added. The reaction mixture was stirred for 16 hours, while it was warming up to room temperature. It was diluted with ethyl acetate (200 ml) and washed with a 10% aqueous sodium hydrogensulphate solution. The aqueous phase was extracted with ethyl acetate (2×100 ml). The combined organic layers were washed with a saturated aqueous solution of sodium hydrogen carbonate (400 ml) and dried over magnesium sulphate. The solvent was removed in vacuo. The remaining crystals were washed with ethyl acetate (3×100 ml) and dried in vacuo to give 5:21 g of 2,3-dihydrobenzofuran-7-carboxylic acid amide.

$^1$H NMR (DMSO-d$_6$) δ 3.25 (t, 2H), 4.70 (t, 2H), 6.94 (t, 1H), 7.25 (br, 1H), 7.40 (d, 1H), 7.55 (br, 1H), 7.60 (d, 1H).

Step 2: ((2,3-Dihydrobenzofuran-7-yl)methyl)amine

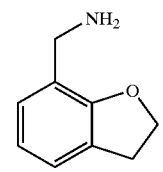

At 0° C., a solution of 2,3-dihydrobenzofuran-7-carboxylic acid amide (5.2 g, 31 mmol) in THF (100 ml) was added drop wise to a suspension of sodium borohydride in THF. The mixture was stirred for 20 min at 0° C. A solution of iodine (4.1 g, 16 mmol) in THF (100 ml) was added drop wise. After the addition was finished, the reaction mixture was heated for 16 hours to reflux. It was cooled to room temperature. Methanol (260 ml) was added drop wise. The solvent was removed in vacuo. The residue was dissolved in a 20% aqueous solution of sodium hydroxide (200 ml) and tert-butyl methyl ether (200 ml). The phases were separated. The aqueous phase was extracted with tert-butyl methyl ether (2×100 ml). The combined organic layers were dried over magnesium sulphate. The solvent was remove din vacuo. The crude product was purified by flash chromatography on silica (90 g), using DCM/methanol/25% aqueous ammonia (100:10:1) as eluent to give 0.93 g of ((2,3-dihydrobenzofuran-7-yl)methyl)amine.

¹H NMR (DMSO-d₆) δ 2.20 (br, 2H), 3.10 (t, 2H), 3.60 (s, 2H), 4.50 (t, 2H), 6.77 (t, 1H), 7.08 (d, 1H), 7.11 (d, 1H).

Step 3:

By a similar procedure as described in Example 1, the title compound was prepared. HPLC method C: elution at 6.83 min. LC-MS: Calc For MH⁺: 298; found 298. ¹H NMR (CDCl₃): δ 1.95 (m, 1H), 2.15 (m, 1H), 2.50–2.90 (m, 5H), 3.21 (t, 2H), 4.44 (d, 2H), 4.57 (t, 2H), 5.25 (t, 1H); 6.80 (t, 1H), 7.03 (d, 1H), 7.11 (d, 1H), 7.45 (s, 1H).

Example 11

4,5,6,7-Tetrahydro-1H-benzimidazole-5-carboxylic acid 4-trifluoromethylbenzylamide

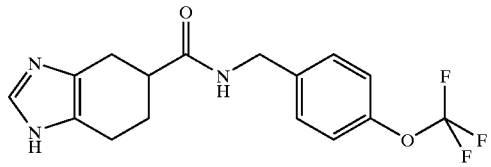

By a similar procedure as described in Example 1 the title compound was prepared. HPLC method C: elution at 9.09 min. LC-MS: Calc for MH⁺: 340; Found: 340. ¹H NMR (CDCl₃): δ 2.00 (m, 1H), 2.15 (m, 1H), 2.50–3.00 (m, 5H), 4.42 (ABX, 2H), 6.32 (t, 1H), 7.15 (d, 2), 7.25 (d, 2), 7.45 (s, 1H).

Microanalysis for C₁₆H₁₆F₃N₃O₂H₂O: Calc: C: 53.78%; H: 5.08%; N: 11.76%. Found: C: 54.02%; H: 4.97%; N: 11.74%.

Example 12

4,5,6,7-Tetrahydro-1H-benzimidazole-5-carboxylic acid 4-trifluoromethylbenzylamide

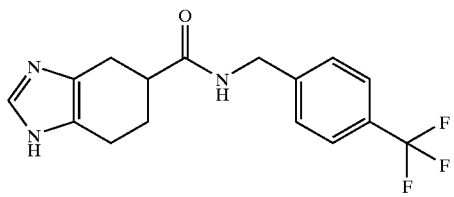

320 mg (85%) of the title compound was prepared by a similar procedure as described in Example 1.

HPLC method C: elution at 8.21 min. LC-MS: Calc for MH³⁰: 324; Found: 324. ¹H NMR (DMSO-d₆) δ 1.75 (m, 1H), 2.03 (m, 1H), 2.45–2.70 (m, 5H), 4.40 (ABX, 2H), 7.40 (s, 1H), 7.48 (d, 2H), 7.70 (d, 2H), 8.54 (t, 1H), 11.60 (br, 1H).

Microanalysis for C₁₆H₁₆F₃N₃O,½ H₂O: Calc: C: 57.83%; H: 5.16%; N: 12.64%. Found: C: 57.98%; H: 5.21%; N: 12.61%.

Example 13

4,5,6,7-Tetrahydro-1H-benzimidazole-5-carboxylic acid (benzo[b]thiophen-5-ylmethyl)amide

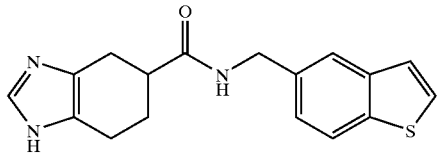

Step 1: 5-Bromomethylbenzo[b]thiophene

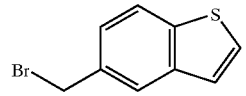

A mixture of 5-methylbenzo[b]thiophene (5.0 g, 33.7 mmol), N-bromosuccinimide (5.7 g, 32.0 mmol) and dibenzoylperoxide (0.25 g, 1.01 mmol) in tetrachloromethane was heated to reflux for 2 hours. It was cooled to room temperature and left for 16 hours. The solid was filtered off. The solvent was removed in vacuo. The crude product was purified by flash chromatography on silica (300 g), using ethyl acetate/heptane (1:10) as eluent, to give 6.37 g (83%) of 5-bromomethylbenzo[b]thiophene.

¹H NMR (CDCl₃): δ 4.60 (s, 2H), 7.28 (d, 1H), 7.35 (d, 1H), 7.45 (d, 1H), 7.70 (m, 2H).

Step 2: ((Benzo[b]thiophen-5-yl)methyl)amine

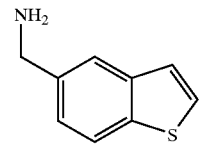

A solution of 5-bromomethylbenzo[b]thiophene (3.0 g, 13.20 mmol) in DMF (15 ml) was added to a solution of 25% aqueous ammonia (10 ml, 132 mmol) in DMF (10 ml). The reaction mixture was stirred for 4 hours at room temperature. The solvent was removed in vacuo. The crude product was purified by flash chromatography on silica (40 g), using first ethyl acetate/heptane (1:1; 60 ml) and subsequently DCM/methanol/25% aqueous ammonia (100:10:1) as eluent, to give 0.40 g (19%) of ((benzo[b]thiophen-5-yl)methyl)amine.

¹H NMR (DSMO-d₆) δ 3.85 (s, 2H), 7.40 (m, 2H), 7.75 (d, 1H), 7.85 (s, 1H), 7.92 (d, 1H).

Step 3:

205 mg (56%) of the title compound was prepared by a similar produce as described in Example 1.

HPLC method C: elution at 9.14 min. LC-MS: Calc for MH⁺: 312; Found: 312. ¹H NMR (DMSO-d₆) δ 1.77 (m, 1H), 2.05 (m, 1H), 2.40–2.70 (m, 5H), 4.45 (ABX, 2H), 7.30 (d, 1H), 7.40 (d, 1H), 7.45 (d, 1H), 7.75 (m, 2H), 7.95 (d, 1H), 8.5 (br, 1H), 11.60 (s, 1H).

Microanalysis for C₁₇H₁₇N₃OS,H₂O: Calc: C: 61.98%; H: 5.81%; N: 12.76%. Found: C: 62.95%; H: 5.55%; N: 12.95%.

Example 14

4,5,6,7-Tetrahydro-1H-benzimidazole-5-carboxylic acid ((benzo[b]thiophen-2-yl)methyl)amide

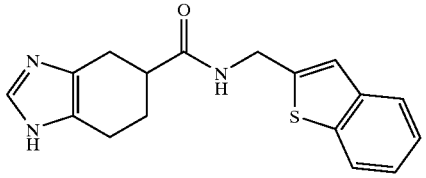

296 mg (80%) of the title compound was prepared by a similar procedure as described in Example 1, starting with ((benzo[b]thiophen-2-yl)methyl)amine (Shirley; Cameron; J. Amer. Chem. Soc.; 74; 1952; 664) as amine.

HPLC method C: elution at 7.85 min. LC-MS: Calc for MH$^+$: 312; Found: 312. $^1$H NMR (DMSO-d$_6$) δ 1.77 (m, 1H), 2.02 (m, 1H), 2.40–2.80 (m, 5H), 4.56 (ABX, 2H), 7.28 (s, 1H), 7.33 (m, 2H), 7.40 (s, 1H), 7.80 (d, 1H), 7.91 (d, 1H), 8.65 (m, 1H), 11.6 (s, 1H).

Microanalysis for C$_{17}$H$_{17}$N$_3$OS,H$_2$O: Calc: C: 61.98%; H: 5.81%; N: 12.76%. Found: C: 62.55%; H: 5.56%; N: 12.77%.

Example 15

4,5,6,7-Tetrahydro-1H-benzimidazole-5-carboxylic acid 3-trifluoromethylbenzylamide

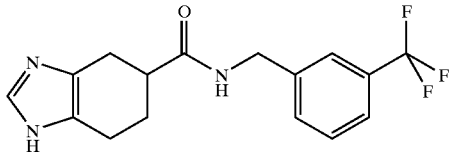

By a similar procedure as described in Example 1 the title compound was prepared. HPLC method B: elution at 4.56 min. LC-MS: Calc for MH$^+$: 324.3; Found: 324.2. $^1$H NMR (400 MHz, DMSO-d$_6$) δ 1.75 (m, 1H), 2.00 (m, 1H), 2.45–2.70 (m, 5H), 4.38 (ABX, 2H), 7.39 (s, 1H), 7.55–7.65 (m, 4H), 8.53 (m, 1H), 11.60 (br, 1H).

Example 16

Piperidine-1-carboxylic acid 4,5,6,7-tetrahydro-1H-benzimidazol-4-ylmethyl ester, oxalic acid salt

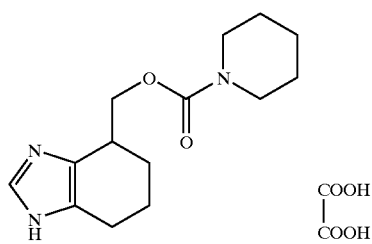

Step 1: 1-Triphenylmethyl-4,5,6,7-tetrahydro-1H-benzimidazole-4-carboxylic acid ethyl ester

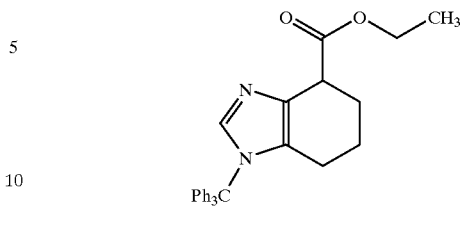

To a solution of 4,5,6,7-tetrahydro-1H-benzimidzole-4-carboxylic acid ethyl ester (18.9 g, 97 mmol, J. Am. Chem. Soc., 1996, 98, 984) in acetonitrile (250 ml) were added triethylamine (27 ml, 194 mmol) and a solution trityl chloride (40.6 g, 146 mmol) in acetonitrile (500 ml). The resulting mixture was stirred at 20° C. overnight. The mixture was concentrated under reduced pressure and the residue was redissolved in ethyl acetate, washed with water (2×) and brine (1×), and concentrated under reduced pressure. The residue was recrystallised from ethyl acetate/heptane, to yield 20.8 g (49%) of 1-triphenylmethyl-4,5,6,7-tetrahydro-1H-benzimidazole-4-carboxylic acid ethyl ester as a colourless solid. From the method liquid more product (10.3 g, 24%) was isolated by column chromatography (silica gel, gradient elution with heptane/ethyl acetate 9:1 to 1:1).

$^1$H NMR (300 MHz, CDCl$_3$): δ 1.29 (t, J=7 Hz, 3H), 1.30–1.50 (m, 2H), 1.58–1.73 (m, 2H), 1.75–2.02 (m, 2H), 3.73 (t, J=6 Hz, 1H), 4.19 (m, 2H), 7.13 (m, 6H), 7.25–7.36 (m, 10H).

Step 2: 4-Hydroxymethyl-1-triphenylmethyl-4,5,6,7-tetrahydro-1H-benzimidazole

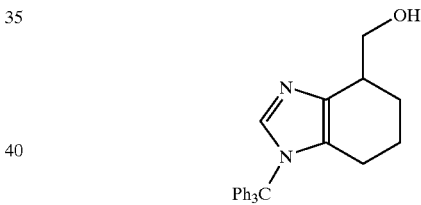

To a solution of 1-triphenylmethyl-4,5,6,7-tetrahydro-1H-benzimidazole-4-carboxylic acid ethyl ester (14.0 g, 32 mmol) in THF (100 ml) was added lithium aluminum hydride (24 ml, 1 mol/L in THF, 24 mmol). The mixture was stirred at 20° C. for 45 min, and water (3.5 ml) and sodium hydroxide (3.5 ml, 4 mol/L in water) were carefully added. Water (14 ml) and concentrated aqueous hydrochloric acid (1.13 ml) were added, and the mixture was filtered and concentrated under reduced pressure. The residue was re-dissolved in ethyl acetate (150 ml), dried (magnesium sulphate), filtered, and kept at 20° C. overnight. Filtration yielded 7.0 g (55%) of 4-hydroxymethyl-1-triphenylmethyl-4,5,6,7-tetrahydro-1H-benzimidazole as a colourless solid. Mp. 168–170° C. $^1$H NMR (400 MHz, CDCl$_3$): δ 1.08–1.19 (m, 1H), 1.28–1.50 (m, 2H), 1.54–1.66 (m, 2H), 1.72–1.80 (m, 1H), 2.91–3.00 (m, 1H), 3.59 (t, J=10 Hz, 1H), 3.72–3.81 (m, 1H), 4.62 (d, br, J=10 Hz, 1H), 7.13 (m, 6H), 7.27 (s, 1H), 7.33 (m, 9H).

Step 3:

To a solution of 4-hydroxymethyl-1-triphenylmethyl-4,5,6,7-tetrahydro-1H-benzimidazole (0.30 g, 0.76 mmol) in DCM (10 ml) were added pyridine (0.12 ml) and a solution of 4-nitrophenyl chloroformate (0.15 g, 0.76 mmol) in DCM (5 ml). The mixture was stirred at 20° C. for 2 hours, washed with water (2×30 ml), dried (magnesium sulphate), and concentrated under reduced pressure. The residue was dissolved in acetonitrile (10 ml) and piperidine (0.15 ml, 1.52 mmol) was added. The resulting mixture was kept at 20° C. for 48 hours, concentrated under reduced pressure, and the product was purified by column chromatography (silica gel, gradient elution with heptane/ethyl acetate 9:1 to 1:1). To the resulting product was added a mixture of glacial acetic acid (45 ml) and water (5 ml), and the resulting mixture was kept at 70° C. overnight. After concentration under reduced pressure, ethyl acetate and a solution of oxalic acid (0.10 g) in ethyl acetate (5 ml) were added. Filtration gave the title compound (70 mg, 26%) as a colourless solid. Mp. 132–135° C. $^1$H NMR (400 MHz, DMSO-$d_6$) δ 1.41 (s, br, 4H), 1.52 (m, 2H), 1.61–1.76 (m, 2H), 1.82–1.93 (m, 2H), 2.55 (s, br, 2H), 3.08 (m, 1H), 3.31 (m, 4H), 4.04 (m, 1H), 4.31 (dd, J=9 Hz, 6 Hz, 1H), 8.48 (s, br, 1H).

Example 17

N-Cyclohexyl-N-methyl Carbamic Acid 4,5,6,7-Tetrahydro-1H-benzimidazol-4-ylmethyl Ester, Oxalic Acid Salt

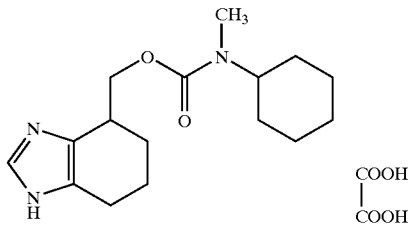

Using the procedure described in Example 16 and starting from 4-hydroxymethyl-1-triphenylmethyl-4,5,6,7-tetrahydro-1H-benzimidazole (0.30 g, 0.76 mmol) and N-cyclohexyl-N-methylamine (0.20 ml, 1.52 mmol) 97 mg (33%) of the title compound were obtained. $^1$H NMR (400 MHz, DMSO-$d_6$) δ 0.95–1.80 (m, 14H), 1.82–1.98 (m, 2H), 2.56 (s, br, 1H), 2.69 (s, br, 3H), 3.11 (s, br, 1H), 3.48 and 3.78 (2×s, br, each 0.5H), 4.06–4.21 (m, 1H), 4.29 (dd, J=3Hz, 9 Hz, 1H), 8.53 (s, br, 1H).

Example 18

N-Benzyl-N-methyl Carbamic Acid 4,5,6,7-Tetrahydro-1H-benzimidazol-4-ylmethyl Ester, Oxalic Acid Salt

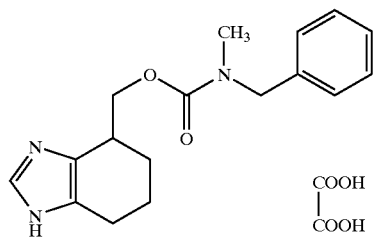

Using the procedure described in Example 16 and starting from 4-hydroxymethyl-1-triphenylmethyl-4,5,6,7-tetrahydro-1H-benzimidazole (0.30 g, 0.76 mmol) and N-benzyl-N-methylamine (0.20 ml, 1.52 mmol) 120 mg (41%) of the title compound was obtained. Mp. 110–112° C. $^1$H NMR (400 MHz, DMSO-$d_6$) δ 1.50–1.96 (m, 4H), 2.39–2.60 (m, 2H), 2.78 and 2.80 (2×s, br, 3H), 3.10 (s, br, 1H), 4.16 (s, br, 1H), 4.30 (s, br, 1H), 4.39 (s, br, 2H), 7.03–7.39 (m, 5H), 8.49 (s, 1H).

Example 19

N-Benzylcarbamic Acid 4,5,6,7-Tetrahydro-1H-benzimidazol-4-ylmethyl Ester

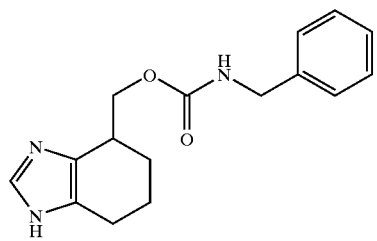

Using the procedure described in Example 16 and starting from 4-hydroxymethyl-1-triphenylmethyl-4,5,6,7-tetrahydro-1H-benzimidazole (0.25 g, 1.64 mmol) and benzylamine (0.50 ml, 3.9 mmol) 102 mg (22%) of the title compound was obtained. $^1$H NMR (400 MHz, DMSO-$d_6$) δ 1.53–1.18 (m, 2H), 1.83 (m, 2H), 2.44 (m, 2H), 2.89 (m, 1H), 3.80–3.95 (m, 1H), 4.19 (d, J=7 Hz, 2H), 4.20–4.40 (m, 1H), 7.25 (m, 3H), 7.31 (m, 2H), 7.41 (s, 1H), 7.68 (t, J=7 Hz, 1H), 11.60 (s, br, 1H).

Example 20

4,5,6,7-Tetrahydro-1H-benzimidazole-5-carboxylic Acid Bicyclo[2.2.1]hept-2-ylamide

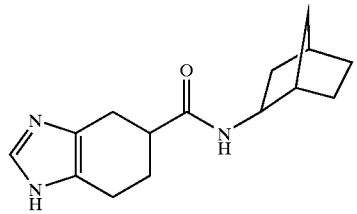

0.13 g (42%) of the title compound was prepared by a similar procedure as described in Example 1. HPLC method C: elution at 6.98 min. LC-MS: Calc for MH$^+$: 260; Found: 260. $^1$H NMR (CDCl$_3$): δ 1.20 (m, 5H), 1.50 (m, 2H), 1.82 (dd, 1H), 1.95 (m, 1H), 2.12 (m, 1H), 2.20 (m, 1H), 2.30 (m, 1H), 2.40–3.00 (m, 5H), 3.75 (m, 1H), 5.61 (d, 1H), 7.50 (s, 1H).

The title compound was transferred into its hydrochloride salt by lyophilization of 0.5 N hydrochloric acid (40 ml). Microanalysis for $C_{17}H_{17}N_3OS$, HCl, 3 $H_2O$: Calc: C: 51.50%; H: 8.07%; N: 12.01%. Found: C: 52.90%; H: 7.92%; N: 12.25%.

Example 21

4,5,6,7-Tetrahydro-1H-benzimidazole-5-carboxylic Acid N-methyl-N-(4-(trifluoromethyl)benzyl)amide

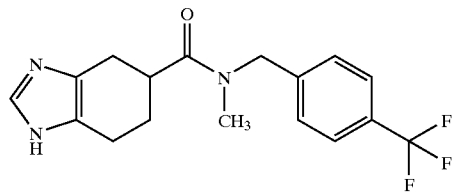

Step 1: N-Methyl-N-((4-Trifluoromethyl)benzyl)amine

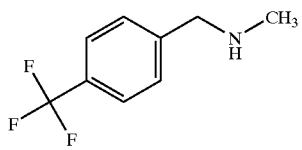

A solution of 4-(trifluoromethyl)benzyl bromide (7.0 g, 29 mmol) in DMF (100 ml) was added dropwise to a mixture of a 33% solution of methylamine in methanol and DMF (200 ml). The reaction mixture was stirred for 16 hours at room temperature. The solvent was removed in vacuo. The residue was dissolved in ethyl acetate (300 ml) and washed twice with a mixture of water and a saturated solution of sodium hydrogen carbonate in water (100 ml/200 ml). The aqueous phase was extracted with ethyl acetate (100 ml). The combined organic layers were dried over magnesium sulphate. The crude product was purified by flash chromatography on silica (60 g), using DCM/methanol/25% aqueous ammonia as eluent, to give 3.0 g of N-Methyl-N-((4-trifluoromethyl)benzyl)amine. $^1$H NMR (CDCl$_3$): δ 1.40 (s, 1H), 2.46 (s, 3H), 3.80 (s, 2H), 7.44 (d, 2H), 7.58 (d, 2H).

Step 2:

0.207 g (61%) of the title compound was prepared by a similar procedure as described in Example 1. HPLC method C: elution at 8.57 min. LC-MS: Calc for MH$^+$: 338; Found: 338. $^1$H NMR (CDCl$_3$): δ 2.10 (m, 2H), 2.75 (m, 3H), 3.00 (m, 2H), 3.00 and 3.05 (both s, together 1H), 4.70 (m, 2H), 7.30 and 7.38 (both d, together 2H), 7.48 and 7.50 (both s, together 1H), 7.60 and 7.65 (both d, together 2H).

The title compound was transferred into its hydrochloride salt by lyophilization of 0.5 N hydrochloric acid (40 ml). Microanalysis for C$_{17}$H$_{18}$F$_3$N$_3$O, HCl, H$_2$O: Calc: C: 52.11%; H: 5.40%; N: 11.24%. Found: C: 52.31%; H: 5.67%; N: 10.56%.

Example 22

4,5,6,7-Tetrahydro-1H-benzimidazole-5-carboxylic Acid N-(2-Chloro-6-phenoxy-benzyl)amide

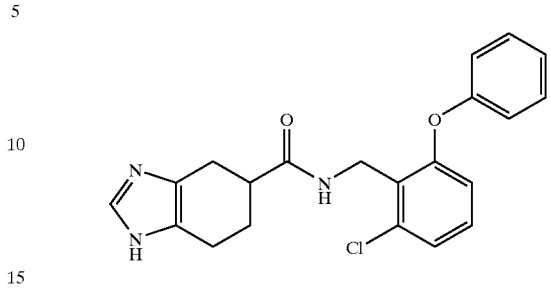

83 mg of the title compound was prepared from 4,5,6,7-tetrahydro-1H-benzimidazole-5-carboxylic acid and 2-chloro-6-phenoxybenzylamine by a similar procedure as described in Example 1. Mp. 197–199° C. LC-MS: Calc for MH$^+$: 382; Found: 382. Microanalysis for C$_{21}$H$_{20}$N$_3$ClO$_2$: Calc: C: 66.05%; H: 5.28%; N: 11.00%. Found: C: 65.91%; H: 5.45%; N: 10.97%.

Example 23

4,5,6,7-Tetrahydro-1H-benzimidazole-5-carboxylic Acid (4-Trifluoromethylcyclohexylmethyl)amide

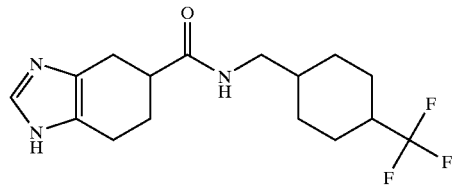

Step 1: 4-Trifluoromethylcyclohexanecarboxylic acid amide

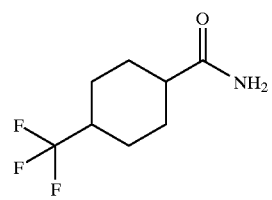

At 0° C. 1-(3-dimethylaminopropyl)-3-ethylcarbodiimide (2.90 g, 15.29 mmol) was added to a solution of 4-(trifluoromethyl)cyclohexanecarboxylic acid (3.0 g, 15.29 mmol) and 1-hydroxybenzotriazole (2.1 g, 15.29 mmol) in DMF (10 ml) and DCM (10 ml). The reaction mixture was stirred for 20 min at 0° C. A saturated solution of ammonia in methanol (17 ml) was added. The reaction mixture was stirred for 16 hours, while it was warming up to room temperature. It was diluted with ethyl acetate (100 ml) and washed with a 10% aqueous solution of sodium hydrogen sulphate (100 ml). The aqueous phase was extracted with ethyl acetate (2×80 ml). The combined organic layers were washed with a saturated aqueous solution of sodium hydrogen carbonate (100 ml) and dried over magnesium sulphate. The solvent was removed in vacuo. The crude product was purified by flash chromatography on silica, using DCM/methanol/25% aqueous ammonia (100:10:1) as eluent, to give 1.38 g of 4-trifluoromethylcyclohexanecarboxylic acid amide. ¹H NMR (CDCl₃): δ 1.20–1.90 (m, 6H); 2.01 (m, 4H); 2.51 (q, 1H); 5.50 (br, 2H).

Step 2: ((4-Trifluoromethylcyclohexyl)methyl)amine

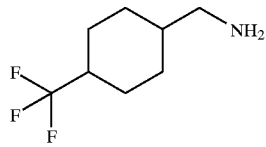

At 0° C. a solution of 4-trifluoromethylcyclohexanecarboxylic acid amide (1.38 g, 7.07 mmol) in THF (20 ml) was added to a suspension of sodium borohydride (0.64 g, 16.97 mmol) in THF (20 ml). A solution of iodine (1.79 g, 7.07 mmol) in THF (20 ml) was added dropwise. The reaction mixture was heated to reflux for 16 hours. It was cooled to 0° C. Methanol (40 ml) was added dropwise. The solvent was removed in vacuo. The residue was dissolved in tert-butyl methyl ether (100 ml) and a 20% aqueous solution of sodium hydroxide. The phases were separated. The aqueous phase was extracted with tert-butyl methyl ether (2×70 ml). The combined organic layers were dried over magnesium sulphate. The solvent was removed in vacuo. The crude product was purified by flash chromatography on silica (90 g), using DCM/methanol/25% aqueous ammonia (first 100:10:1, then 50:10:1) as eluent, to give 124 mg of ((4-trifluoromethylcyclohexyl)methyl) amine. MS: calc for [M+H]⁺: 182; Found: 182. ¹H NMR (CDCl₃): δ 0.8–2.30 (m, 12H), 2.40–2.90 (m, 2H).

Step 3:

120 mg of the title compound was prepared as described in Example 2 using ((4-trifluoromethylcyclohexyl)methyl) amine as the amine. HPLC method C: elution at 8.23 min. MS: calc for [M+H]⁺: 330; Found: 330. ¹H NMR (CDCl₃): δ 1.40–1.30 (m, 12H); 2.50–2.95 (m, 5H); 3.30 (m, 2H); 6.05 (t, 1H); 7.50 (s, 1H).

The title compound was transferred into its hydrochloric salt, by lyophilization with 0.5 M hydrochloric acid. Microanalysis for C₁₆H₂₂F₃N₃O, HCl, H₂O (419.89): Calc: C: 45.77%; H: 6.96%; N: 10.01%; Found: C: 46.35%; H: 6.78%; N: 10.27%.

Example 24

4,5,6,7-Tetrahydro-1H-benzimidazole-5-carboxylic Acid 4-Methanesulfonyl-benzylamide

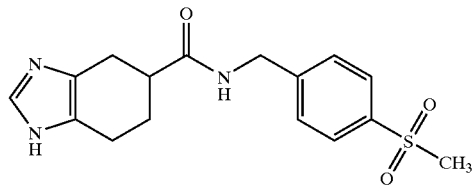

At 0° C. 1-(3-dimethylaminopropyl)-3-ethylcarbodiimide (0.23 g, 1.184 mmol) was added to a solution of 4,5,6,7-tetrahydro-1H-benzimidazole-5-carboxylic acid (024 g, 1.184 mmol) and 1-hydroxybenzotriazole (0.16 g, 1.184 mmol) in DMF (5 ml). The reaction mixture was stirred for 20 min at 0° C. 4-(Methylsulfonyl)benzylamine (0.26 g, 1.184 mmol) and ethyl-diisopropylamine (0.90 ml, 5.211 mmol) were added successively. The reaction mixture was stirred for 16 hours, while it was warming up to room temperature. The solvent was removed in vacuo. The crude product was purified filtered through SepPack® (5 g), using 1% TFA in water/acetonitrile (80:40) as eluent. The resulting mixture was purified by flash chromatography on silica (40 g), using DCM/methanol/25% aqueous ammonia (50:10:1) as eluent, to give 0.32 g of the title compound. HPLC method C: elution at 4.39 min. MS: calc for [M+H]⁺ 334; Found: 334. ¹H NMR (DMSO-d₆): δ 1.75 (m, 1H); 2.05 (m, 1H); 2.45–2.70 (m, 5H); 3.20 (s, 3H); 4.40 (ABX, 2H); 7.42 (s, 1H); 7.52 (d, 2H); 7.90 (d, 2H); 8.57 (t, 1H).

The title compound was transferred into its hydrochloric salt, by lyophilization with 0.5 M hydrochloric acid (40 ml).

Example 25

4,5,6,7-Tetrahydro-1H-benzimidazole-5-carboxylic Acid N-Methyl-N-((4'-(trifluoromethyl)biphenyl-2-yl)methyl)amide

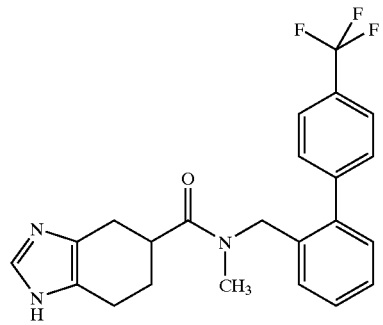

Step 1: 4'-(Trifluoromethyl)biphenyl-2-carboxylic acid methylamide

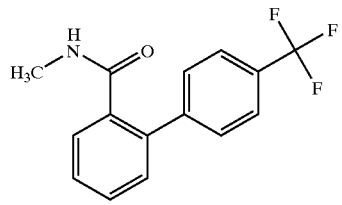

At 0° C. 1-(3-dimethylaminopropyl)-3-ethylcarbodiimide (7.2 g, 37.57 mmol) was added to a solution of 4'-(trifluoromethyl)-2-biphenylcarboxylic acid (10.0 g, 37.57 mmol) and 1-hydroxybenzotriazole (5.1 g, 37.57 mmol) in DMF (50 ml) and DCM (20 ml). The reaction mixture was stirred for 20 min at 0° C. A 8.3 M solution of methylamine in ethanol (94 ml, 751 mmol) was added. The reaction mixture was stirred for 16 hours, while it was warming up to room temperature. It was diluted with ethyl acetate (100 ml) and washed with a 10% aqueous solution of sodium hydrogen sulphate (100 ml). The aqueous phase was extracted with ethyl acetate (3×70 ml). The combined organic layers were washed with a saturated aqueous solution of sodium hydrogen carbonate (100 ml) and dried over magnesium sulphate. The solvent was removed in vacuo. The crude product was purified by flash chromatography on silica (200 g), using ethyl acetate/heptane (2:1) as eluent, to give 8.50 g of 4'-(trifluoromethyl)biphenyl-2-carboxylic acid methylamide. ¹H NMR (CDCl₃): δ 2.75 (d, 3H); 5.80 (br, 1H); 7.40 (d, 1H); 7.50 (m, 2H); 7.55 (d, 2H), 7.65 (d, 1H); 7.70 (d, 2H).

Step 2: N-Methyl-N-((4'-trifluoromethyl)biphenyl-2-yl)methyl)amine

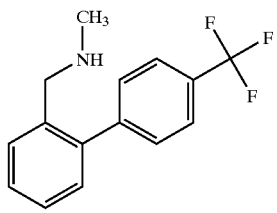

At 0° C. a solution of 4'-trifluoromethyl)biphenyl-2-carboxylic acid methylamide (8.50 g, 36.44 mmol) in THF (100 ml) was added to a suspension of sodium borohydride (2.8 g, 73.05 mmol) in THF (50 ml). The reaction mixture was stirred for 20 min at 0° C. A solution of iodine (7.70 g, 36.44 mmol) in THF (100 ml) was added dropwise. The reaction mixture was heated to reflux for 16 hours. It was cooled to 0° C. Methanol (200 ml) was added dropwise. The solvent was removed in vacuo. The residue was dissolved in tert-butyl methyl ether (150 ml) and a 20% aqueous solution of sodium hydroxide (150 ml). The phases were separated. The aqueous phase was extracted with tert-butyl methyl ether (2×80 ml). The combined organic layers were dried over magnesium sulphate. The solvent was removed in vacuo. The crude product was purified by flash chromatography on silica (400 g) using DCM/methanol/25% aqueous ammonia (100:10:1) as eluent, to give 2.35 g of N-methyl-N-((4'-trifluoromethyl)biphenyl-2-yl)methyl)amine. $^1$H NMR (CDCl$_3$): δ 2.37 (s, 3H), 3.65 (s, 2H); 7.22 (d, 1H); 7.35 (m, 2H); 7.50 (m, 3H); 7.70 (d, 2H).

Step 3:

285 mg of the title compound was prepared as described in Example 2, using N-methyl-N-((4'-trifluoromethyl)biphenyl-2-yl)methyl)amine. HPLC method C: elution at 10.20 min. MS: calc for [M+H]$^+$ 414; Found: 414. $^1$H NMR (CDCl$_3$): δ 1.95 (m, 2H); 2.40–3.00 (m, 5H); 2.85 and 2.93 (both s, together 3H); 4.50 and 4.65 (both AB, together 2H); 7.10–7.60 (m,7H); 7.70 (d, 2H).

The title compound was transferred into its hydrochloric salt, by lyophilization with 0.5 M hydrochloric acid (40 ml).

Example 26

4,5,6,7-Tetrahydro-1H-benzimidazole-5-carboxylic Acid (3-Chloro-4-trifluoro-methylbenzyl)amide

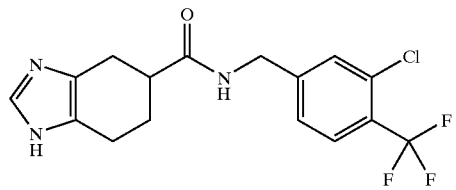

Step 1: 4-Bromomethyl-2-chloro-1-trifluoromethylbenzene

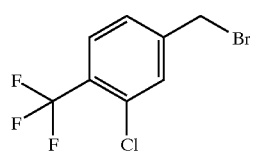

A mixture of 2-chloro-4-methyl-1-trifluoromethylbenzene (10.0 g; 51 mmol), N-bromosuccinimide (8.69 g, 49 mmol), benzoyl peroxide (0.37 g, 1.5 mmol) in tetrachloromethane (100 ml) was heated to reflux for 2 hours. Another portion of benzoyl peroxide (1.0 g, 4.1 mmol) was added. The mixture was heated to reflux for another 0.5 hours. The reaction mixture was stirred at room temperature for 16 hours. The solid was removed by filtration. The solvent was removed in vacuo. The crude product was purified by flash chromatography on silica (200 g), using ethyl acetate/heptane (1:4) as eluent, to give 12.5 g of 4-bromomethyl-2-chloro-1-trifluoromethylbenzene. $^1$H NMR (CDCl$_3$): δ 4.45 (s, 2H); 7.40 (d, 1H); 7.55 (s, 1H); 7.67 (d, 1H).

Step 2: 3-Chloro-4-(trifluoromethyl)benzylamine

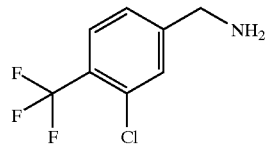

A solution of 4-bromomethyl-2-chloro-1-trifluoromethylbenzene (3.0 g, 11 mmol) in DMF (25 ml) was added dropwise to a mixture of 25% aqueous ammonia (50 ml) and DMF (25 ml). The reaction mixture was stirred at room temperature for 60 hours. The solvent was removed in vacuo. The residue was dissolved in ethyl acetate (100 ml) and washed with a saturated aqueous solution of sodium hydrogen carbonate (100 ml). The aqueous phase was extracted with ethyl acetate (2×60 ml). The combined organic layers were dried over magnesium sulphate. The solvent was removed in vacuo. The crude product was purified by flash chromatography on silica (90 g), using first ethyl acetate/heptane (1:3) together with 3% triethylamine and subsequently DCM/methanol/25% aqueous ammonia as eluent, to give 250 mg of 3-chloro-4-(trifluoromethyl)benzylamine. $^1$H NMR (CDCl$_3$): δ 1.85 (br, 2H); 3.95 (s, 2H); 7.25 (m, 1H); 7.45 (s, 1H); 7.60 (d, 1H).

Step 3:

234 mg of the title compound were prepared as described in Example 2, using 250 mg of 3-chloro-4-(trifluoromethyl)benzylamine. HPLC method C: elution at 8.88 min. MS: calc for [M+H]$^+$: 358; Found: 358. $^1$H NMR (DMSO-d$_6$): δ 1.75 (m, 1H); 2.00 (m, 1H); 2.60 (m, 4H); 3.15 (m, 1H); 4.40 (s, 2H); 7.40 (m, 2H); 7.60 (s, 1H); 7.85 (d, 1H); 8.55 (br, 1H); 11.6 (br, 1H).

Example 27

Preparation of an Array of Ketones

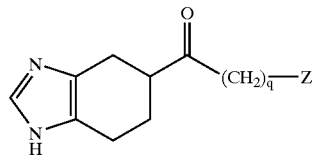

Step 1: 4,5,6,7-Tetrahydro-1H-benzimidazole-5-carboxylic acid methyl ester

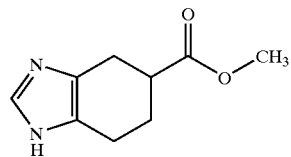

In a 350 ml steel autoclave with teflon insert was placed 1H-benzimidazole-5-carboxylic acid (10 g, 61.7 mmol), 50% aqueous acetic acid (160 ml), 35% aqueous HCl solution (7 ml) and 6 g Rh/C (5%). The reaction mixture was hydrogenated at 60 bar $H_2$ at 120° C. for 24 hours. After cooling and filtration through Celite, the filtrate was evaporated to dryness and the residue further dried under reduced pressure. The residue was mixed with methanol (200 ml) and (9 ml, 0.123 mol) thionyl chloride and heated at 80° C. for 2 hours. After cooling, the reaction mixture was evaporated to dryness and the white solid further dried under reduced pressure to yield 13.6 g (92%) of 4,5,6,7-tetrahydro-1H-benzimidazole-5-carboxylic acid methyl ester hydrochloride. The hydrochloride was treated with saturated sodium hydrogen carbonate solution (300 ml) and extracted with DCM (3×300 ml) to obtain 10.8 g (81%) of 4,5,6,7-tetrahydro-1H-benzimidazole-5-carboxylic acid methyl ester as a white solid.

Step 2: 4,5,6,7-Tetrahydro-1H-benzimidazole-5-carboxylic acid N-methoxy-N-methylamide

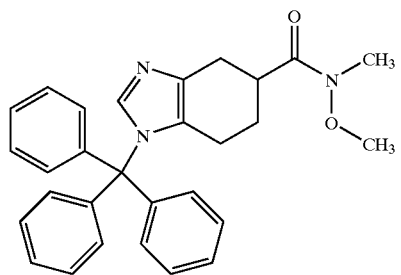

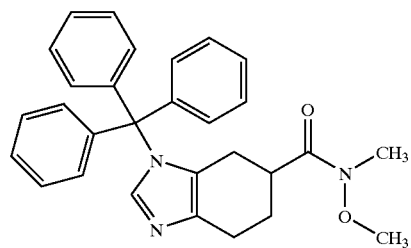

To a stirred suspension of 4,5,6,7-tetrahydro-1H-benzimidazole-5-carboxylic acid methyl ester (5 g, 27.3 mmol) in $CH_3CN$ (120 ml) and triethylamine (7.74 ml, 2 equiv.) was added under $N_2$, triphenylmethtyl chloride (10.1 g, 32.8 mmol) in portions. The reaction mixture was stirred for 4 hours at room temperature, evaporated and extracted with ethyl acetate (200 ml) and water (150 ml), the organic layer washed with saturated brine, dried (magnesium sulphate), evaporated and the residue chromatographed on silica with ethyl acetate/hexane (6:1) to yield 10.8 g (92%) of the protected methyl ester as a white solid. This solid was dissolved in THF (80 ml) and water (25 ml) and LiOH× $1H_2O$ (5.37 g, 5 equiv.) was added in portions at room temperature. The reaction mixture was stirred overnight at room temperature, acidified with 10% $NaH_2PO_4$ solution to pH 6 and extracted with ethyl acetate (2×150 ml). The organic layer was dried (magnesium sulphate) and evaporated to yield 9.3 g (89%) of the intermediate acid as a white solid. This acid (4.5 g, 11.0 mmol) was dissolved in DCM (50 ml) and cooled to 4° C., followed by addition of N-(3-dimethylaminopropyl)-N'-ethyl-carbodiimide hydrochloride (2.23 g, 12.1 mmol), N-methoxy-N-methylamine hydrochloride (1.59 g, 16.5 mmol) and Hünig's base (4.8 ml, 27.5 mmol). The reaction mixture was stirred for 30 min. at 4° C. and overnight at room temperature, followed by extraction with water (100 ml) and ethyl acetate (2×150 ml). The organic layer was dried (magnesium sulphate), evaporated and the residue chromatographed on $SiO_2$ with DCM/methanol (20:1→10:1) to yield 4.2 g (84%) of 4,5,6,7-tetrahydro-1H-benzimidazole-5-carboxylic acid N-methoxy-N-methylamide as a white amorphous solid (a 7:3 mixture of N-triphenylmethyl isomers). $^1$H NMR (300 MHz, $CDCl_3$) δ main isomer: 7.35–7.27 (m, 10H); 7.17–7.12 (m, 6H); 3.67 (s, 3H); 3.19 (s, 3H); 3.0–2.6 (m, 3H); 1.85–1.6 (m, 4H); minor isomer: 7.35–727 (m, 10H); 7.17–7.12 (m, 6H); 3.45 (s, 3H); 3.04 (s, 3H); 3.0–2.6 (m, 3H); 1.85–1.6 (m, 4H).

Step 3a: Preparation of ketones from Z—$(CH_2)_q$—Li compounds:

To 0.3 mmol of the corresponding Z—$(CH_2)_q$ bromide in THF (1 ml) was added at −78° C. tert-BuLi solution (0.44 ml, 0.66 mmol, 1.5 M in pentane) and the mixture was stirred for 1 hour at −78° C. This solution was added to a pre-cooled (4° C.) solution of 4,5,6,7-tetrahydro-1H-benzimidazole-5-carboxylic acid N-methoxy-N-methylamide (0.25 mmol) in THF (1 ml). The reaction mixture was stirred for 1 hour at 4° C. and then poured onto 10% $NaH_2PO_4$ solution and ethyl acetate. The organic layer was washed with saturated sodium hydrogen carbonate solution, dried (magnesium sulphate), evaporated and the residue chromatographed on $SiO_2$. The residue was deprotected using 2 N HCl solution in ethanol at 80° C.

Step 3b: Preparation of ketones from Grignard reagents, Z—$(CH_2)_q$—Mg—Hal 0.75 mmol of the corresponding Grignard solution was freshly prepared and added to a solution of 4,5,6,7-tetrahydro-1H-benzimidazole-5-carboxylic acid N-methoxy-N-methyl-amide (0.25 mmol) in THF (1 ml) between room temperature and 50° C. Work-up and deprotection were performed similarly as described above in Step 3a.

The following examples were prepared. The molecular weights of the examples were all confirmed by MS:

| Example | Name/Structure | Purity (%) (HPLC/UV) | MW |
|---|---|---|---|
| 27-001 | Isobutyl-(4,5,6,7-tetrahydro-1H-benzimidazol-5-yl)methanone 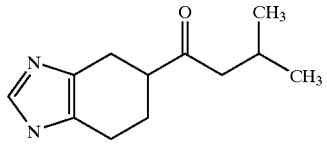 | 90 | 206.3 |
| 27-002 | 4-Phenoxyphenyl-(4,5,6,7-tetrahydro-1H--benzimidazol-5-yl)methanone 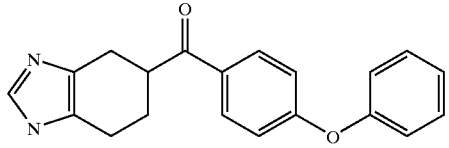 | 91 | 318.4 |
| 27-003 | Phenyl-(4,5,6,7-tetrahydro-1H-benzimidazol-5-yl)methanone 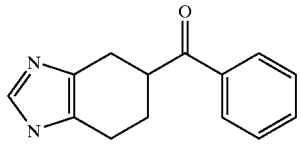 | 97 | 226.3 |
| 27-004 | Benzyl-(4,5,6,7-tetrahydro-1H-benzimidazol-5-yl)methanone 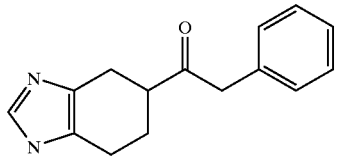 | 90 | 240.3 |
| 27-005 | (5-Methyl-2-pyridyl)-(4,5,6,7-tetrahydro-1H--benzimidazol-5-yl)methanone 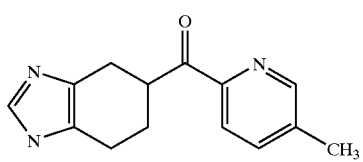 | 90 | 241.3 |
| 27-006 | (Cyclohexylmethyl)-(4,5,6,7-tetrahydro-1H--benzimidazol-5-yl)methanone 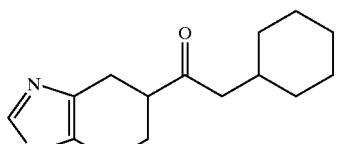 | 92 | 246.4 |
| 27-007 | 4-Methoxyphenyl-(4,5,6,7-tetrahydro-1H-benzimidazol-5-yl)methanone 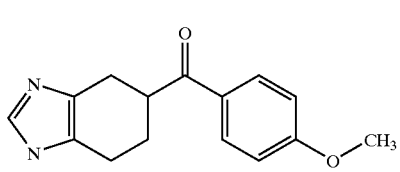 | 95 | 256.3 |

| Example | Name/Structure | Purity (%) (HPLC/UV) | MW |
|---|---|---|---|
| 27-008 | 4-Dimethylaminophenyl-(4,5,6,7-tetrahydro-1H-benzimidazol-5-yl)methanone 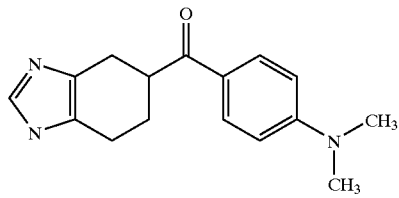 | 83 | 269.3 |
| 27-009 | 1-Naphthyl-(4,5,6,7-tetrahydro-1H-benzimidazol-5-yl)methanone 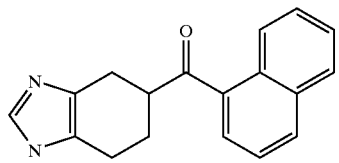 | 81 | 276.3 |
| 27-010 | 2-Naphthyl-(4,5,6,7-tetrahydro-1H-benzimidazol-5-yl)methanone 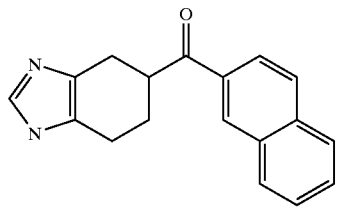 | 98 | 276.3 |
| 27-011 | 4-tert-Butylphenyl-(4,5,6,7-tetrahydro-1H-benzimidazol-5-yl)methanone 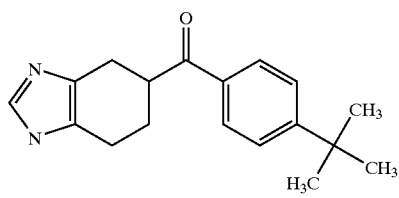 | 99 | 282.4 |
| 27-012 | Cyclopentyl-(4,5,6,7-tetrahydro-1H-benzimidazol-5-yl)methanone 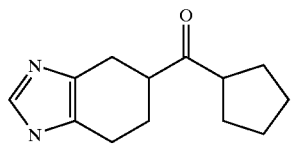 | 95 | 218.3 |
| 27-013 | 2-Thiazolyl-(4,5,6,7-tetrahydro-1H-benzimidazol-5-yl)methanone 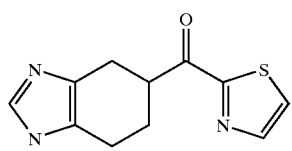 | 90 | 233.3 |

| Example | Name/Structure | Purity (%) (HPLC/UV) | MW |
|---|---|---|---|
| 27-014 | 4-Fluorophenyl-(4,5,6,7-tetrahydro-1H-benzimidazol-5-yl)methanone 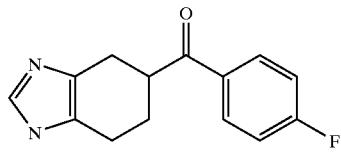 | 98 | 244.3 |
| 27-015 | (5-Methyl-2-thienyl)-(4,5,6,7-tetrahydro-1H-benzimidazol-5-yl)methanone 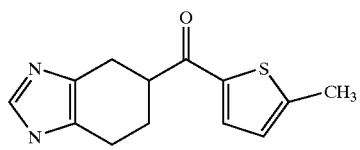 | 75 | 246.3 |
| 27-016 | (4-Methyl-3-thienyl)-(4,5,6,7-tetrahydro-1H-benzimidazol-5-yl)methanone 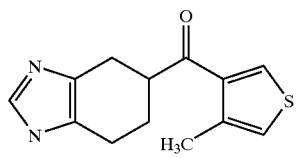 | 90 | 246.3 |
| 27-017 | (2-Phenylethyl)-(4,5,6,7-tetrahydro-1H-benzimidazol-5-yl)methanone 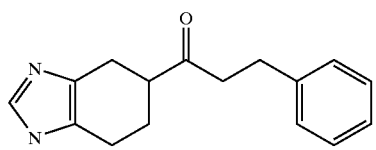 | 90 | 254.3 |
| 27-018 | 4-Chlorophenyl-(4,5,6,7-tetrahydro-1H-benzimidazol-5-yl)methanone 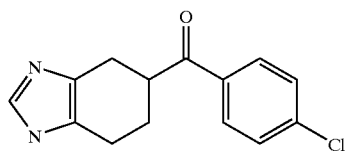 | 98 | 260.7 |
| 27-019 | Benzofuran-5-yl-(4,5,6,7-tetrahydro-1H-benzimidazol-5-yl)methanone 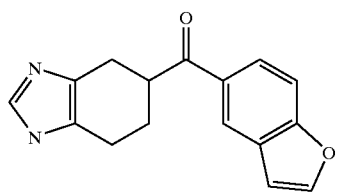 | 85 | 266.3 |

| Example | Name/Structure | Purity (%) (HPLC/UV) | MW |
|---|---|---|---|
| 27-020 | Benzo[1,3]dioxol-5-yl-(4,5,6,7-tetrahydro-1H-benzimidazol-5-yl)methanone | 83 | 270.3 |
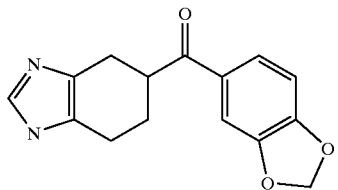
| | | | |
|---|---|---|---|
| 27-021 | (4-(1-Hydroxyethyl)phenyl)-(4,5,6,7-tetra-hydro-1H-benzimidazol-5-yl)methanone | 99 | 270.3 |
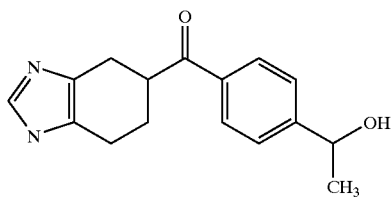
| | | | |
|---|---|---|---|
| 27-022 | Quinolin-3-yl-(4,5,6,7-tetrahydro-1H-benz-imidazol-5-yl)methanone | 96 | 277.3 |
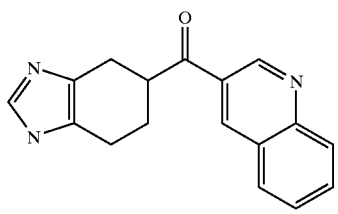
| | | | |
|---|---|---|---|
| 27-023 | 4-Trifluoromethylphenyl-(4,5,6,7-tetrahydro-1H-benzimidazol-5-yl)methanone | 90 | 294.3 |
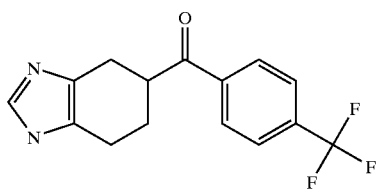
| | | | |
|---|---|---|---|
| 27-024 | 4-Methylphenyl-(4,5,6,7-tetrahydro-1H-benzimidazol-5-yl)methanone | 95 | 240.3 |
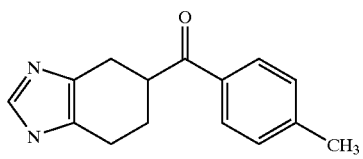

-continued

| Example | Name/Structure | Purity (%) (HPLC/UV) | MW |
|---|---|---|---|
| 27-025 | 4-Ethylphenyl-(4,5,6,7-tetrahydro-1H-benz-imidazol-5-yl)methanone 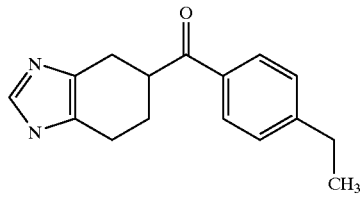 | 96 | 254.3 |
| 27-026 | 4-Ethoxyphenyl-(4,5,6,7-tetrahydro-1H-benzimidazol-5-yl)methanone 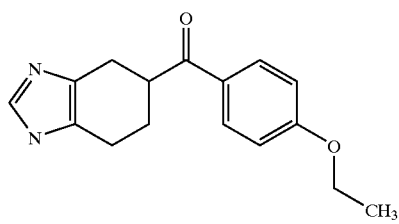 | 90 | 270.3 |
| 27-027 | 4-(Methylsulfanyl)phenyl-(4,5,6,7-tetrahydro-1H-benzimidazol-5-yl)methanone 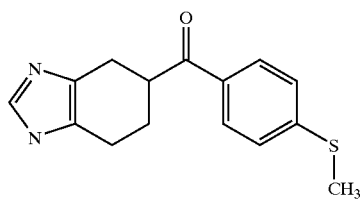 | 85 | 272.4 |
| 27-028 | 6-Methoxynaphthalen-2-yl-(4,5,6,7-tetra-hydro-1H-benzimidazol-5-yl)methanone 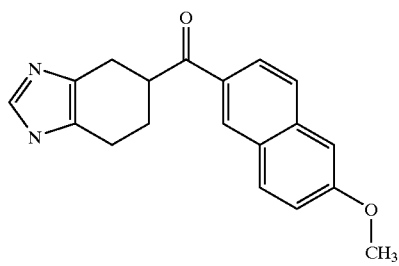 | 99 | 306.4 |
| 27-029 | (5-Chloro-3-methylbenzo[b]thiophen-2-yl)-(4,5,6,7-tetrahydro-1H-benzimidazol-5-yl)-methanone 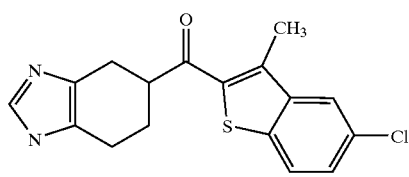 | 96 | 330.8 |

-continued

| Example | Name/Structure | Purity (%) (HPLC/UV) | MW |
|---|---|---|---|
| 27-030 | (4-(2-Hydroxyethyloxy)phenyl)-(4,5,6,7-tetrahydro-1H-benzimidazol-5-yl)methanone 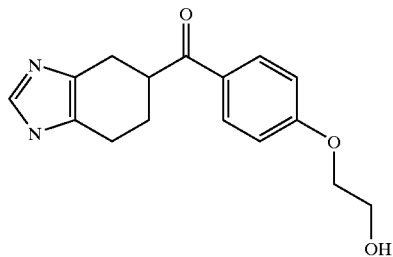 | 99 | 286.3 |

Example 28
Solid Phase Synthesis of Carboxamides

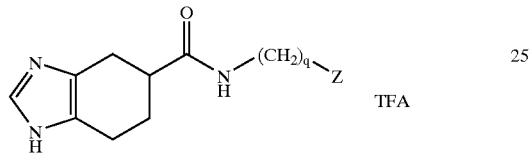

An array of the four compounds listed below was prepared by a similar procedure as described in Example 4.

| Example | Name/Structure | Yield (mg) | MH+ (calc) | MH+ (found) |
|---|---|---|---|---|
| 28-001 | 4,5,6,7-Tetrahydro-1H-benzimidazole-5-carboxylic acid (2,2-diphenylethyl)amide 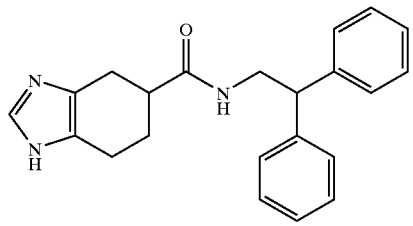 | 33 | 346.5 | 346.2 |
| 28-002 | 4,5,6,7-Tetrahydro-1H-benzimidazole-5-carboxylic acid [2-(3,4-dichlorophenyl)ethyl]amide 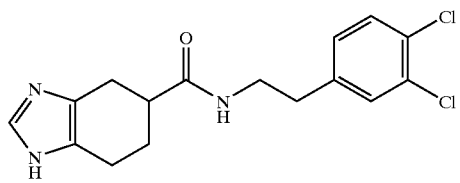 | 42 | 339.2 | 338.0 |

-continued

| Example | Name/Structure | Yield (mg) | MH+ (calc) | MH+ (found) |
|---------|----------------|------------|------------|-------------|
| 28-003 | 4,5,6,7-Tetrahydro-1H-benz-imidazole-5-carboxylic acid [2-(4-chlorophenyl)ethyl]amide | 37 | 304.8 | 304.4 |
| 28-004 | 4,5,6,7-Tetrahydro-1H-benz-imidazole-5-carboxylic acid (thiophen-2-ylmethyl)amide | 38 | 262.4 | 262.4 |

Example 29

Array Synthesis of Carboxamides

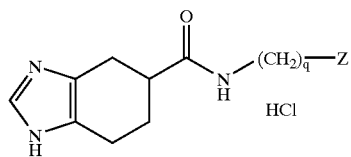

To each reactor in an array of four, equimolar amounts (60.2 μmol) of 4,5,6,7-tetrahydro-1H-benzimidazole-5-carboxylic acid, HOAt, DIC and a primary amine were mixed in DMA (2 ml) and the array was shaken overnight. The volume of each reactor was reduced to approximately 1/3 in vacuo at 60° C. and ethyl acetate (2.5 ml), $H_2O$ (5 ml) and brine (0.5 ml) were added to each reactor and the array was shaken vigorously. Additional ethyl acetate (2.5 ml) and $H_2O$ (2.5 ml) were added to each reactor and the array was shaken vigorously. From each reactor the aqueous phase was removed and the residue was washed with a 1% $NaHCO_3$ solution (2×5 ml). For each reactor the organic phase was transferred to a tube and HCl in ethyl acetate was added. The oily precipitate was isolated and dried in vacuo and the residue was stripped with acetone.

| Example | Name/Structure | MH+ (calc) | MH+ (found) |
|---------|----------------|------------|-------------|
| 29-001 | 4,5,6,7-Tetrahydro-1H-benz-imidazole-5-carboxylic acid (4-tert-butylcyclohexyl)amide | 304.5 | 304.4 |

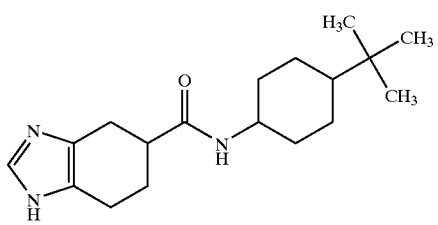

-continued

| Example | Name/Structure | MH+ (calc) | MH+ (found) |
|---|---|---|---|
| 29-002 | 4,5,6,7-Tetrahydro-1H-benzimidazole-5-carboxylic acid 3-fluorobenzylamide | 274.3 | 274.4 |
| 29-003 | 4,5,6,7-Tetrahydro-1H-benzimidazole-5-carboxylic acid (3,3-diphenylpropyl)amide | 360.5 | 360.0 |
| 29-004 | 4,5,6,7-Tetrahydro-1H-benzimidazole-5-carboxylic acid 4-tert-butylbenzylamide | 312.4 | 312.2 |

Example 30

4,5,6,7-Tetrahydro-1H-benzimidazole-5-carboxylic Acid (3-Phenylpropyl)amide

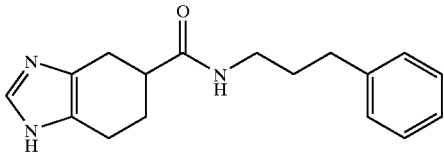

The title compound was prepared by a similar procedure as described in Example 4 from 100 mg of 2-formyl-5-methoxyphenoxyethylpolystyrene (0.55 mmol/g) resin, 4,5,6,7-tetrahydro-1H-benzimidazole-5-carboxylic acid (111 mg, 0.55 mmol) and 3-phenylpropylamine (74.4 mg, 0.55 mmol). LC-MS: Calc for MH+: 284.4; Found: 283.8.

Example 31

4,5,6,7-Tetrahydro-1H-benzimidazole-5-carboxylic Acid 2-Fluoro-6-(4-methoxyphenoxy)benzylamide, Hydrochloride

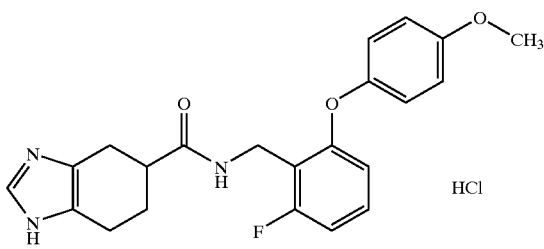

134 mg (43%) of the title compound was prepared from 4,5,6,7-tetrahydro-1H-benzimidazole-5-carboxylic acid and 2-fluoro-6-(4-methoxyphenoxy)benzylamine by a similar procedure as described in Example 1. HPLC method C: elution at 8.99 min. Microanalysis for $C_{22}H_{22}FN_3O_3$, HCl, 1.5 $H_2O$: Calc: C: 57.58%; H: 5.71%; N: 9.16%. Found: C: 57.79%; H: 5.75%; N: 9.35%.

Example 32

5-Cyclohexylpentanoic Acid (4,5,6,7-Tetrahydro-1H-benzimidazol-5-yl)amide, Hydrochloride

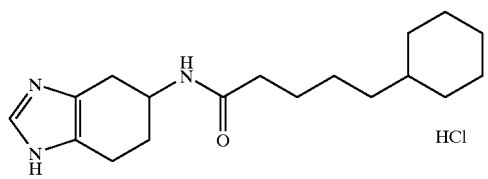

Step 1: 5-Amino-4,5,6,7-tetrahydro-1H-benzimidazole, Dihydrochloride Salt

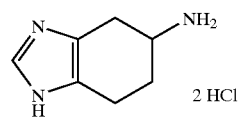

A solution of 5-nitrobenzimidazole (25 g, 150 mmol) in 1 N hydrochloric acid (100 ml) and $H_2O$ (100 ml) was hydrogenated at 110 bar and room temperature in the presence of 10% palladium on carbon (5 g) for 6 days. The mixture was filtered and the solvent was evaporated. The residue was stirred with ethanol (100 ml) and the solid was isolated and dried. This afforded 21 g of partly hydrogenated product that was dissolved in $H_2O$ (150 ml) and hydrogenated at 110 bar and 75° C. in the presence of 10% palladium on carbon (4 g) for 6 days. The mixture was cooled, filtered and the solvent was evaporated. The residue was stirred with ethanol (100 ml) and the solid was isolated and dried. This afforded 17.5 g (56%) of crude 5-amino-4,5,6,7-tetrahydro-1H-benzimidazole, dihydrochloride. $^1$H NMR (400 MHz, DMSO-$d_6$) δ 1.90–2.03 (m, 1H), 2.12–2.22 (m, 1H), 2.65–2.85 (m, 3H), 3.09 (dd, 1H), 3.50–3.63 (m, 1H), 8.63 (brs, 3H), 8.95 (s, 1H), 14.55 (brs, 2H).

Step 2:

To a mixture of 5-amino-4,5,6,7-tetrahydro-1H-benzimidazole, dihydrochloride (420 mg, 2.0 mmol) and DMA (10 ml), 5.4 M NaOMe in MeOH (0.74 ml, 4.0 mmol) was added, triethylamine (0.276 ml, 2 mmol) was added followed by dropwise addition of 5-cyclohexyl-pentanoic acid chloride (609 mg, 3.0 mmol). When addition was complete the mixture was stirred at ambient temperature for 30 min and then heated at 80° C. for 1 hour and finally allowed to cool to ambient temperature within 1 hour. The volatiles were evaporated and the residue was stirred vigorously with a mixture of $H_2O$ (100 ml), 1 N hydrochloric acid (10 ml) and diethyl ether (50 ml). The phases were separated and the aqueous phase was washed with diethyl ether (2×50 ml) and then made alkaline to pH 10–11 with 4 N sodium hydroxide. The alkaline mixture was extracted with ethyl acetate (2×50 ml) and the organic extracts were evaporated in vacuo. The residue was dissolved in 1 N hydrochloric acid and evaporated to dryness. The residue was re-evaporated with acetone to give 260 mg (38%) of the title compound. $^1$H NMR (400 MHz, DMSO-$d_6$) δ 0.75–0.90 (m, 2H), 1.05–1.28 (m, 8H), 1.45 (p, 2H), 1.55–1.70 (m, 5H), 1.72–1.93 (m, 2H), 2.06 (t, 2H), 2.47 (dd, 1H), 2.60–2.74 (m, 2H), 2.88 (dd, 1H), 4.03–4.13 (m, 1H), 7.97 (d, 1H), 8.90 (s, 1H), 14.3 (brs, 2H).

Example 33

N-(4,5,6,7-Tetrahydro-1H-benzimidazol-5-yl)-2-(4-trifluoromethoxyphenyl)acetamide, Hydrochloride

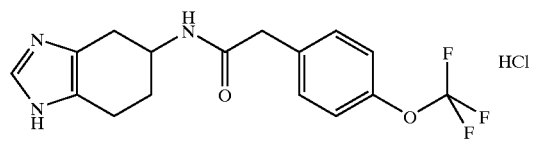

By a similar procedure as described in Example 32 the title compound was prepared. $^1$H NMR (400 MHz, DMSO-$d_6$) δ 1.75–1.95 (m, 2H), 2.54 (dd, 1H), 2.60–2.76 (m, 2H), 2.90 (dd, 1H), 3.51 (s, 2H), 4.02–4.12 (m, 1H), 7.29 (d, 2H), 7.39 (d, 2H), 8.56 (d, 1H), 8.91 (s, 1H), 14.6 (brs, 2H).

Example 34

3-Cyclohexyl-N-(4,5,6,7-tetrahydro-1H-benzimidazol-5-yl)propionamide, Hydrochloride

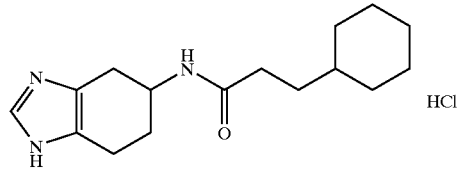

By a similar procedure as described in Example 32 the title compound was prepared. $^1$H NMR (400 MHz, DMSO-$d_6$) δ 0.75–0.90 (m, 2H), 1.05–1.25 (m, 4H), 1.39 (q, 2H), 1.55–1.70 (m, 5H), 1.72–1.92 (m, 2H), 2.08 (t, 2H), 2.42–2.52 (m, 1H), 2.58–2.73 (m, 2H), 2.86 (dd, 1H), 4.02–4.12 (m, 1H), 8.00 (d, 1H), 8.90 (s, 1H), 14.4 (brs, 2H).

Example 35

2-(4-Chlorophenyl)-N-(4,5,6,7-tetrahydro-1H-benzimidazol-5-yl)acetamide, Hydrochloride

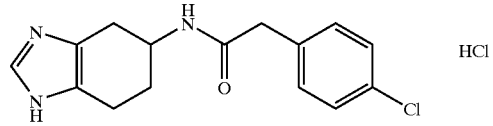

By a similar procedure as described in Example 32 the title compound was prepared. Mp. 222–224° C. HPLC method C: elution at 7.24 min. Microanalysis for $C_{15}H_{18}N_3ClO,HCl$: Calc: C: 55.23%; H: 5.25%; N: 12.88%. Found: C: 55.32%; H: 5.52%; N: 12.77%.

Example 36

N-(4,5,6,7-Tetrahydro-1H-benzimidazol-5-yl)-4-trifluoromethoxybenzamide, Hydrochloride

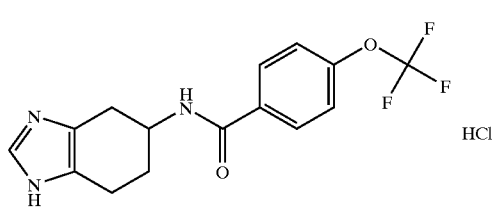

By a similar procedure as described in Example 32 the title compound was prepared. HPLC method C: elution at 8.20 min. $^1$H NMR (400 MHz, DMSO-$d_6$) δ 1.90–2.08 (m, 2H), 2.65–2.80 (m, 3H), 3.00 (dd, 1H), 4.25–4.35 (m, 1H), 7.46 (d, 2H), 8.03 (d, 2H), 8.76 (d, 1H), 8.93 (s, 1H), 14.5 (brs, 2H).

Example 37

N-(4,5,6,7-Tetrahydro-1H-benzimidazol-5-yl)-3-(4-trifluoromethoxyphenyl)acrylamide

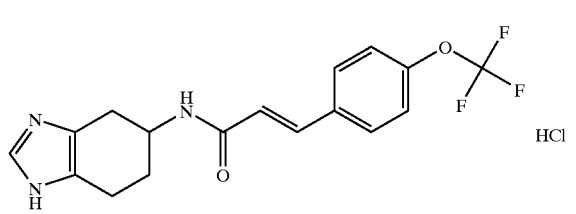

To a solution of 3-(4-trifluoromethyoxyphenyl)acrylic acid (186 mg, 1.0 mmol) in DMA (5 ml), HOAt (136 mg, 1.0 mmol) and DIC (126 mg, 1.0 mmol) were added and the mixture was stirred for 10 min. A mixture prepared from 5-amino-4,5,6,7-tetrahydro-1H-benzimidazole, dihydrochloride (210 mg, 1.0 mmol), DMA (5 ml) and triethylamine (202 mg, 2 mmol) was added to the activated ester and the mixture was stirred for 16 hours at ambient temperature. The volatiles were evaporated and the residue was stirred with a mixture of H$_2$O (40 ml), 1 N hydrochloric acid (20 ml) and diethyl ether (25 ml). The phases were separated and the aqueous phase was washed with diethyl ether (2×25 ml) and then made alkaline to pH 10–11 with 4 N sodium hydroxide. The alkaline mixture was extracted with ethyl acetate (3×50 ml) and the combined organic extracts were dried (magnesium sulphate). The solvent was evaporated in vacuo to give a residue that was dissolved in 1 N hydrochloric acid (50 ml) and the acidic mixture was evaporated to dryness. The residue was re-evaporated with acetone (2×15 ml), stirred with acetone for 1 hour and the solid was isolated by filtration and dried. This afforded 141 mg (36%) of the title compound. HPLC method C: elution at 9.05 min. $^1$H NMR (400 MHz, DMSO-$d_6$) δ 1.80–2.05 (m, 2H), 2.59 (dd, 1H), 2.65–2.80 (m, 2H), 2.98 (dd, 1H), 4.20–4.30 (m, 1H), 6.72 (d, 1H), 7.41 (d, 2H), 7.49 (d, 1H), 7.69 (d, 2H), 8.46 (d, 1H), 8.93 (s, 1H), 14.35 (brs, 2H).

Example 38

2-Naphth-1-yl-N-(4,5,6,7-tetrahydro-1H-benzimidazol-5-yl)acetamide, Hydrochloride

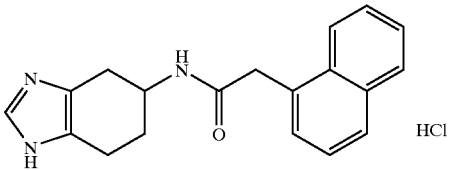

By a similar procedure as described in Example 37 the title compound was prepared. HPLC method C: elution at 7.64 min. $^1$H NMR (400 MHz, DMSO-$d_6$) δ 1.80–1.95 (m, 2H), 2.57 (dd, 1H), 2.60–2.75 (m, 2H), 2.90 (dd, 1H), 3.92 (s, 2H), 4.07–4.17 (m, 1H), 7.40–7.55 (m, 4H), 7.81 (d, 1H), 7.90–7.95 (m, 1H), 8.05–8.10 (m, 1H), 8.53 (d, 1H), 8.93 (s, 1H), 14.35 (brs, 2H).

Example 39

3-(4-Chlorophenyl)-N-(4,5,6,7-tetrahydro-1H-benzimidazol-5-yl)acrylamide, Hydrochloride

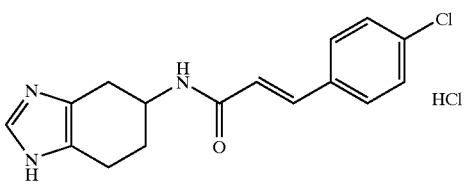

By a similar procedure as described in Example 37 the title compound was prepared. HPLC method C: elution at 8.17 min. $^1$H NMR (400 MHz, DMSO-$d_6$) δ 1.80–2.02 (m, 2H), 2.60 (dd, 1H), 2.68–2.80 (m, 2H), 2.98 (dd, 1H), 4.20–4.30 (m, 1H), 6.72 (d, 1H), 7.44 (d, 1H), 7.48 (d, 2H), 7.59 (d, 2H), 8.47 (d, 1H), 8.93 (s, 1H), 14.35 (brs, 2H).

Example 40

2-Phenoxy-N-(4,5,6,7-tetrahydro-1H-benzimidazol-5-yl)benzamide, Hydrochloride

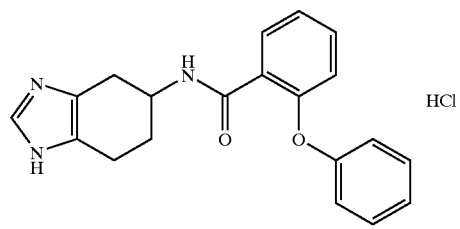

By a similar procedure as described in Example 37 the title compound was prepared. Microanalysis for C$_{20}$H$_{19}$N$_3$O$_2$,HCl: Calc: C: 64.95%; H: 5.45%; N: 11.36%. Found: C: 64.42%; H: 5.56%; N: 11.34%. HPLC method C: elution at 7.96 min. $^1$H NMR (400 MHz, DMSO-$d_6$) δ 1.80–1.90 (m, 2H), 2.50–2.60 (dd, 1H), 2.65 (t, 2H), 2.88 (dd, 1H), 4.20–4.28 (m, 1H), 6.95 (m, 3H), 7.12 (t, 1H), 7.23 (t, 1H), 7.36 (t, 2H), 7.45 (t, 1H), 7.60 (d, 1H), 8.34 (d, 1H), 8.87 (s, 1H), 14.2 (brs, 2H).

Example 41

3-(4-Chlorophenyl)-N-(4,5,6,7-tetrahydro-1H-benzimidazol-5-yl)propionamide

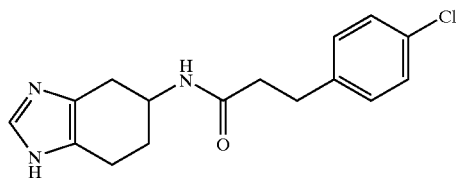

By a similar procedure as described in Example 37 the title compound was prepared. Activation of 3-(4-chlorophenyl)propionic acid was made with CDI (1 eq.) in DCM instead of HOAt/DIC in DMA. HPLC method C: elution at 7.60 min. $^1$H NMR (400 MHz, DMSO-d$_6$) δ 1.70–1.90 (m, 2H), 2.48 (t, 2H), 2.45 (dd, 1H), 2.65 (t, 2H), 2.82 (t, 2H), 2.86 (dd, 1H), 4.02–4.12 (m, 1H), 7.21 (d, 2H), 7.31 (d, 2H), 8.02 (d, 1H), 8.88 (s, 1H), 14.2 (brs, 2H).

Example 42

2-Cyclohexyl-N-(4,5,6,7-tetrahydro-1H-benzimidazol-5-yl)acetamide, Hydrochloride

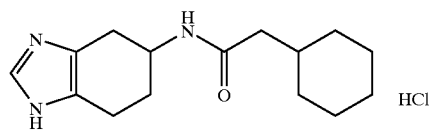

By a similar procedure as described in Example 41 the title compound was prepared. HPLC method C: elution at 7.22 min. $^1$H NMR (400 MHz, DMSO-d$_6$) δ 0.82–0.95 (m, 2H), 1.05–1.25 (m, 3H), 1.55–1.70 (m, 6H), 1.82–1.93 (m, 2H), 1.95 (d, 2H), 2.45–2.50 (m, 1H), 2.60–2.75 (m, 2H), 2.88 (dd, 1H), 4.03–4.12 (m, 1H), 8.00 (d, 1H), 8.90 (s, 1H), 14.5 (brs, 2H).

Example 43

4-(4-Chlorophenyl)-N-(4,5,6,7-tetrahydro-1H-benzimidazol-5-yl)butyramide, Hydrochloride

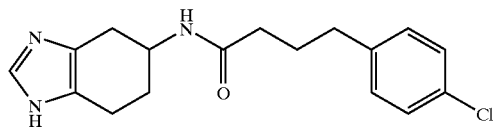

By a similar procedure as described in Example 41 the title compound was prepared. HPLC method C: elution at 8.50 min. $^1$H NMR (400 MHz, DMSO-d$_6$) δ 1.70–1.85 (m, 2H), 1.85–1.95 (m, 1H), 2.09 (t, 2H), 2.45–2.60 (m, 4H), 2.60–2.75 (m, 2H), 2.88 (dd, 1H), 4.05–4.15 (m, 1H), 7.20 (d, 2H), 7.33 (d, 2H), 8.05 (d, 1H), 8.91 (s, 1H), 14.5 (brs, 2H).

Example 44

4-Chloro-N-(4,5,6,7-tetrahydro-1H-benzimidazol-5-yl)benzamide, Hydrochloride

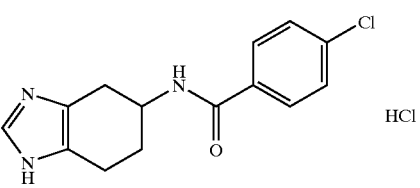

By a similar procedure as described in Example 41 the title compound was prepared. HPLC method C: elution at 7.11 min. $^1$H NMR (400 MHz, DMSO-d$_6$) δ 1.90–2.08 (m, 2H), 2.65–2.80 (m, 3H), 3.00 (dd, 1H), 4.25–4.35 (m, 1H), 7.55 (d, 2H), 7.91 (d, 2H), 8.70 (d, 1H), 8.92 (s, 1H), 14.5 (brs, 2H).

Example 45

5-Phenylpentanoic Acid (4,5,6,7-Tetrahydro-1H-benzimidazol-5-yl)amide, Hydrochloride

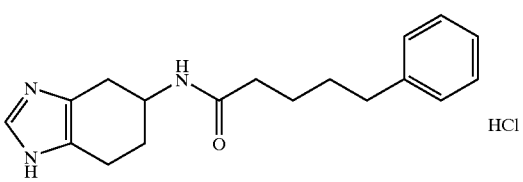

By a similar procedure as described in Example 41 the title compound was prepared. HPLC method C: elution at 8.11 min. $^1$H NMR (400 MHz, DMSO-d$_6$) δ 1.45–1.55 (m, 4H), 1.72–1.95 (m, 2H), 2.12 (t, 2H), 2.45–2.70 (m, 5H), 2.88 (dd, 1H), 4.05–4.15 (m, 1H), 7.15–7.30 (m, 5H), 8.06 (d, 1H), 8.90 (s, 1H), 14.55 (brs, 2H).

Example 46

2-Adamantan-1-yl-N-(4,5,6,7-tetrahydro-1H-benzimidazol-5-yl)acetamide, Hydrochloride

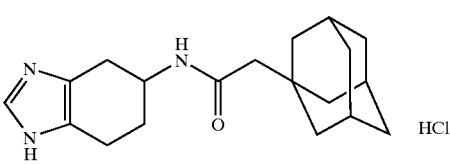

By a similar procedure as described in Example 41 the title compound was prepared. HPLC method C: elution at 8.11 min. $^1$H NMR (400 MHz, DMSO-d$_6$) δ 1.5–1.8 (m, 13H), 1.82–1.93 (m, 7H), 2.60–2.75 (m, 2H), 2.88 (dd, 1H), 4.05–4.15 (m, 1H), 7.92 (d, 1H), 8.91 (s, 1H), 14.5 (brs, 2H).

Example 47

2-Bicyclo[2.2.1]hept-2-yl-N-(4,5,6,7-tetrahydro-1H-benzimidazol-5-yl)acetamide, Hydrochloride

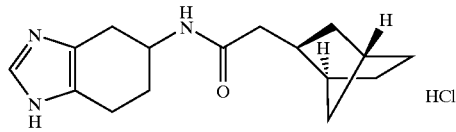

By a similar procedure as described in Example 41 the title compound was prepared. HPLC method C: elution at 7.50 min.

Example 48

2-Chloro-6-phenoxy-N-(4,5,6,7-tetrahydro-1H-benzimidazol-5-yl)benzamide, Hydrochloride

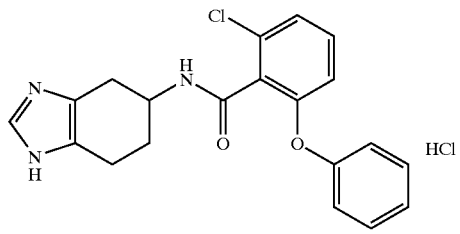

By a similar procedure as described in Example 37 the title compound was prepared. HPLC method D: elution at 11.20 min.

Example 49

1-Phenyl-3-(4,5,6,7-tetrahydro-1H-benzimidazol-5-yl)thiourea

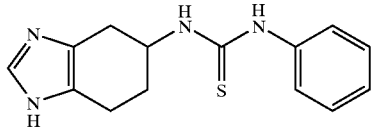

A mixture of 5-amino-4,5,6,7-tetrahydro-1H-benzimidazole, dihydrochloride (210 mg, 1.0 mmol), ethanol (1 ml), triethylamine (0.276 ml, 2.0 mmol) and phenylisothiocyanate (270 mg, 2.0 mmol) was stirred for 3 hours at ambient temperature. 1 N hydrochloric acid (20 ml), DCM (50 ml) and H$_2$O (20 ml) were added. The phases were separated and the aqueous phase was washed with DCM (3×25 ml) and then made alkaline with 4 N sodium hydroxide. The alkaline mixture was extracted with DCM (2×20 ml) and the combined organic extracts were dried (magnesium sulphate). The solvent was evaporated in vacuo to give 140 mg (52%) of the title compound. $^1$H NMR (400 MHz, DMSO-d$_6$) δ 1.80–2.05 (m, 2H), 2.35–2.63 (m, 3H), 2.80–3.00 (m, 1H), 4.55–4.70 (m, 1H), 7.06 (t, 1H), 7.30 (t, 2H), 7.40–7.50 (m, 3H), 7.75–8.85 (m, 1H), 9.45 (s, 1H), 11.65 (d, 1H).

Example 50

1-Cyclohexyl-3-(4,5,6,7-tetrahydro-1H-benzimidazol-5-yl)thiourea

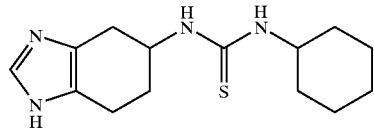

By a similar procedure as described in Example 49 the title compound was prepared. $^1$H NMR (400 MHz, DMSO-d$_6$) δ 1.00–1.34 (m, 5H), 1.45–1.70 (m, 3H), 1.70–1.95 (m, 4H), 2.35–2.65 (m, 3H), 2.85 (d, 1H), 3.90–4.05 (m, 1H), 4.45–4.60 (m, 1H), 7.30 (s, 2H), 7.52 (s, 1H).

Example 51

N-[2-(4-Chlorophenyl)ethyl]-2-(4,5,6,7-tetrahydro-1H-benzimidazol-5-yl)acetamide Hydrochloride

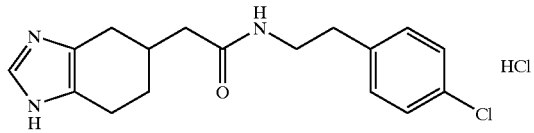

Step 1: 1(3)-Triphenylmethyl-4,5,6,7-tetrahydro-1H-benzimidazole-5-carboxylic Acid Methyl Ester

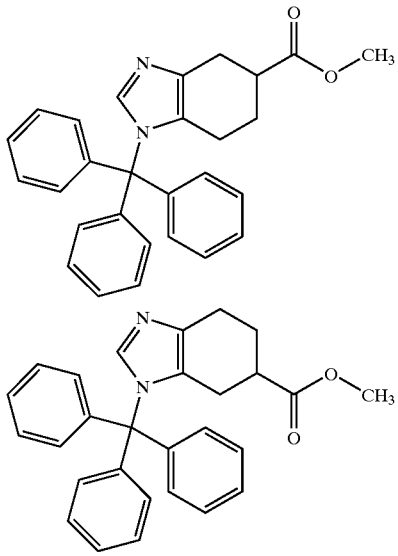

A solution of 4,5,6,7-tetrahydro-1H-benzimidazole-5-carboxylic acid hydrochloride (5.0 g, 23 mmol) in MeOH (100 ml) was stirred under an atmosphere of nitrogen on an ice-bath. Thionyl chloride (2.5 ml, 35 mmol) was added drop wise over 10 min. The mixture was stirred for an additional 30 min and then refluxed for 2 hours. The volatiles were evaporated to give a residue, which was re-evaporated with acetonitrile (2×) and then stirred with acetonitrile (150 ml). Triethylamine (9.5 ml, 69 mmol) was added to the mixture followed by portion wise addition of triphenylmethyl chloride (6.4 g, 23 mmol). The mixture was stirred overnight at room temperature and then filtered. The solvent was evaporated from the filtrate to give a residue, which was stirred with diethyl ether (200 ml). The mixture was filtered and the solvent was evaporated from the filtrate. This afforded a foamy residue which was dissolved in ethyl actetate (10 ml) and heptane (10 ml) and purified by chromatography on silica gel (150 g, heptane/ethyl acetate 1:1) to give 6.4 g (66%) of 1(3)-triphenylmethyl-4,5,6,7-tetrahydro-1H-benzimidazole-5-carboxylic acid methyl ester. Mp. 155–156° C. LC-MS: Calc for MH$^+$: 423.5; Found: 423.4; $^1$H NMR (CDCl$_3$, 400 MHz, two regioisomers, 1:2): δ 1.25–1.40, 1.55–1.70, 1.73–1.85 and 1.97–2.05 (all m, together 4H), 2.45–2.75 and 2.82–2.95 (both m, together 3H), 3.56 and 3.67 (both s, together 3H), 7.10–7.15 (m, 6H), 7.26 and 7.28 (both s, together 1H), 7.30–7.35 (m, 9H).

Step 2: 1(3)-Triphenylmethyl-4,5,6,7-tetrahydro-1H-benzimidazole-5-methanol

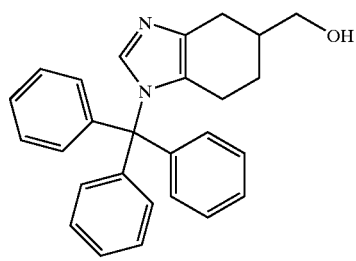

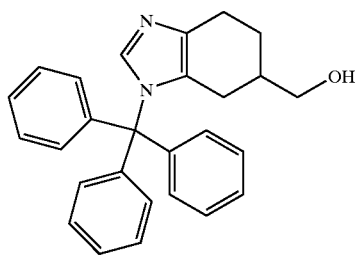

A solution of 1(3)-triphenylmethyl-4,5,6,7-tetrahydro-1H-benzimidazole-5-carboxylic acid methyl ester (5.5 g, 13 mmol) in THF (100 ml) was stirred under an atmosphere of nitrogen. A 1M solution of lithium aluminiumhydride in THF (8 ml, 8.0 mmol) was added drop wise. The reaction mixture was stirred for 1 hour and then heated at reflux for 30 min. To the cooled reaction mixture, H$_2$O (0.5 ml) and 4 N sodium hydroxide (1.0 ml) were added. THF (50 ml) and magnesium sulphate (10 g) were added and the mixture was stirred for 15 min. The mixture was filtered and the solvent was evaporated from the filtrate to give a residue which was dried. This afforded 5.35 g of 1(3)-triphenylmethyl-4,5,6,7-tetrahydro-1H-benzimidazole-5-methanol in a quantitative yield. Mp. 235–238° C. HPLC method A: elution at 7.88 and 8.39 min. LC-MS: Calc for MH$^+$: 395.5; Found: 395.4. $^1$H NMR (CDCl$_3$, 400 MHz, two regioisomers, 1:2): δ 1.15–1.45 (m, 2H), 1.65–1.85 (m, 4H), 2.3–2.4 and 2.6–2.8 (both m, together 2H), 3.2–3.35 and 3.45–3.6 (both m, together 2H), 7.10–7.15 (m, 6H, 7.26 (s, 1H), 7.30–7.35 (m, 9H).

Step 3: (4,5,6,7-Tetrahydro-1H-benzimidazol-5-yl)acetonitrile hydrochloride

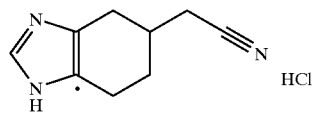

A mixture of 1(3)-triphenylmethyl-4,5,6,7-tetrahydro-1H-benzimidazole-5-methanol (8.0 g, 20 mmol) and dry pyridine (50 ml) was placed under an atmosphere of nitrogen and on an ice-bath. Methanesulfonyl chloride (3.0 ml, 40 mmol) was added dropwise at 0° C. The ice-bath was removed and the mixture was stirred at ambient temperature for 2 hours. The volatiles were evaporated and the residue was stirred with a mixture of toluene (300 ml) and H$_2$O (150 ml). The phases were separated and the organic phase was washed with H$_2$O (50 ml) and brine and dried (Na$_2$SO$_4$). The solvent was evaporated and the residue was dried in vacuo to give 10.2 g of crude methanesulfonic acid (1(3)-triphenylmethyl-4,5,6,7-tetrahydro-1H-benzimidazol-5-yl) methyl ester. This mesylate (10.2 g, 20 mmol) was stirred with a 0.5 M lithium cyanide solution in DMF (60 ml, 30 mmol) under an atmosphere of nitrogen. Potassium iodide (approx. 0.5 g) was added and the mixture was stirred at 80° C. overnight. The volatiles were evaporated and the residue was treated with H$_2$O (150 ml) and ethyl acetate (300 ml). The phases were separated and the organic phase was washed with water and brine and dried (magnesium sulphate). The solvent was evaporated and the residue was re-evaporated with acetonitrile to give 9.6 g of crude (1(3)-triphenylmethyl-4,5,6,7-tetrahydro-1H-benzimidazol-5-yl) acetonitrile. 90% acetic acid (150 ml) was added and the mixture was heated at reflux for 1 hour. The volatiles were evaporated and the residue was stirred with a mixture of 0.5 N hydrochloric acid (100 ml) and diethyl ether (100 ml). The phases were separated and the aqueous phase was washed with diethyl ether (2×100 ml). The aqueous phase was evaporated to dryness and the residue was re-evaporated several times with acetone to give 3.5 g (89%) of (4,5,6,7-tetrahydro-1H-benzimidazol-5-yl)acetonitrile hydrochloride. $^1$H NMR (DMSO-d$_6$, 400 MHz): δ 1.5–1.65 (m, 1H), 1.95–2.05 (m, 1H), 2.15–2.25 (m, 1H), 2.35–2.45 (m, 1H), 2.55–2.75 (m, 4H), 2.83 (dd, 1H), 8.90 (s, 1H), 14.5 (brs, 2H).

Step 4: (4,5,6,7-Tetrahydro-1H-benzimidazol-5yl)acetic acid hydrochloride

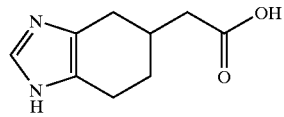

A solution of (4,5,6,7-tetrahydro-1H-benzimidazol-5-yl) acetonitrile hydrochloride (3.0 g, 15 mmol) in 5 N hydrochloric acid (75 ml) was heated at reflux overnight. The volatiles were evaporated and the residue was re-evaporated with acetonitrile (3×). The residue was dissolved in acetone and left for crystallisation. The precipitate was isolated and dried to give 3.25 g (99%) of (4,5,6,7-tetrahydro-1H-benzimidazol-5-yl)acetic acid hydrochloride. $^1$H NMR (DMSO-d$_6$, 400 MHz): δ 1.45–1.60 (m, 1H), 1.90–1.95 (m, 1H), 2.1–2.2 (m, 1H), 2.25–2.40 (m, 3H), 2.55–2.70 (m, 2H), 2.78 (dd, 1H), 12.3 (brs, 1H), 14.55 (brs, 2H).

Step 5:
By a similar procedure as described in Example 1 the title compound was prepared starting from (4,5,6,7-tetrahydro- 1H-benzimidazol-5-yl)acetic acid and 2-(4-chlorophenyl)-ethylamime. HPLC method D: elution at 8.74 min.

Example 52

N-[2-(4,5,6,7-Tetrahydro-1H-benzimidazol-5-yl)ethyl]-2-(4-trifluoromethoxy-henyl)acetamide, hydrochloride

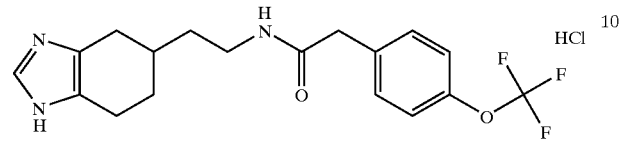

Step 1: 2-(1(3)-Triphenylmethyl-4,5,6,7-tetrahydro-1H-benzimidazol-5-yl)ethylamine oxalate

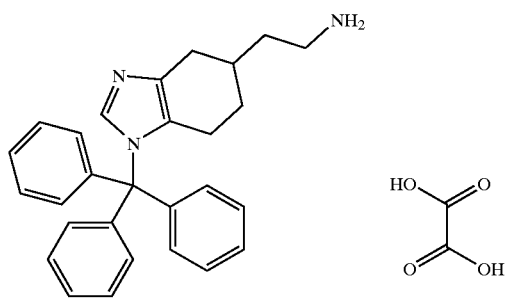

A mixture of (1(3)-triphenylmethyl-4,5,6,7-tetrahydro-1H-benzimidazol-5-yl)acetonitrile (1.5 g, 3.7 mmol, prepared as described in Example 51) and dry THF (10 ml) was placed under an atmosphere of nitrogen. A 1 M lithium aluminiumhydride solution in THF (3.0 ml, 3.0 mmol) was added dropwise with stirring. The reaction mixture was stirred for 1 hour and then quenched with a small amount of water and 4 N sodium hydroxide solution. The mixture was diluted with ethyl acetate (30 ml) and then stirred with magnesium sulphate to remove water. The mixture was filtered and the solvent was evaporated. The residue was dissolved in ethyl acetate (75 ml) and oxalic acid (0.3 g) dissolved in ethyl acetate was added. The solid formed was isolated by filtration and dried. This afforded 1.4 g (77%) of 2-(1(3)-triphenylmethyl-4,5,6,7-tetrahydro-1H-benzimidazol-5-yl)ethylamine oxalate.

Step 2:

A mixture of 2-(1(3)-triphenylmethyl-4,5,6,7-tetrahydro-1H-benzimidazol-5-yl)ethylamine oxalate (400 mg, 0.80 mmol), DCM (10 ml), triethylamine (0.138 ml, 1.0 mmol), 4-(trifluoromethoxy)phenylacetic acid (220 mg, 1.0 mmol), HOAt (136 mg, 1.0 mmol) and EDAC (195 mg, 1.0 mmol) was stirred overnight at ambient temperature. DCM (15 ml) was added and the mixture was washed with H$_2$O (2×15 ml). The organic phase was evaporated and the residue was dissolved in 90% acetic acid (15 ml). The acidic mixture was heated at reflux for 2 hour and the evaporated to dryness. The residue was stirred with 0.5 N hydrochloric acid (30 ml) and diethyl ether (15 ml). The phases were separated and the aqueous phase was washed with diethyl ether (15 ml) and then made alkaline with 1 N sodium hydroxide. The alkaline mixture was extracted with ethyl acetate (30 ml) and the organic extract was washed with water and brine. The solvent was evaporated in vacuo to give a residue that was dissolved in 0.5 N hydrochloric acid and re-evaporated. The residue was stirred with acetone (15 ml) to give a solid. This afforded after filtration and drying 150 mg (46%) of the title compound. HPLC method E: elution at 5.35 min.

Example 53

Naphthalene-1-carboxylic acid [2-(4,5,6,7-tetrahydro-1H-benzimidazol-5-yl)ethyl]amide, hydrochloride

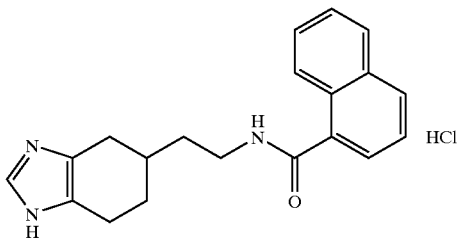

By a similar procedure as described in Example 52 the title compound was prepared starting from 2-(1(3)-triphenylmethyl-4,5,6,7-tetrahydro-1H-benzimidazol-5-yl)ethylamine oxalate and 1-naphthoic acid. $^1$H NMR (400 MHz, DMSO-d$_6$) δ1.45–1.60 (m, 1H), 1.6–1.8 (m, 2H), 1.90–2.05 (m, 2H), 2.25–2.35 (m, 1H), 2.55–2.80 (m, 2H), 2.80–2.95 (m, 1H), 3.45 (q, 2H), 7.45–7.65 (m, 4H), 7.95–8.05 (m, 2H), 8.15–8.20 (m, 1H), 8.64 (t, 1H), 8.91 (s, 1H), 14.45 (brs, 2H).

Example 54

4,5,6,7-Tetrahydro-1H-benzimidazole-5-carboxylic acid N-[4-(4-chlorophenyl)butyl]-N-methylamide

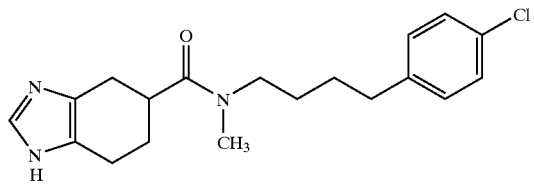

Step 1: 4-(4-Chlorophenyl)-N-methylbutyramide

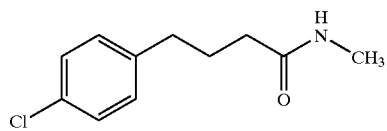

At 0° C., 1-(3-dimethylaminopropyl)-3-ethylcarbodiimide (7.70 g, 40.3 mmol) was added to a solution of 4-chloropehnylbutyric acid (8.00 g, 40.3 mmol) and 1-hydroxybenzotriazole (5.40 g, 40.3 mmol) in DCM (60 ml) and N,N-dimethylformamide (60 ml). The reaction mixture was stirred for 20 min at 0° C. An 8.0 M solution of methylamine in ethanol (100 ml, 805 mmol) was added. The reaction mixture was stirred for 16 hours at room temperature. It was diluted with ethyl acetate (150 ml) and washed with a 10% aqueous solution of sodium hydrogen sulphate (150 ml). The aqueous phase was extracted with ethyl acetate (3×100 ml). The combined organic layers were washed with a saturated aqueous solution of sodium hydro gen carbonate (150 ml) and dried over magnesium sulphate. The solvent was removed in vacuo. The crude product was purified by flash chromatography on silica (200 g), using ethyl acetate/heptane (2:1) as eluent, to give 3.81 g of 4-(4-chlorophenyl)-N-methylbutyramide. $^1$H NMR (CDCl$_3$): δ1.95 (tt, 2H); 2.15 (t, 2H); 2.60 (t, 2H); 2.80 (d, 3H); 5.80 (br, 1H); 7.07 (d, 2H); 7.25 (d, 2H).

Step 2: N-[4-(4-Chlorophenyl)butyl]-N-methylamine

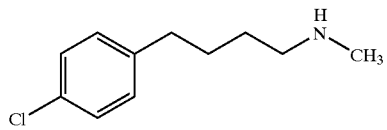

At 0° C., a solution of of 4-(4-chlorophenyl)-N-methylbutyramide (3.80 g, 18.0 mmol) in tetrahydrofuran (60 ml) was added to a suspension of sodium borohydride (1.60 g, 43.1 mmol) in THF (60 ml). The mixture was stirred for 20 min at 0° C. A solution of iodine (4.6 g, 18.0 mmol) in THF (100 ml) was added dropwise. After the addition was finished, the reaction mixture was warmed to 70° C. It was stirred for 16 hours at this temperature. It was cooled to 0° C. Methanol (100 ml) was added dropwise. The solvents were removed in vacuo. The residue was dissolved in a 20% aqueous solution of sodium hydroxide (160 ml) and tert-butyl methyl ether (200 ml). The phases were separated. The aqueous phase was extracted with tert-butyl methyl ether (3×70 ml). The combined organic layers were dried over magnesium sulphate. The solvent was removed in vacuo. The crude product was purified by flash chromatography on silica (90 g), using DCM/methanol/25% aqueous ammonia as eluent, to give 820 mg of N-[4-(4-chlorophenyl)butyl]-N-methylamine. MS: calc for [M+H]$^+$: 198; Found: 198. $^1$H NMR (DMSO-d$_6$) δ1.50 (tt, 2H); 1.65 (tt, 2H); 1.75 (br, 1H); 2.40 (s, 3H); 2.55 (m, 4H); 7.10 (d, 2H); 7.25 (d, 2H).

Step 3:

Analogously to example 2, 1.00 g of the title compound was synthesized, starting with 0.60 g of N-[4-(4-chlorophenyl)butyl]-N-methylamine. HPLC method C: elution at 9.48 min. MS: calc for [M+H]$^+$: 346; Found: 346. $^1$H NMR (CDCl$_3$, 2 sets of signals) δ1.55 (m, 4H); 2.00 (m, 2H); 2.65 (m, 6H); 2.92 and 3.05 (both s, together 3H); 3.40 (m, 3H); 7.05 and 7.10 (both d, together 2H); 7.20 and 7.25 (both d, together 2H); 7.45 and 7.46 (both s, together 1H).

For biological testing, the title compound was transferred into its hydrochloride salt by addition of a 3.5 M solution of hydrogen chloride in ethyl acetate (0.85 ml). The solvent was removed in vacuo. The residue was dissolved in acetone. The solvent was removed in vacuo. Finally the residue was dissolved in water (40 ml) and lyophilized. Microanalysis for C$_{19}$H$_{24}$ClN$_3$O, 3HCl: Calc: C: 50.13%; H: 5.98%; N: 9.23%; Found: C: 50.44%; H: 6.24%; N: 9.50%.

Example 55

4,5,6,7-Tetrahydro-1H-benzimidazole-5-carboxylic acid N-methyl-N-(2-phenoxybenzyl)amide

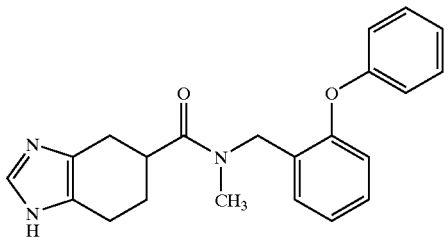

Step 1: N-Methyl-2-phenoxybenzamide

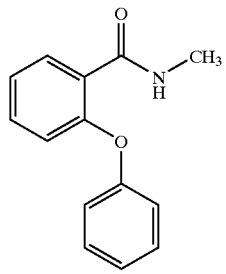

At 0° C., 1-(3-dimethylaminopropyl)-3-ethylcarbodiimide (22.4 g, 0.117 mol) was added to a solution of 2-phenoxybenzoic acid (25.0 g, 0.117 mol) and 1-hydroxybenzotrizole (15.8 g, 0.117 mmol) in DCM (80 ml) and N,N-dimethylformamide (160 ml). The reaction mixture was stirred for 20 min at 0° C. A 8.0 M solution of methylamine in ethanol (290 ml, 2.33 mol) was added. The reaction mixture was stirred for 16 hours at room temperature. It was diluted with ethyl acetate (200 ml) and washed with a 10% aqueous solution of sodium hydrogen sulphate (300 ml). The aqueous phase was extracted with ethyl acetate (3×100 ml). The combined organic layers were washed with a saturated aqueous solution of sodium hydrogen carbonate and dried over magnesium sulphate. The solvent was removed in vacuo. The crude product was purified by flash chromatography on silica (300 g), using ethyl acetate/heptane 1:1 as eluent, to give 22.2 g of N-methyl-2-phenoxybenzamide. $^1$H NMR (CDCl$_3$); δ3.00 (d, 3H); 6.80 (d, 1H); 7.08 (d, 2H); 7.15–7.45 (m, 6H); 7.65 (br, 1H); 8.25 (d, 1H).

Step 2: N-Methyl-N-(2-phenoxybenzyl)amine

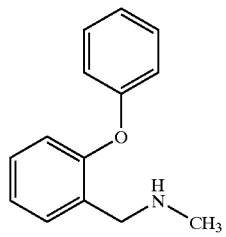

At 0° C., a solution of N-methyl-2-phenoxybenzamide (22.2 g, 97.7 mmol) in THF (175 ml) was added dropwise to a suspension of sodium borohydride (9.20 g, 2.44 mmol)

in THF (100 ml). The reaction mixture was stirred at 0° C. for 20 min. A solution of iodine (24.8 g 97 mmol) in THF (1.25 ml) was added dropwise. The reaction mixture was heated to 70° C. for 16 hours. It was cooled to 0° C. Methanol 500 ml was added dropwise. The solvents were removed in vacuo. The residue was dissolved in a mixture of tert-butyl methyl ether (200 ml) and a 20% aqueous solution of sodium hydroxide (200 ml). The phases were separated. The aqueous phase was extracted with tert-butyl methyl ether (3×100 ml). The combined organic layers were dried over magnesium sulphate. The solvent was removed in vacuo. The crude product was purified by flash chromatography on silica (300 g), using a mixture of DCM/methanol/25% aqueous ammonia as eluent, to give 3.04 g of N-methyl-N-(2-phenoxybenzyl)amine. $^1$H NMR (CDCl$_3$); δ2.25 (br, 1H); 2.43 (s, 3H); 3.80 (s, 2H); 6.80–7.50 (m, 9H).

Step 3:

480 mg of the title compound was prepared analogously to Example 2, starting with 300 mg of N-methyl-N-(2-phenoxybenzyl)amine. HPLC method C: elution at 9.31 min. MS: calc for [M+H]$^+$: 362; found 362. $^1$H NMR (CDCl$_3$, 2 sets of signals): δ2.00 (m, 2H); 2.50 (m, 1H); 2.70 (m, 3H); 2–95 (m, 1H); 3.05 and 3.07 (both s, together 3H); 4.65 and 4.70 (s and AB, together 2H); 6.90 (m, 4H); 7.00–7.40 (m, 6H); 7.45 and 7.48 (both s, together 1H).

For biological testing, the title compound was transferred into its hydrochloride salt by lyophilization with 0.1 N hydrochloric acid (40 ml). Microanalysis for $C_{22}H_{23}N_3O_2$, HCl, $H_2O$; Calc: C: 63.53%; H: 6.30%; N: 10.10%; Found: C: 62.78%; H: 6.64%; N: 9.24%.

Example 56

4,5,6,7-Tetrahydro-1H-benzimidazole-5-carboxylic acid N-[4-(4-fluorophenyl)-butyl]-N-methylamide

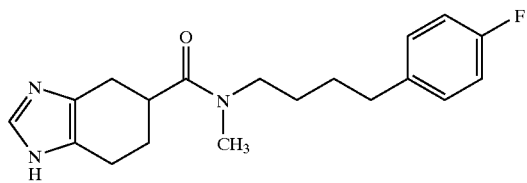

Step 1: 4-(4-Fluorophenyl)butyric acid

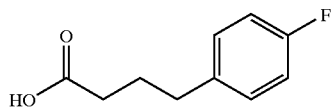

At 0° C., chlorotrimethylsilane (10.6 ml, 84.1 mmol) was added dropwise to a solution of 4-(4-fluorophenyl)-4-oxobutanoic acid (15.0 g, 76.5 mmol) and triethylamine (11.7 ml, 84.1 mmol) in THF (200 ml). The reaction mixture was stirred for 20 min at 0° C. The solid was filtered off. The solvent was removed from the solution. The residue was dissolved in DCM (200 ml). Triethylsilane (40 ml, 252 mmol) was added. An 1 N solution of titan(IV) chloride in DCM (229 ml, 229 mmol) was added dropwise while cooling with a water bath. The reaction mixture was stirred for 16 hours at room temperature. It was given onto ice water (300 ml). The phases were separated. The aqueous phase was extracted with DCM (100 ml). The combined organic phases were extracted with a saturated aqueous solution of sodium hydrogen carbonate (3×150 ml). The sodium hydrogen carbonate phases were combined and acidified with 1 N hydrochloric acid to pH 2. They were extracted with ethyl acetate (5×150 ml). The combined ethyl acetate layers were dried. The solvent was removed in vacuo to give 7.4 g of crude 4-(4-fluorophenyl)butyric acid, which was used in the next step without further purification. $^1$H NMR (DMSO-d$_6$) δ1.80 (m, 2H); 2.20 (t, 2H); 2.60 (t, 2H); 7.10 (m, 2H); 7.20 (m, 2H); 12.05 (s, 1H).

Step 2: 4-(4-Fluorophenyl)-N-methylbutyramide

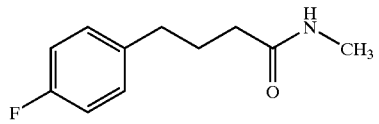

At 0° C., 1-(3-dimethylaminopropyl)-3-ethylcarbodiimide (6.99 g, 36.5 mmol) was added to a solution of crude 4-(4-fluorophenyl)butyric acid (6.64 g, 36.5 mmol) and 1-hydroxybenzotriazole (4.92 g, 36.5 mmol) in N,N-dimethylformamide (50 ml) and DCM (50 ml). The reaction mixture was stirred for 20 min at 0° C. An 8.0 M solution of methylamine in methanol (91 ml, 729 mmol) was added. The reaction mixture was stirred for 16 hours, while it was warming up to room temperature. It was diluted with ethyl acetate (200 ml) and washed with a 10% aqueous solution of sodium hydrogen sulphate (100 ml). The aqueous phase was extracted with ethyl acetate (100 ml). The combined organic layers were washed with a saturated solution of sodium hydrogen carbonate (200 ml) and dried over magnesium sulphate. The solvent was removed in vacuo. The crude product was purified by flash chromatography on silica (100 g), using ethyl acetate/heptane 3:1 as eluent. The product was dissolved in ethyl acetate (200 ml) and washed with water (200 ml). The organic layer was dried over magnesium sulphate. The solvent was removed in vacuo to give 1.31 g of 4-(4-fluorophenyl)-N-methylbutyramide. $^1$H NMR (CDCl$_3$): δ1.95 (m, 2H); 2.15 (m, 2H); 2.65 (t, 2H); 2.81 (d, 3H); 5.40 (br, 1H); 6.95 (m, 2H); 7.10 (m, 2H).

Step 3: N-[4-(4-Fluorophenyl)butyl]-N-methylamine

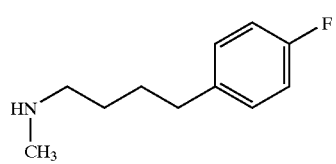

At 0° C., a solution of 4-(4-fluorophenyl)-N-methylbutyramide (1.30 g, 6.70 mmol) in THF (15 ml) was added dropwise to a suspension of sodium borohydride (604 mg, 16.0 mmol) in THF (15 ml). Successively, a solution of iodine (1.70 g, 6.70 mmol) in THF (20 ml) was added dropwise. The reaction mixture was heated to 70° C. for 16 hours. It was cooled to 0° C. Methanol (50 ml) was added carefully. The solvents were removed in vacuo. The residue was dissolved in a mixture of a 32% aqueous solution of sodium hydroxide (100 ml), water (50 ml), and tert-butyl methyl ether (200 ml). The phases were separated. The aqueous phase was extracted with tert-butyl methyl ether (2×100 ml). The combined organic layers were dried over magnesium sulphate. The solvent was removed in vacuo. The crude product was purified by flash chromatography on silica (80 g), using a mixture of DCM/methanol/25% aqueous ammonia (first 100:10:1, then 100:20:2) as eluent, to give 180 mg of N-[4-(4-fluorophenyl)butyl]-N-methylamine. $^1$H NMR (CDCl$_3$): δ1.55 (m, 4H); 2.43 (s, 3H); 2.60 (m, 4H); 3.55 (br, 1H); 6.95 (m, 2H); 7.10 (m, 1H).

Step 4:

200 mg of the title compound were prepared analogously to Example 2, starting with 180 mg of N-[4-(4-fluorophenyl)butyl]-N-methylamine. HPLC method C: elution at 8.86 min. MS: calc for [M+H]$^+$: 330; Found 330. $^1$H NMR CDCl$_3$, 2 sets of signals) δ1.55 (m, 4H); 2.00 (m, 2H); 2.75 (m, 5H); 2.90 (m, 3H); 2.93 and 3.03 (both s, together 3H); 3.35 (m, 1H); 6.90 (m, 2H); 7.10 (m, 2H); 7.44 and 7.45 (both s, together 1H); 8.05 (br, 1H).

For biological testing, the title compound was transferred into its hydrochloride salt by lyophilization with 0.1 N hydrochloride acid (40 ml).

Example 57

4,5,6,7-Tetrahydro-1H-benzimidazole-5-carboxylic acid N-methyl-N-[2-(1-naphthyloxy)ethyl]amide

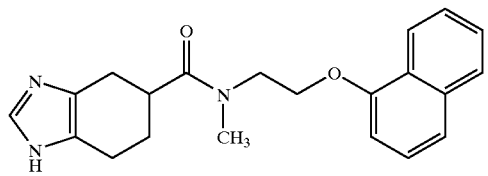

Step 1: N-Methyl-2-(1-naphthyloxy)acetamide

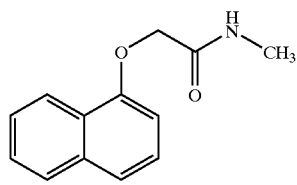

At 0° C., 1-(3-dimethylaminopropyl)-3-ethylcarbodiimide (14.2 g, 74.2 mmol) was added to a solution of (1-naphthyloxy)acetic acid (15.0 g, 74.2 mmol) and 1-hydroxybenzotriazole (10.0 g, 74.2 mmol) in DCM (100 ml) and N,N-dimethylformamide (100 ml). The reaction mixture was stirred for 30 min at this temperature. A 8.0 M solution of methylamine (185 ml, 1.4 mol) was added. The reaction mixture was stirred for 16 hours, while it was warming up to room temperature. It was diluted with ethyl acetate (300 ml) and washed with a 10% aqueous solution of sodium hydrogen sulphate (2×300 ml). The organic layer was washed with a saturated aqueous solution of sodium hydrogen carbonate (400 ml) and dried over magnesium sulphate. The solvent was removed in vacuo. The crude product was purified by flash chromatography on silica (300 g), using ethyl acetate/heptane as eluent, to give 17.44 g of N-methyl-2-(1-naphthyloxy)acetamide. $^1$H NMR (CDCl$_3$): δ2.95 (d, 3H); 4.70 (s, 2H); 6.62 (br, 1H); 6.82 (d, 1H); 7.40 (t, 1H); 7.55 (m, 3H); 7.85 (m, 1H); 8.25 (m, 1H).

Step 2: N-Methyl-N-[2-(1-naphthyloxy)ethyl]amine

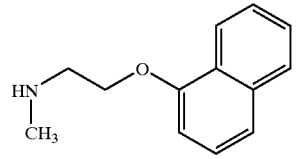

At 0° C., a solution of N-methyl-2-(1-naphthyloxy) acetamide (17.4 g, 81.1 mmol) in THF (100 ml) was added dropwise to a suspension of sodium borohydride (7.35 g, 195 mmol) in THF (100 ml). The reaction mixture was stirred for 15 min at this temperature. A solution of iodine (20.6 g, 81 mmol) in THF (200 ml) was added dropwise. The reaction mixture was heated to 70° C. for 16 hours. It was cooled to 0° C. Methanol (250 ml) was added dropwise. The solvents were removed in vacuo. The residue was dissolved in a mixture of tert-butyl methyl ether (200 ml) and a 20% aqueous solution of sodium hydroxide (200 ml). The phases were separated. The aqueous phase was extracted with tert-butyl methyl ether (2×100 ml). The combined organic layers were dried over magnesium sulphate. The crude product was purified by flash chromatography on silica (200 g), using DCM/methanol/25% aqueous ammonia (100:10:1) as eluent, to give 1.94 g of N-methyl-N-[2-(1-naphthyloxy)ethyl]amine. $^1$H NMR (CDCl$_3$): δ1.85 (br, 1H); 2.58 8s, 3H); 3.15 (t, 2H); 4.25 (t, 2H); 6.85 (d, 1H); 7.38 (m, 1H); 7.45 (m, 1H); 7.50 (m, 2H); 7.80 (m, 1H); 8.25 (m, 1H).

Step 3:

Starting with 397 mg (1.97 mmol) of N-methyl-N-[2-(1-naphthyloxy)ethyl]amine, 110 mg of the title compound was prepared analogously to Example 2. HPLC method C: elution at 8.77 min. MS: calc for [M+H]$^+$: 350; Found: 350. $^1$H NMR (CDCl$_3$, 2 sets of signals) δ1.95 and 2.00 (both d, together 2H); 2.65 (m, 3H); 2.90 and 3.20 (both m, together 2H); 3.05 and 3.25 (both s, together 3H); 3.85 and 3.95 (both m, together 2H); 4.20 and 4.30 (m and t, together 2H); 6.75 and 6.78 (both d, together 1H); 7.30–7.50 (m, 5 H); 7.75 and 7.77 (both d, together 1H); 8.05 and 8.20 (both d, together 1H).

For biological testing, the title compound was transferred into its hydrochloride salt. For this it was dissolved in ethyl acetate (5 ml) and DCM (5 ml). A 3.5 M solution of hydrogen chloride in ethyl acetate (0.48 ml) was added. The crystals were collected.

Example 58

4,5,6,7-Tetrahydro-1H-benzimidazole-5-carboxylic acid N-methyl-N-[2-(3-trifluoromethylphenyl)ethyl] amide

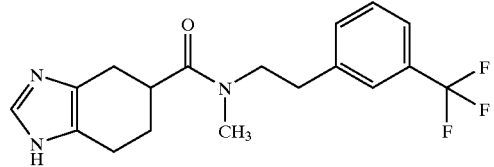

Step 1: N-Methyl-2-(3-trifluoromethylphenyl) acetamide

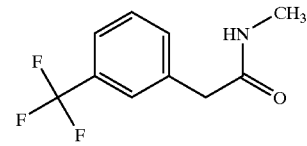

At 0° C., 1-(3-dimethylaminopropryl)-3-ethylcarbodiimide (21.6 g (0.11 mol) was added to a solution of 3-(trifluoromethyl)phenylacetic acid (Aldrich 19,335-6, 23.0 g, 0.11 mol) and 1-hydroxybenzothiazole (21.6 g, 0.11 mol) in DCM (50 ml) and N,N-dimethylformamide (50 ml). The reaction mixture was stirred for 20 min at 0° C. A 33% solution of methylamine in ethanol (280 ml, 2.25 mol) was added. The reaction mixture was stirred for 56 hours and successively diluted with ethyl acetate (200 ml). It was washed with a 10% aqueous solution of sodium hydrogensulphate (300 ml). The aqueous phase was extracted with ethyl acetate (2×150 ml). The combined organic layers were washed with a saturated aqueous solution of sodium hydrogencarbonate (300 ml) and dried over magnesium sulphate. The solvent was removed in vacuo. The crude product was purified by flash chromatography on silica (300 g), using ethyl acetate/heptane 2:1 as eluent, to give 19.8 g of N-methyl-2-(3-trifluoromethylphenyl)acetamide. $^1$H NMR (CDCl$_3$): δ2.76 (d, 3H); 3.60 (s, 2H); 6.05 (br, 1H); 7.40–7.60) (m, 4H).

Step 2: N-Methyl-N-[2-(3-trifluoromethyl)phenyl)ethylamine

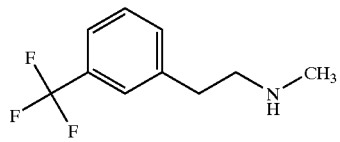

At 0°C., a solution of iodine (23.1 g, 91 mmol) in tetraydrofuran (100 ml) was added dropwise to a suspension of sodium borohydride (8.6 g, 227 mmol) and of N-methyl-2-(3-trifluoromethylphenyl)acetamide (19.8 g, 91 mmol) in THF (150 ml). The reaction mixture was heated to reflux for 16 hours. It was cooled to 0° C. Methanol (200 ml) was added dropwise. The solvent was removed in vacuo. The residue was dissolved in a mixture of tert-butyl methyl ether (200 ml) and a 20% aqueous solution of sodium hydroxide (200 ml). The phases were separated. The aqueous phase was extracted with tert-butyl methyl ether (2×100 ml). The combined organic layers were dried over magnesium sulphate. The solvent was removed in vacuo. The crude product was purified by flash chromatography on silica (300 g), using a mixture of DCM/methanol/25% aqueous ammonia (first: 100:10:1, then 100:20:2, then 100:30:3) as eluent, to give 3.77 g of N-methyl-N-[2-(3-trifluoromethyl)phenyl)ethyl]-amine. $^1$H NMR (CDCl$_3$); δ2.30 (s, 3H); 2.50 (br, 1H); 2.75 (m, 2H); 2.80 (m, 2H); 7.55 (m, 4H).

Step 3:

Starting with 3.77 g of N-methyl-N-[2-(3-trifluoromethyl)phenyl)ethyl]amine 2.49 g of the title compound were prepared analogously to the procedure described in Example 2. HPLC method C: elution at 8.66 min. MS: calc for [M+H]$^+$: 352: Found: 352. $^1$NMR (DMSO-d$_6$) δ: 1.65 and 1.95 (both m, together 2H); 2.30–3.10 (m, 10H); 3.65 (m, 2H); 7.40 (m, 5H).

For biological testing, the title compound was transferred into its hydrochloride salt by lypholization of its solution in 0.1 N hydrochloride acid (40 ml).

Example 59

4,5,6,7-Tetrahydro-1H-benzimidazole-5-carboxylic acid N-[2-(2-chlorophenyl)-ethyl]-N-methylamide.

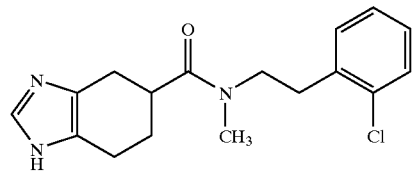

Step 1: 2-(Chlorophenyl)-N-methylacetamide

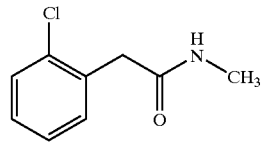

At 0° C., 1-(3-dimethylaminopropyl)-3-ethylcarbodiimide (28.1 g, 0.15 mol) was added to a solution of 1-hydroxybenzotriazole (19.8 g, 0.15 mol) and 2-chlorophenylacetic acid (Aldrich 19,063-2, 25.0 g, 0.15 mol) in N,N-dimethylformamide (150 ml) and DCM (50 ml). The reaction mixture was stirred for 20 min at 0° C. A 33% solution of methylamine in ethanol (365 ml, 2.9 mol) was added. The reaction mixture was stirred for 56 hours at room temperature. It was diluted with ethyl acetate (300 ml) and washed with a 10% aqueous solution of sodium hydrogensulphate (400 ml). The aqueous phase was extracted with ethyl acetate (2×150 ml). The combined organic layers were washed with a saturated solution of sodium hydrogencarbonate (40 ml) and dried over magnesium sulphate. The solvent was removed in vacuo. The crude product was purified by flash chromatography on silica (300 g), using ethyl acetate/heptane 2:1 as eluent, to give 21.6 g of 2-(2-chlorophenyl)-N-methyl-acetamide. $^1$H NMR (CDCl$_3$): δ: 2.75 (d, 3H); 3.70 (s, 2H); 5.45 (br, 1H); 7.20–7.50 (m, 4H).

Step 2: N-[2-(2-Chlorophenyl)ethyl]-N-methylamine

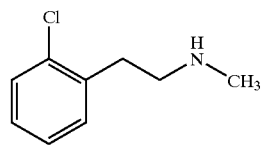

At 0° C., a solution of iodine (29.9 g, 0.12 mol) in THF (100 ml) was added dropwise to a suspension of sodium borohydride (11.1 g, 0.29 mol) and 2-(2-chlorophenyl)-N-methyl-acetamide (21.6 g, 0.12 mol) in THF (150 ml). After the addition was completed, the reaction mixture was heated to reflux for 16 hours. It was cooled to 0° C. Methanol (150 ml) was added dropwise. The solvent was removed in vacuo. The residue was dissolved in a mixture of tert-butyl methyl ether (200 ml) and a 20% aqueous solution of sodium hydroxide (200 ml). The phases were separated. The aqueous phase was extracted with tert-butyl methyl ether (2×100 ml). The combined organic layers were dried over magnesium sulphate. The solvent was removed in vacuo. The crude product was purified by flash chromatography on silica (300 g), using a mixture of DCM/methanol/25% aqueous ammonia (first: 100:10:1, then: 100:20:2, then 100:30:3) as eluent, to give 3.82 g of N-[2-(2-chlorophenyl)ethyl]-N-methylamine. $^1$H NMR (CDCl$_3$): δ2.05 (s, 1H); 2.50 (s, 3H); 2.87 (m, 2H); 2.95 (m, 2H); 7.10–7.40 (m,4H).

Step 3:

Starting with 3.8 g of N-[2-(2-chlorophenyl)ethyl]-N-methylamine 2.92 g of the title compound were prepared analogously to the procedure described in Example 2. HPLC method C: elution at 7.94 min. MS: calc for [M+H]$^+$: 318; Found: 318. $^1$H NMR (DMSO-d$_6$) δ1.75 and 1.90 (both m, together 2H); 2.40–3.10 (m, 10H); 3.65 (m, 2H); 7.10–7.50 (m, 4H).

For biological testing, the title compound was transferred into its hydrochloride salt by lyophilization of its solution in 0.1 N hydrochloric acid (40 ml).

Example 60

4,5,6,7-Tetrahydro-1H-benzimidazole-5-carboxylic acid propylamide

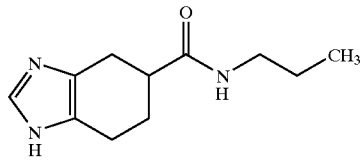

Starting with 0.14 g of the hydrochloride salt of propylamine, 30 mg of the title compound were prepared analogously to the procedure described in Example 2. HPLC method C: elution at 3.07 min MS: calc for [M+H]$^+$: 208; Found: 208. $^1$H NMR (CD$_3$OD) δ: 0.95 (t, 3H); 1.55 (m, 2H); 1.90 (m, 1H); 2.05 (m, 1H); 2.50–2.80 (m, 5H); 3.15 (t, 1H); 7.45 (s, 1H).

For biological testing, the title compound was transferred into its hydrochloride salt by lyophilization in its solution in 0.1 N hydrochloric acid (40 ml).

Example 61

1-Cyclohexyl-3-((4,5,6,7-tetrahydro-1H-benzimidazol-5-yl)methyl)thiourea

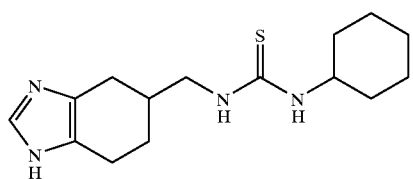

Step 1: 2-((1-Triphenylmethyl-4,5,6,7-tetrahydro-1H-benzimidazol-5-yl)methyl)isoindole-1,3-dione and 2-((3-triphenylmethyl-4,5,6,7-tetrahydro-3H-benzimidazol-5-yl)methyl)isoindole-1,3-dione

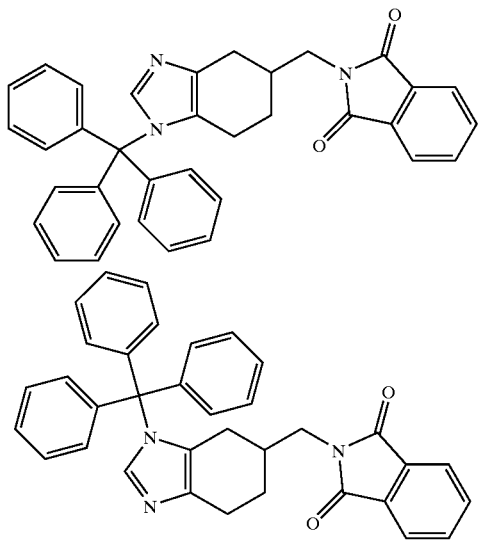

Diethyl azodicarboxylate (0.9 ml, 5.70 mmol) was added dropwise to a suspension of a mixture of 1-triphenylmethyl-4,5,6,7-tetrahydro-1H-benzimidazole-5-methanol and 3-triphenylmethyl-4,5,6,7-tetrahydro-3H-benzimidazole-5-methanol (1.50 g, 3.80 mmol, prepared as described in Example 51), phthalimide (0.56 g, 3.80 mmol), and triphenylphosphine (1.50 g, 5.70 mmol) in THF (50 ml). The reaction mixture was stirred for 3 hours at room temperature. It was diluted with ethyl acetate (100 ml) and washed with a saturated aqueous solution of sodium hydrogencarbonate (100 ml). The aqueous phase was extracted with ethyl acetate (2×60 ml). The combined organic layers were washed with water (100 ml) and dried over magnesium sulphate. The solvent was removed in vacuo. The crude product was purified by flash chromatography on silica (90 g), using a mixture of DCM/methanol/25% aqueous ammonia (100:10:1 as eluent, to give 3.92 g of a mixture of 2-((1-triphenylmethyl-4,5,6,7-tetrahydro-1H-benzimidazol-5yl)methyl)isoindole-1,3-dione and 2-((3-triphenylmethyl-4,5,6,7-tetrahydro-3H-benzimidazol-5-yl)methyl)) isoindole-1,3-dione which contained triphenylphosphine as impurity. $^1$H NMR (CDCl$_3$, 2 sets of signals): δ1.30 (m, 2H); 1.60, 1.80, 2.05, and 2.15 (all m, together 3H); 2.40, 2.65, and 2.70 (all m, together 2H); 3.30, 3.45, and 3.65 (dd, dd, and m, together 2H); 7.00–7.90 (m, 20H).

Step 2: ((1-Triphenylmethyl-4,5,6,7-tetrahydro-1H-benzimidazol-5-yl)methyl)amine and ((3-triphenylmethyl-4,5,6,7-tetrahydro-3H-benzimidazol-5-yl)methyl)amine.

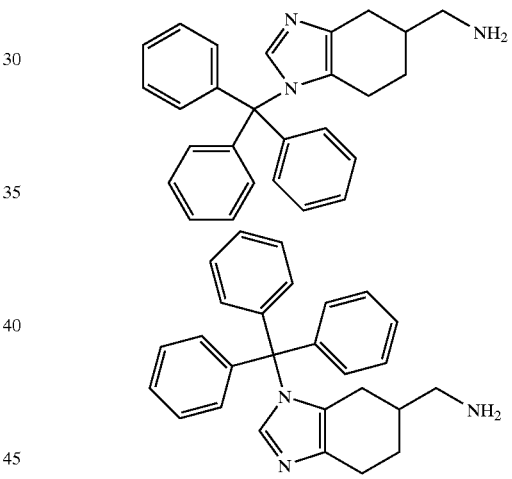

A solution of a mixture of 2-((1-triphenylmethyl-4,5,6,7-tetrahydro-1H-benzimidazol-5-yl)methyl)isoindole-1,3-dione and 2-((3-triphenylmethyl-4,5,6,7-tetrahydro-3H-benzimidazol-5-yl)methyl)isoindole-1,3-dione, which contained triphenylphosphine as impurity, (3.92 g) in ethanol was heated to 80° C. Hydrazine hydrate (5.1 ml, 105 mmol) was added. The reaction mixture was heated to 80° C. for 3 hours. It was cooled to room temperature and stirred 16 hours at room temperature. The solid was filtered off, the filtrate was taken, and the solvent was removed in vacuo. The crude product was purified by flash chromatography on silica (90 g), using a mixture of DCM/methanol/25% aqueous ammonia (100:10:1) as eluent, to give 1.47 g of a mixture of ((1-triphenylmethyl-4,5,6,7-tetrahydro-1H-benzimidazol-5-yl)methyl)amine and ((3-triphenylmethyl-4,5,6,7-tetrahydro-3H-benzimidazol-5-yl)methyl)amine.

$^1$H NMR (CDCl$_3$, 2 sets of signals): δ1.20, 1.40, 1.55, 1.70, 1.90, 2.35, 2.45, 2.70, and 2.80 (all m, together 11H); 7.10, 7.25, and 7.30 (all m, together 16H).

Step 3: 1-Cyclohexyl-3-((1-triphenylmethyl-4,5,6,7-tetrahydro-1H-benzimidazol-5-yl)methyl)thiourea and 1-cyclohexyl-3-((3-triphenylmethyl-4,5,6,7-tetrahydro-3H-benzimidazol-5-yl)methyl)thiourea

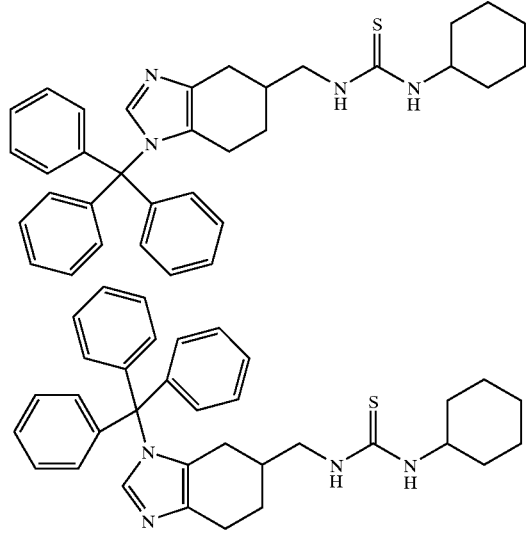

Cyclohexylisothiocyante (0.45 ml, 3.05 mmol) was added at 0° C. to a mixture of ((1-triphenylmethyl-4,5,6,7-tetrahydro-1H-benzimidazol-5-yl)methyl)amine and ((3-triphenylmethyl-4,5,6,7-tetrahydro-3H-benzimidazol-5-yl)methyl]amine (0.60 g, 1.53 mmol) in DCM (5 ml). The reaction mixture was stirred for 3 hours at 0° C. The solvent was removed in vacuo. The crude product was purified by flash chromatography on silica (90 g), using a mixture of DCM/methanol/ammonia (100:10:1) as eluent, to give 770 mg of a mixture of 1-cyclohexyl-3-((1-triphenylmethyl-4,5,6,7-tetrahydro-1H-benzimidazol-5-yl)methyl)thiourea and 1-cyclohexyl-3-((3-triphenylmethyl-4,5,6,7-tetrahydro-3H-benzimidazol-5-yl)methyl)thiourea. $^1$H NMR (CDCl$_3$, 2 sets of signals): δ1.00–2.20 (m, 15H): 2.30, 2.75, and 2.85 (dd, m, and dd, together 3H); 3.00–3.20 (m, 2H); 7.10, 7.25, and 7.35 (all m, together 16H).

Step 4:

A solution of a mixture of 1-cyclohexyl-3-((1-triphenylmethyl-4,5,6,7-tetrahydro-1H-benzimidazol-5-yl)methyl)thiourea and 1-cyclohexyl-3-((3-triphenylmethyl-4,5,6,7-tetrahydro-3H-benzimidazol-5-yl)methyl)thiourea (770 mg, 1.44 mmol) in acetic acid (5 ml) and water (0.6 ml) was heated to 90° C. for 2 hours. The solvent was removed in vacuo. The crude product was purified by flash chromatography on silica (40 g), using a mixture of DCM/methanol/25% aqueous ammonia (100:10:1) as eluent, to give 400 mg of the title compound, HPLC method C: elution at 8.58 min. MS: calc for [M+H]$^+$: 293; Found: 293. $^1$H NMR (CDCl$_3$): δ1.20, 1.35, 1.45, 1.60, 1.70, 1.90, 2.00, 2.05, 2.20, and 2.60 (all m, together 18H); 3.40 and 3.60 (both m, together 2H); 7.40 (s, 1H).

For biological testing, the title compound was transferred into its hydrochloride salt by dissolving the title compound in ethyl acetate (30 ml) and addition of a 3.5 M solution of hydrogen chloride in ethyl acetate (3 ml). The precipitation was collected and dried. Microanalysis for $C_{15}H_{24}N_4S$, HCl, H$_2$O; Calc: C: 51.93%; H: 7.84%; N: 16.15%; Found: C: 51.36%; H: 8.05%; N: 14.84%.

Example 62

3-(4-Chlorophenyl)-N-((4,5,6,7-tetrahydro-1H-benzimidazol-5-yl)methyl)-propionamide

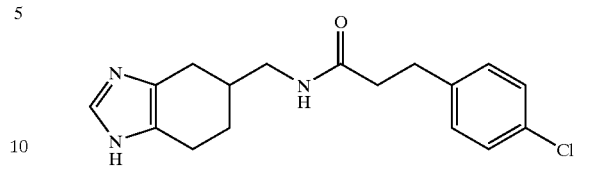

Step 1: 3-(4-Chlorophenyl)-N-((1-triphenylmethyl-4,5,6,7-tetrahydro-1H-benzimidazol-5-yl)methyl)propionamide and 3-(4-chlorophenyl)-N-((3-triphenylmethyl-4,5,6,7-tetrahydro-3H-benzimidazol-5-yl)methyl)propionamide

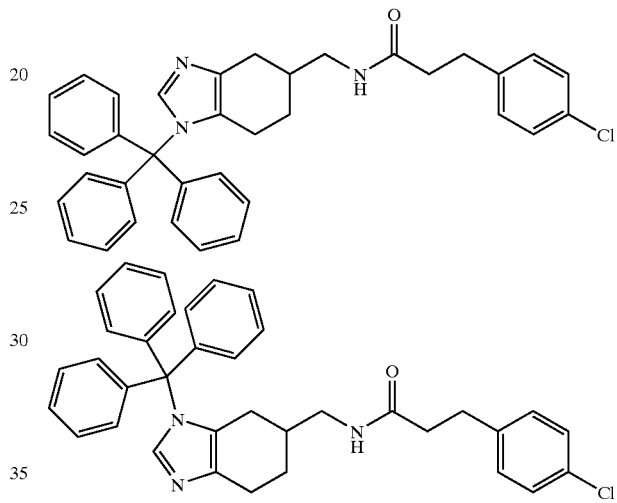

At 0° C., 1-(3-dimethylaminopropyl)-3-ethylcarbodiimide (0.29 g, 1.53 mmol) was added to a solution of 3-(4-chlorophenyl)propionic acid (0.28 g, 1.53 mmol) and 1-hydroxy-enzotriazole (0.23 g, 1.53 mmol). The reaction mixture was stirred for 20 min at 0° C. A mixture of ((1-triphenylmethyl-4,5,6,7-tetrahydro-1H-benzimidazol-5-yl)methyl)amine and ((3-triphenylmethyl-4,5,6,7-tetrahydro-3H-benzimidazol-5-yl)methyl)amine (0.60 g, 1.53 mmol) and ethyldisopropylamine (0.287 ml, 1.68 mmol) were added successively. The reaction mixture was stirred at room temperature for 16 hours. It was diluted with ethyl acetate (100 ml) and washed with a saturated aqueous solution of sodium hydrogencarbonate (100 ml). The aqueous phase was extracted with ethyl acetate (3×60 ml). The combined organic layers were washed with water (100 ml) and dried over magnesium sulphate. The solvent was removed in vacuo. The crude product was purified by flash chromatography on silica (40 g), using a mixture of DCM/methanol/25% aqueous ammonia (100:10:1) as eluent, to give 0.69 g of a mixture of 3-(4-chlorophenyl)-N-((1-triphenylmethyl-4,5,6,7-tetrahydro-1H-benzimidazol-5-yl)methyl)propionamide and 3-(4-chlorophenyl)-N-((3-triphenylmethyl-4,5,6,7-tetrahydro-3H-benzimidazol-5-yl)methyl)propionamide. $^1$H NMR (CDCl$_3$, 2 sets of signals) δ1.15, 1.35, 1.45, 1.70, 1.85, 2.30, 2.45, 2.60, 2.70, 2.80, 2.90 (all m, together 11H); 3.00 and 3.30 (both m, together 2H); 5.05 and 5.65 (both t, together 1H); 7.00–7.40 (m, 20H).

Step 2:

A solution of a mixture of 3-(4-chlorophenyl)-N-((1-triphenylmethyl-4,5,6,7-tetrahydro-1H-benzimidazol-5-yl)

methyl)propionamide and 3-(4-chlorophenyl)-N-((3-triphenylmethyl-4,5,6,7-tetrahydro-3H-benzimidazol-5-yl)methyl)propionamide (0.69 g, 1.23 mmol) in acetic acid (5 ml) and water (0.6 ml) was heated to 90° C. for 1.5 hours. The solvent was removed in vacuo. The crude product was purified by flash chromatography on silica (40 g), using DCM/methanol/25% aqueous ammonia (100:10:1) as eluent, to give 0.42 g of the title compound. HPLC method C: elution at 8.04 min. MS: calc for [M+H]$^+$: 318; Found: 318. $^1$NMR (CDCl$_3$): δ1.35 (m, 1H); 1.80 (m, 1H); 1.90 (m, 1H); 2.15 (dd, 1H); 2.50 (t, 2H); 2.55 (m, 3H); 2.90 (t, 2H); 3.10 and 3.25 (both m, together 2H); 6.45 (t, 1H); 7.10 (d, 2H); 7.20 (m, 2H); 7.40 (s, 1H).

For biological testing, the title compound was transferred into its hydrochloride salt by dissolving the title compound in ethyl acetate (30 ml) and addition of a 3.5 M solution of hydrogen chloride in ethyl acetate (3 ml). The precipitation was collected and dried. Microanalysis for $C_{17}H_{20}ClN_3O$, HCl, 2H$_2$O; Calc: C: 52.31%; H: 6.46%; N: 10.77%; Found: C: 52.95%; H: 6.22%; N: 10.49%.

Example 63

2-(4-Chlorophenyl)-N-((4,5,6,7-tetrahydro-1H-benzimidazol-5-yl)methyl)acetamide.

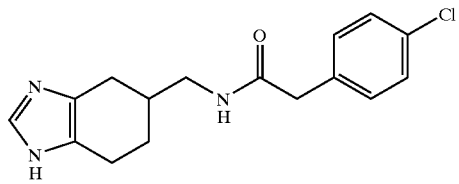

Step 1: 2-(4-Chlorophenyl)-N-((1-triphenylmethyl-4,5,6,7-tetrahydro-1H-benzimidazol-5-yl)methyl)acetamide and 2-(4-chlorophenyl)-N-((3-triphenylmethyl-4,5,6,7-tetrahydro-3H-benzimidazol-5-yl)methyl)acetamide

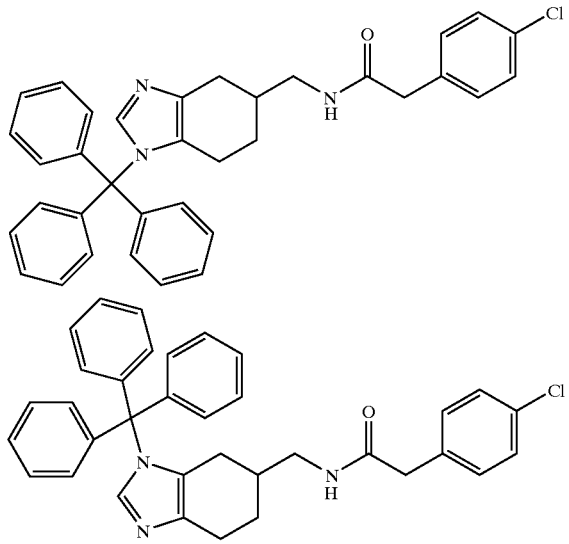

At 0° C. 1-(3-dimethylaminopropyl)-3-ethylcarbodiimide (0.17 g, 0.89 mmol) was added to a solution of 4-chlorophenylacetic acid (0.15 g, 0.89 mmol) and 1-hydroxybenzotriazole (0.14 g, 0.89 mmol) in N,N-dimethylformamide. The reaction mixture was stirred for 20 min at 0° C. A mixture of ((1-triphenylmethyl-4,5,6,7-tetrahydro-1H-benzimidazol-5-yl) methyl)amine and ((3-triphenylmethyl-4,5,6,7-tetrahydro-3H-benzimidazol-5-yl)methyl)amine (0.35 g, 0.89 mmol) and ethyldiisopropylamine (0.17 ml, 0.98 mmol) were added successively. The reaction mixture was stirred for 3 days. It was diluted with ethyl acetate (100 ml) and washed with a saturated aqueous solution of sodium hydrogencarbonate (100 ml). The aqueous phase was extracted with ethyl acetate (3×60 ml). The combined organic layers were washed with water (100 ml) and dried over magnesium sulphate. The solvent was removed in vacuo. The crude product was purified by flash chromatography on silica (40 g), using first ethyl acetate/heptane (1:1, 200 ml) and subsequently a mixture of DCM/methanol25% aqueous ammonia (100:10:1) as eluent, to give 0.38 g of a mixture of 2-(4-chlorophenyl)-N-((1-triphenylmethyl-4,5,6,7-tetrahydro-1H-benzimidazol-5-yl)methyl)acetamide and 2-(4-chlorophenyl)-N-((3-triphenylmethyl-4,5,6,7-tetrahydro-3H-benzimidazol-5-yl)methyl)acetamide. $^1$H NRM (CDCl$_3$): δ0.90 (m, 1H); 1.25 (m, 1H); 1.75 (m, 3H); 2.60 (m, 3H); 3.15 (m, 1H); 3.40 (s, 2H); 5.05 (t, 1H); 6.90–7.45 (m, 20H).

Step 2:

A solution of a mixture of 2-(4-chlorophenyl)-N-((1-triphenylmethyl-4,5,6,7-tetrahydro-1H-benzimidazol-5-yl)methyl)acetamine and 2-(4-chlorophenyl)-N-((3-triphenylmethyl-4,5,6,7-tetrahydro-3H-benzimidazol-5-yl)methyl)acetamide (0.38 g, 0.80 mmol) in a mixture of acetic acid (5 ml) and water (0.6 ml) was heated to 90° C. for 2 hours. The solvent was removed in vacuo. The crude product was purified by flash chromatography on silica (40 g), using a mixture of DCM/methanol/25% aqueous ammonia (100:10:1) as eluent, to give 0.18 g of the title compound. HPLC method C: elution at 7.31 min. MS: calc for [M+H]$^+$: 304; Found: 304. $^1$H NMR (DMSO-d$_6$) δ1.35 (m, 1H); 1.85 (m, 2H); 2.15 (dd, 1H); 2.50 (m, 3H); 3.05 (m, 2H); 3.45 (s, 2H); 7.25 (d, 2H); 7.35 (m, 3H); 8.15 (t, 1H); 11.60 (br, 1H). Microanalysis for $C_{16}H18ClN_3O$, 0.25 H$_2$O: Calc: C:62.34%; H: 6.05%; N: 13.63%; Found: C: 62.05%; H: 6.08%; N: 13.35%.

For biological testing, the title compound was transformed into its hydrochloride salt by lyophilization of a solution of title compound in 0.1 N hydrochloric acid (20 ml).

Example 64

4-(4-Chlorophenyl)-N-((4,5,6,7-tetrahydro-1H-benzimidazol-5-yl)methyl)butyramide

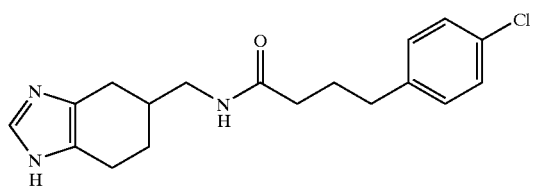

Step 1: 4-(4-Chlorophenyl)-N-((1-triphenylmethyl-4,5,6,7-tetrahydro-1H-benzimidazol-5-yl)methyl)butyramide and 4-(4-chlorophenyl)-N-((3-triphenylmethyl-4,5,6,7-tetrahydro-3H-benzimidazol-5-yl)methyl)butyramide

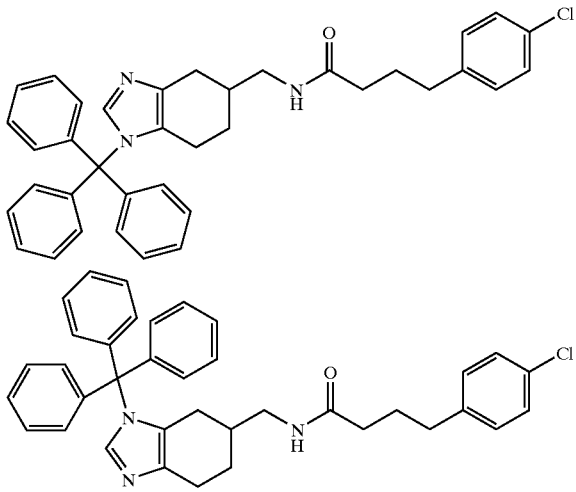

At 0° C. 1-(3-dimethylaminopropyl)-3-ethylcarbodiimide (0.16 g, 0.84 mmol) was added to a solution of 4-(4-chlorophenyl)butyric acid (0.17 g, 0.84 mmol) and 1-hydroxy-benzotriazole (0.13 g, 0.84 mmol) in DCM (3 ml) and N,N-dimethylformamide (3 ml). The reaction mixture was stirred for 20 min at 20° C. A mixture of ((1-triphenylmethyl-4,5,6,7-tetrahydro-1H-benzimidazol-5-yl)methyl)amine and ((3-triphenylmethyl-4,5,6,7-tetrahydro-3H-benzimidazol-5-yl)methyl)amine (0.33 g, 0.84 mmol) was added. Ethyldiisopropylamine (0.16 ml, 0.92 mmol) was added. The reaction mixture was stirred for 16 hours at room temperature. It was diluted with ethyl acetate (100 ml) and washed with a saturated aqueous solution of sodium hydrogencarbonate (100 ml). The aqueous phase was extracted with ethyl acetate (3×60 ml). The combined organic layers were washed with water (100 ml) and dried over magnesium sulphate. The solvent was removed in vacuo. The crude product was purified by flash chromatography on silica (40 g), using ethyl acetate/heptane (1:1; 300 ml) and successively DCM/methanol/25% aqueous ammonia (100:10:1) as eluent, to give 0.43 g of a mixture of 4-(4-chlorophenyl)-N-((1-triphenylmethyl-4,5,6,7-tetrahydro-1H-benzimidazol-5-yl)methyl)butyramide and 4-(4-chlorophenyl)-N-((3-triphenylmethyl-4,5,6,7-tetrahydro-3H-benzimidazol-5-yl)methyl)butyramide. $^1$H NMR CDCl$_3$): δ1.05 (m, 1H); 1.50 (m, 1H); 1.65–2.10 (m, 6H); 2.50–2.80 (m, 3H); 2.85 (m, 2H); 3.10 (m, 2H); 5.00 (t, 1H); 7.10 (m, 7H); 7.25 (m, 13H).

Step 2:
A solution of a mixture of 4-(4-chlorophenyl)-N-((1-triphenylmethyl-4,5,6,7-tetrahydro-1H-benzimidazol-5-yl)methyl)butyramide and 4-(4-chlorophenyl)-N-((3-triphenylmethyl-4,5,6,7-tetrahydro-3H-benzimidazol-5-yl)methyl)butyramide (0.43 g, 0.72 mmol) in acetic acid (5 ml) and water (0.6 ml) was heated to 90° C. for 2 hours. The solvent was removed in vacuo. The crude product was purified by flash chromatography on silica (40 g), using DCM/methanol/25% aqueous ammonia (100:10:1) as eluent, to give 0.21 g of the title compound. HPLC method C: elution at 8.52 min. MS: calc for [M+H]$^+$: 332; Found: 332. $^1$H NMR (DMSO-d$_6$) δ1.50 (m, 1H); 2.00 (m, 4H); 2.20 (m, 2H); 2.30 (dd, 1H); 2.65 (m, 5H); 3.25 (m, 1H); 3.35 (m, 1H); 5.96 (t, 1H); 7.20 (d, 2H); 7.25 (d, 2H); 7.45 (s, 1H).

For biological testing, the title compound was transferred into its hydrochloride salt by dissolving the title compound in ethyl acetate (30 ml) and addition of a 3.5 M solution of hydrogen chloride in ethyl acetate (3 ml). The precipitation was collected and dried.

Example 65

4,5,6,7-Tetrahydro-1H-benzimidazole-5-carboxylic acid [3-(4-chlorophenyl)-propyl]amide, hydrochloride

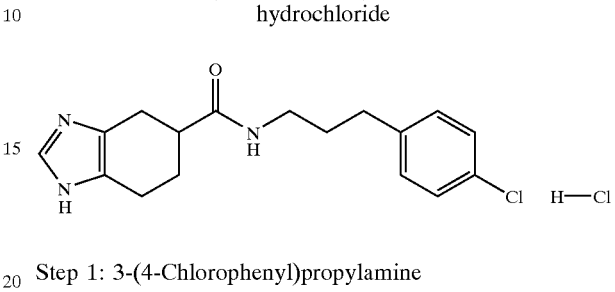

Step 1: 3-(4-Chlorophenyl)propylamine

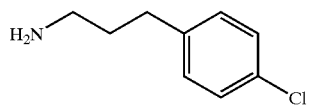

The potassium salt of phthalimide (4.4 g, 24 mmol) was dissolved in DMF (20 ml) and 1-chloro-4-(3-bromopropyl)benzene (4.67 g, 20 mmol) was added. The mixture was stirred at 80° C. for 16 hours. Water (50 ml) and DCM (50 ml) were added, the phases were separated and the aqueous phase extracted with DCM (2×50 ml). The combined organic phases were washed with sodium hydroxide (0.2 M, 50 ml), dried (magnesium sulphate), filtered and concentrated in vacuo. Ethanol (75 ml) and hydrazine hydrate (2 equiv.) were added and the mixture was heated to reflux for 2 hours. After cooling the mixture was filtrated and the filter cake washed with DCM (2×50 ml). The filtrate washings were evaporated and dissolved in ethyl acetate (40 ml). Washing of the organic phase with sodium hydroxide (0.4 M, 2×25 ml) and water (2×25 ml) followed by drying (magnesium sulphate), filtration and evaporation gave 3-(4-chlorophenyl)propylamine. $^1$H NMR (CDCl$_3$): δ1.82–1.50 (m, 4H); 2.78–2.53 (m, 4H); 7.32–6.96 (m, 4H).

Step 2:
To a slurry of 4,5,6,7-tetrahydrobenzimidazole-5-carboxylic acid hydrochloride (202.6 mg, 1 mmol) in DMF (5 ml) was added 1-hydroxybenzotriazole (137 mg, 1 mmol). The mixture was cooled on an ice bath and 1-(3-dimethylaminopropyl)-3-ethylcarbodiimide hydrochloride (192 mg, 1 mmol) was added. After stirring for 1 hour, 3-(4-chlorophenyl)propylamine (170 mg, 1 mmol) and diisopropylethyl amine (0.38 ml, 2.2 mmol) were added. The mixture was stirred at room temperature for 16 hours. Ethyl acetate (50 ml) and sodium hydrogen carbonate (50 ml) were added. The phases were separated and the aqueous phase was extracted with ethyl acetate (2×50 ml).

The combined aqueous phases were washed with water (75 ml), dried (magnesium sulphate), filtrated and concentrated in vacuo. Flash chromatography (40 g SiO$_2$), eluent DCM, methanol and aqueous ammonia (25%)100:10:1 followed by evaporation gave the pure amide. This was dissolved in ethyl acetate, HCl in ether was added in excess and the mixture stirred for 1 hour. Evaporation gave the title compound as a white powder. Mp.=146–148° C. $^1$H NMR (DMSO-d$_6$) δ2.11–1.58 (m, 4H); 2.80–2.47 (m, 7H); 3.18–2.97 (m, 2H); 7.23 (d, J=8 Hz, 2H); 7.36 (d, J=8 Hz, 2H); 8.13 (t, J=4.5 Hz, 1H); 8.88 (s, 1H); 14.23 (br s, 1H). Microanalysis for $C_{17}H_{20}N_3OCl$, HCl; Calc: C, 57.63%; H, 5.97%; N, 11.86%; Found: C, 57.64%; H, 6.08%, N, 11.75%.

Example 66

4,5,6,7-Tetrahydro-1H-benzimidazole-5-carboxylic acid (2-benzimidazol-1-yl-ethyl)amide, hydrochloride

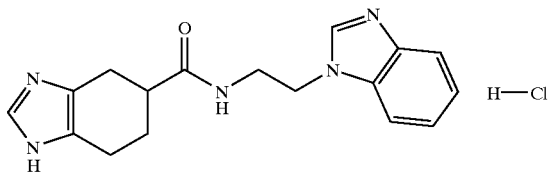

By a similar procedure as described in Example 65, the title compound was prepared from 4,5,6,7-tetrahydrobenzimidazole-5-carboxylic acid and 3-benzimidazol-1-yl-ethylamine. $^1H$ NMR (DMSO-$d_6$) δ1.92–1.60 (m, 2H); 2.70–2.36 (m, 5H); 3.49 (q, J=5.75, 2H); 4.34 (t, J=5.75, 2H); 7.30–7.15 (m, 2H); 7.69–7.58 (m, 2H); 8.06 (t, J=5 Hz, 1H); 8.14 (s, 1H). Microanalysis for $C_{17}H_{19}N_5O$, HCl, 0.25 $H_2O$ Calc: C, 58.28%; H, 5.90%; N, 19.99% Found: C, 58.62%; H, 6.13%; N, 19.59%.

Example 67

4,5,6,7-Tetrahydro-1H-benzimidazole-5-carboxylic acid (3-benzimidazol-1-yl-propyl)amide, hydrochloride

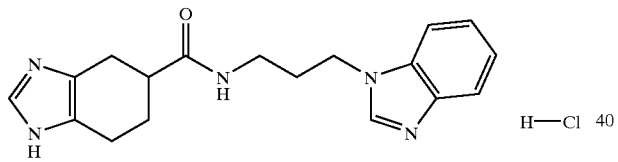

By a similar procedure as described in Example 65, the title compound was prepared from 4,5,6,7-tetrahydrobenzimidazole-5-carboxylic acid and 3-benzimidazol-1-yl-propylamine. $^1H$ NMR (DMSO-$d_6$) δ2.07–1.79 (m, 4H); 2.80–2.58 (m, 5H); 3.08 (q, J=6.3, 2H); 4.30 (t, J=7.0, 2H); 7.24 (p, J=7.0, 2H); 7.64 (t, J=7.3, 2H); 8.29 (t, J=5.3, 1H); 8.32 (s, 1H); 8.83 (s, 1H). LC-MS m/z 324.1 (M+H)$^+$, rt=0.35, purity=99.1%.

Example 68

4,5,6,7-Tetrahydro-1H-benzimidazole-5-carboxylic acid (3-phenylallyl)amide, hydrochloride

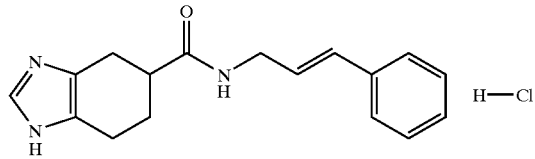

By a similar procedure as described in Example 65, the title compound was prepared from 4,5,6,7-tetrahydrobenzimidazole-5-carboxylic acid and 3-phenylallylamine.

$^1H$ NMR (DMSO-$d_6$) δ2.11–1.63 (m, 2H); 2.66–2.53 (m, 5H); 3.89 (t, J=5.5 Hz, 2H); 6.25 (dt, J=16 and 5.5 Hz, 1H); 6.50 (d, J=16 Hz, 1H); 7.45–7.18 (m, 5H); 8.00 (s, 1H): 8.22 (t, J=5.5 Hz, 1H). LC-MS m/z 282.1 (M+H)$^+$, rt=1.19, purity=97.3% Microanalysis for $C_{17}H_{19}N_3O$, 0.75 HCl Calc: C, 66.14%; H, 6.45%; N, 13.61% Found: C, 66.24%; H, 6.71%; N, 13.25%

Example 69

4,5,6,7-Tetrahydro-1H-benzimidazole-5-carboxylic acid (5-phenylpentyl)amide, hydrochloride

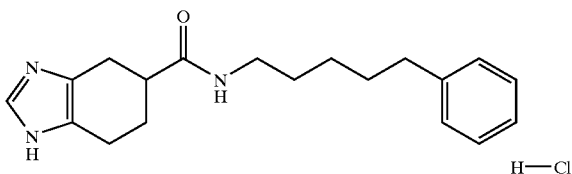

Step 1: 5-Phenylpentylamine

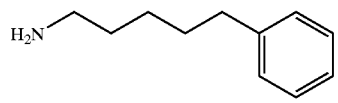

The amine was prepared by a similar procedure as described in Example 65, Step 1 from 5-bromopentylbenzene. $^1H$ NMR (CDCl$_3$): δ1.16 (s, 2H); 1.73–1.25 (m, 6H); 2.69–2.54 (m, 4H); 7.31–7.10 (m, 5H).

Step 2:

By a similar procedure as described in Example 65, the title compound was prepared from 4,5,6,7-tetrahydrobenzimidazole-5-carboxylic acid and 5-phenylpentylamine.

$^1H$ NMR (DMSO-$d_6$) δ12.01–1.23 (m, 8H); 2.69–2.50 (m, 7H); 3.06 (p, J=5.5 Hz, 2H); 7.22 (m, 5H); 8.02 (t, J=5.5 Hz, 1H); 8.87 (s, 1H); 14.24 (s, 1H), LC-MS m/z 312 (M+H)$^+$, rt=2.55, purity 94.5%. Microanalysis for $C_{19}H_{25}N_3O$·HCl Calc: C, 65.60%; H, 7.53%; N, 12.08% Found: C, 65.72%; H, 7.84%, 11.9%

Example 70

4,5,6,7-Tetrahydro-1H-benzimidazole-5-carboxylic acid (4-phenoxybutyl]amide, hydrochloride

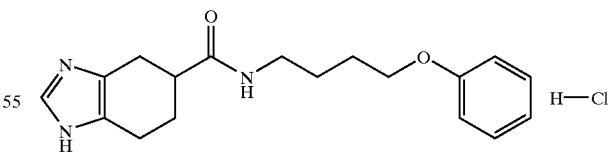

Step 1: 4-Phenoxybutylamine

The N-(4-Phenoxybutylamine

The N-(4-bromobutyl)phthalimide (4.232 g, 15 mmol) was dissolved in DMF (15 ml) and phenol (1.411 g, 15 mmol) and potassium carbonate (2.073 g, 15 mmol) was added. The mixture was stirred at 65° C. for 16 hours. Sodium hydroxide (5%, 25 ml) was added and the aqueous phase was extracted with ethyl acetate (3×25 ml). Drying (magnesium sulphate), filtration and evaporation gave the phthalimide-protected intermediate. Ethanol (65 ml) and hydrazine hydrate (2 equiv.) were added and the mixture was heated to reflux for 2 hours. After cooling the mixture was filtrated and the filter cake washed with DCM (2×50 ml). The filtrate and washings were concentrated in vacuo and dissolved in ethyl acetate. Washing of the organic phase with sodium hydroxide (0.4 M, 2×25 ml) and water (2×25 ml) followed by drying (magnesium sulphate), filtration and evaporation gave 4-phenoxybutylamine. $^1$H NMR (CDCl$_3$): δ1.08 (s, 2H); 1.89–1.57 (m, 4H); 2.76 (t, J=7 Hz, 2H); 3.95 (t, J=6.5 Hz, 2H); 6.90 (m, 3H); 7.30 (m, 2H).

Step 2:

By a similar procedure as described in Example 65, the title compound was prepared from 4,5,6,7-tetrahydrobenzimidazole-5-caboxylic acid and 4-phenoxybutylamine. $^1$H NMR (DMSO-d$_6$) δ2.13–1.49 (m, 6H); 2.81–2.47 (m, 5H); 3.28–3.01 (m, 2H); 3.95 (t, J=6 Hz, 2H); 6.95–6.87 (m, 3H); 7.27 (t, J=8 Hz, 2H); 8.25 (t, J=5.5, 1H); 8.92 (s, 1H); 14.48 (br s, 1H). LC-MS m/z 314.2 (M+H)$^+$, rt=2.14, purity=99.2%). Microanalysis for C$_{18}$H$_{23}$N$_3$O$_2$.HCl: Calc: C, 61.80%; H, 6.91%, N, 12.01% Found: C, 61.50%; H, 7.10%; N, 11.81%.

Example 71

4,5,6,7-Tetrahydro-1H-benzimidazole-5-carboxylic acid [3-(4-chlorophenoxy)-propyl]amide, hydrochloride

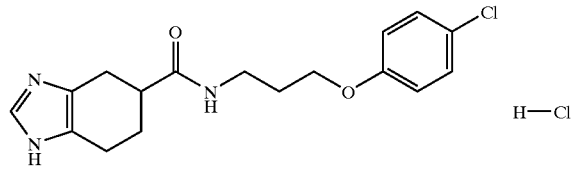

Step 1: 3-(4-Chlorophenoxy)propylamine

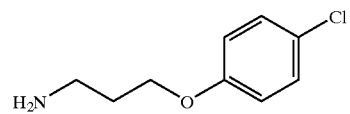

The amine was prepared by a similar procedure as described in Example 70, Step 1, from N-(3-bromopropyl) phthalimide and 4-chlorophenol. $^1$H NMR (CDCl$_3$): δ2.03–1.67 (m, 4H); 2.92 (t, 2H, J=6.0 Hz); 4.02 (t, 2H, J=6.0 Hz); 6.83 (m, 2H); 7.24 (m, 2H).

Step 2:

By a similar procedure as described in Example 65, the title compound was prepared from 4,5,6,7-tetrahydrobenzimidazole-5-carboxylic acid and 3-(4-chlorophenoxy)-propylamine. $^1$H NMR (CD$_3$OD) δ2.20–1.88 (m, 4H); 2.90–2.65 (m, 5H); 3.41 (q, J=6 Hz, 2H); 4.01 (t, J=6 Hz, 2H); 6.89 (d, J=9 Hz, 2H); 7.22 (d, J=9 Hz, 2H); 8.18 (br s, 1H); 8.66 (s, 1H). LC-MS m/z 335 (M+H)$^+$, rt 2.21, purity=99.6%. Microanalysis for C$_{17}$H$_{20}$N$_3$O$_2$Cl.HCl containing 0.4 equiv. H$_2$O: Calc: C, 54.09% ; H, 5.79%; N, 11.19% Found: C, 54.15%; H, 5.80%; N, 11.03%.

Example 72

4,5,6,7-Tetrahydro-1H-benzimidazole-5-carboxylic acid [3-(3-chlorophenoxy)-propyl]amide, hydrochloride

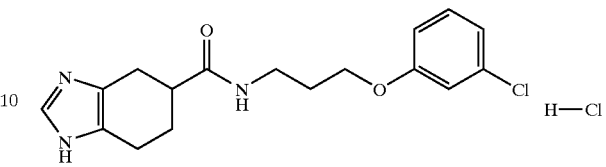

Step 1: 3-(3-Chlorophenoxy)propylamine

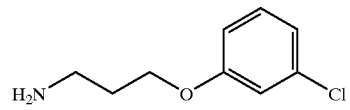

The amine was prepared by a similar procedure as described in Example 70, Step 1, from N-(3-bromopropyl) phthalimide and 3-chlorophenol. $^1$H NMR (CDCl$_3$): δ1.59 (br s, 2H); 2.03–1.82 (m, 2H); 2.88 (t, J=7 Hz; 4.01 (t, J=7 Hz, 2H); 6.95–6.70 (m, 3H); 7.25–7.11 (m, 1H).

Step 2:

By a similar procedure as described in Example 65, the title compound was prepared from 4,5,6,7-tetrahydrobenzimidazole-5-carboxylic acid and 3-(3-chlorophenoxy)-propylamine $^1$H (DMSO-d$_6$) δ2.11–1.66 (m, 4H); 2.77–2.10 (m, 5H); 3.58–3.12 (m, 2H); 4.02 (t, J=4.5 Hz, 2H); 7.03–6.88 (m, 3H); 7.30 (t, J=8 Hz, 1H); 8.24 (t, J=5.5, 1H); 8.88 (s, 1H); 14.82–14.00 (br s, 1H). LC-MS m/z 334.1 (M+H)$^+$, rt=2.33, purity=97.7%. Mircoanalysis for C$_{17}$H$_{20}$N$_3$O$_2$Cl.HCl: Calc: C, 55.14%; H, 5.72%; N, 11.35%; Found: C, 55.22%; H, 5.71%; N, 11.28%.

Example 73

4,5,6,7-Tetrahydro-1H-benzimidazole-5-carboxylic acid [4-(4-methylphenoxy)-butyl]amide, hydrochloride

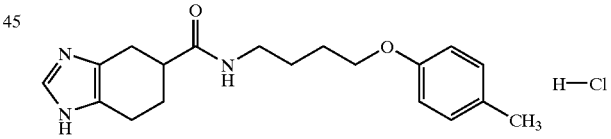

Step 1: 4-(4-Methylphenoxy)butylamine

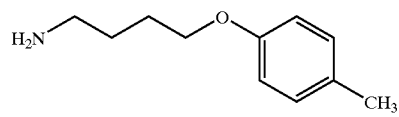

The amine was prepared by a similar procedure as described in Example 70, Step 1, from N-(4-bromobutyl) phthalimide and 4-methylphenol. $^1$H NMR (CDCl$_3$): δ1.09 (s, 2H); 1.69 (m, 4H); 2.30 (s, 2H); 2.74 (t, 2H, J=6.90 Hz); 3.93 (t, 2H, J=6.27 Hz); 6.71 (m, 3H); 7.12 (m, 1H).

Step 2:

By a similar procedure as described in Example 65, the title compound was prepared from 4,5,6,7-tetrahydrobenzimidazole-5-carboxylic acid and 4-(4- methylphenoxy)-butylamine. ¹H NMR (DMSO-d₆); δ1.55–2.12 (m, 6H); 2.22 (s, 3H); 2.71–2.55 (m, 5H); 3.15–3.10 (m, 2H); 3.92 (t, J=6.2, 2H); 6.80, (d, J=8.5, 2H); 7.07 (d, J=8.5, 2H); 8.11 (t, J=5.6, 1H); 8.88 (s, 1H); 14.29 (s, 2H). LC-MS m/z 328.2 (M+H)⁺, rt=2.41, purity 98.1%. Microanalysis for $C_{19}H_{25}N_3O_2 \cdot HCl$: Calc: C, 62.71%; H, 7.20%, N, 11.55%; Found: C, 62.55%; H, 7.34%; N, 11.45%;

Example 74

4,5,6,7-Tetrahydro-1H-benzimidazole-5-carboxylic acid [4-(3-methylphenoxy)-butyl]amide, hydrochloride

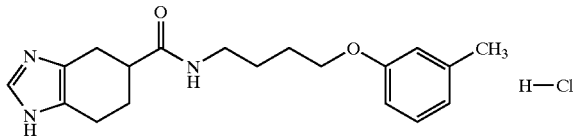

Step 1: 4-(3-Methylphenoxy)butylamine

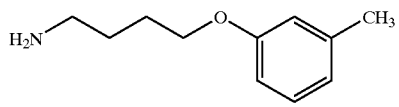

The amine was prepared by a similar procedure as described in Example 70, Step 1, from N-(4-bromobutyl) phthalimide and 3-methylphenol. ¹H NMR (CDCl₃): δ1.21 (s, 2H); 1.52–1.90 (m, 4H); 2.27 (s, 3H); 2.75 (t, 3H, J=6.90 Hz); 3.92 (t, 3H, J=6.27 Hz); 6.79 (d, 2H, J=8.53 Hz); 7.06 (d, 2H, J=8.28 Hz).

Step 2:

By a similar procedure as described in Example 65, the title compound was prepared from 4,5,6,7-tetrahydrobenzimidazole-5-carboxylic acid and 4-(3-methylphenoxy)-butylamine. ¹H NMR (DMSO-d₆): δ1.43–2.12 (m, 6H); 2.24(s, 3H); 2.55–2.79 (m, 5H); 3.05 (m, 2H); 3.95 (t, J=6 Hz, 2H); 6.72 (m, 3H); 7.12 (t, J=7.91 Hz, 1H); 8.08 (t, J=5.5 Hz, 1H); 8.79 (s, 1H); 14.30 (br s, 1H). LC-MS m/z 328.2 (M+H)⁺, rt=2.45, purity 78.1%. Microanalysis for $C_{19}H_{25}N_3O_2 \cdot HCl$:

Calc: C, 62.71%; H, 7.20%, N, 11.55%; Found: C, 62.48%; H, 7.32%; N, 11.38%.

Example 75

4,5,6,7-Tetrahydro-1H-benzimidazole-5-carboxylic acid (5 phenoxypentyl) amide, hydrochloride

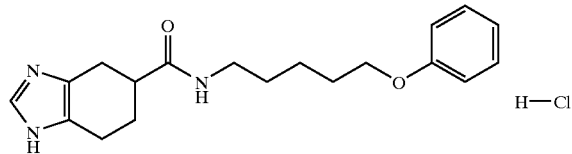

Step 1; 5-Phenoxypentylamine

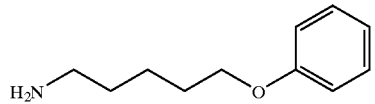

The amine was prepared by a similar procedure as described in Example 70, Step 1, from N-(5-bromopentyl) phthalimide and phenol.

¹H NMR (CDCl₃): δ1.10 (s, 2H); 1.40–1.58 (m, 4H); 1.77(t, 2H, J=6.65 Hz); 2.68 (t, 2H, J=6.65 Hz); 3.94 (t, 2H, J=6.40 Hz); 6.87 (m, 3H); 7.25 (m, 2H).

Step 2:

By a similar procedure as described in Example 65, the title compound was prepared from 4,5,6,7-tetrahydrobenzimidazole-5-carboxylic acid and 5-phenoxypentylamine.

¹H NMR (DMSO-d₆) δ1.40–2.10 (m, 8 H); 2.52–2.70 (m, 5H); 3.07–3.12 (m, 2H); 3.94 t, J=6.4, 2H); 6.89–6.94 (m, 3H); 7.23–7.31 (m, 2H); 8.10 (t, J=5.5, 1 H); 8.89 (s, 1H); 14.37 (br s, 2H). LC-MS m/z 328.2 (M+H)⁺, rt=2.38, purity 98.6%. Microanalysis for $C_{19}H_{25}N_3O_2$ containing 1.35 equiv HCl:

Calc: C, 55.24%; H, 6.67%; N, 10.17% Found: C, 55.29%: H, 6.62%, N, 10.08%.

Example 76

4,5,6,7-Tetrahydro-1H-benzimidazole-5-carboxylic acid [5-(naphth-1-yloxy)-pentyl]amide, hydrochloride

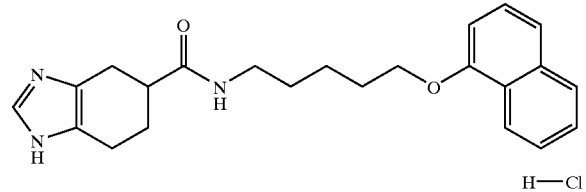

Step 1: 5-(Naphth-1-yloxy)pentylamine

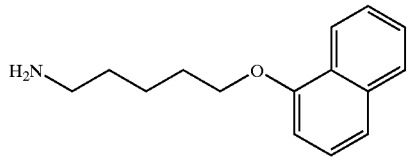

The amine was prepared by a similar procedure as described in Example 70, Step 1, from N-(5-bromopentyl) phthalimide and 1-naphthol.

¹H NMR (CDCl₃): δ1.32(s, 2H); 1.68–1.59 (m, 4H); 1.81–1.95 (m, 2H); 2.64 (t, J=6.53 Hz, 2H); 4.04 (t, J=6.27 Hz, 2H): 6.71–6.77 (m, 1H); 727–750 (m, 4H): 7.72–7.80 (m, 1H); 8.26–8.32 (m, 1H).

Step 2:

By a similar procedure as described in Example 65, the title compound was prepared from 4,5,6,7-tetrahydrobenzimidazole-5-carboxylic acid and 5-(naphth-1-yloxy)pentyl amine.

¹H NMR (DMSO-d₆) δ1.48–1.60 (m, 4H); 1.69–2.09 (m, 4 H); 2.54–2.86 (m, 2H); 2.66–2.76 (m, 2H): 3.06–3.19 (m, 2H); 4.15 (t, J=6.3 Hz, 2H); 6.94–6.98 (dd, 1H); 7.36–7.53 (m, 4H); 7.84–7.88 (m, 1H); 8.07 (t, J=5.5 Hz, 1 H);

8.14–8.19 (m, 1H); 8.87 (s, 1H); 14.21(br s, 1H). LC-MS m/z 378.3 (M+H)$^+$, rt=2.98, purity 100%. Microanalysis for $C_{23}H_{27}N_3O_2$, HCl:

Calc: C, 66.74%; H, 6.82%; N, 10.15% Found: C, 66.31%: H, 7.07%. N, 9.97%.

Example 77

4,5,6,7-Tetrahydro-1H-benzimidazole-5-carboxylic acid (2-benzimidazol-1-yl ethyl)methylamide, hydrochloride

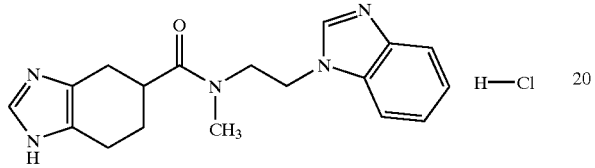

Step 1: (2-Benzimidazol-1-yiethyl)methylamine

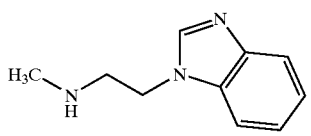

2-Benzimidazol-1-yiethylamine (1.612 g, 10 mmol) was refluxed in ethyl formate (4.9 ml, 60 mmol) for 2 hours and concentrated in vacuo. The residue was dissolved in THF (30 ml) and added drop-wise to a cooled 1 M solution of lithium aluminium hydride (30 ml). The mixture was heated to reflux for 1.5 hours. After cooling a solution of sodium sulphate (0.5 g in 10 ml water) was added, the mixture was stirred over night and a white precipitate was formed. Filtration followed by evaporation of the filtrate gave the crude product. Flash chromatography (40 g SiO$_2$, eluent CH$_2$Cl$_2$, MeOH, NH$_4$ (25%) 100:10:1) gave the desired amine.

$^1$H NMR (CDCl$_3$): δ1.59 (br s, 1 H); 2.43 (s, 3H); 3.04 (t, J=6 Hz, 2H); 4.30 (t, J=6 Hz, 2H); 7.22–7.48 (m, 3H); 7.76–7.68 (m, 1H); 7.96 (s, 1H).

Step 2:

By a similar procedure as described in Example 65, the title compound was prepared from 4,5,6,7-tetrahydrobenzimidazole-5-carboxylic acid and (2-benzimidazol-1-yl-ethyl) methylamine.

$^1$H NMR (DMSO-d$_6$) δ1.08–2.72 (m, 7H); 2.90 and 2.99 (two singlets due to two isomers (s, 3H)); 3.68–3.92 (m, 2H); 4.58 (t, J=5.5 Hz, 2H); 7.24–7.52 (m, 2H); 7.62–7.91 (m, 2H); 8.52 and 8.88 (two singlets due to two isomers (s, 1H); 8.82 and 8.97 (two singlets due to two isomers (s, 1H)); 14.40 (br s, 1H). EVSP MS m/z 323.2 (M)$^+$.

Example 78

4,5,6,7-Tetrahydro-1H-benzimidazole-5-carboxylic acid (3-benzimidazol-1-yl-propyl)methylamide, hydrochloride

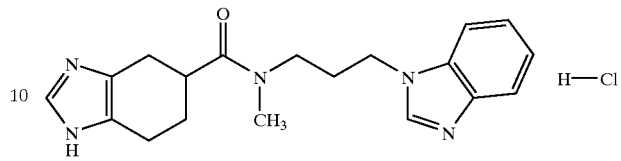

Step 1: (3-Benzimidazol-1-yl-propyl)methylamine

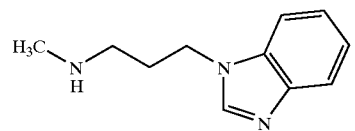

The amine was prepared by a similar procedure as described in Example 77, Step 1 from 3-benzimidazol-1-yl-propylamine.

$^1$H NMR (CDCl$_3$): δ2.00 (p, J=7 Hz, 2H); 2.56 (t. J=7 Hz, 2H); 4.30 (t, J=7 Hz, 2H); 7.21–7.49 (m, 3H); 7.72–7.84 (m, 1H); 7.90 (s, 1H).

Step 2:

By a similar procedure as described in Example 65, the title compound was prepared from 4,5,6,7-tetrahydrobenzimidazole-5-carboxylic acid and (3-benzimidazol-1-yl propyl) methylamine.

$^1$H NMR (DMSO-d$_6$) δ1.48–2.78 (m, 9H). 2.82 and 3.09 (two singlets due to two isomers (s, 3H)); 3.30–3.56 (m, 2H); 4.36–4.59 (m, 2H); 7.45–7.64 m 2H); 7.75–8.06 (m, 2H); 8.91 (s, 1H); 9.50 and 9.57 (two singlets due to two isomers (s, 1 H)); 14.45 (br s, 1H). EI/SP MS m/z 337.2 (M)$^+$ Example 79

4,5,6,7-Tetrahydro-1 H-benzimidazole-5-carboxylic acid (3-benzotriazole-1-yl propyl)methylamide, hydrochloride

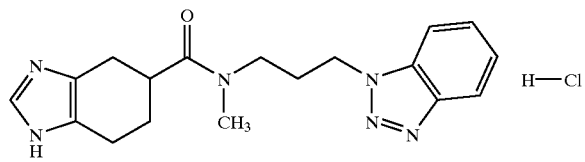

Step 1: (3-Benzotriazol-1-yl-propyl)methylamine

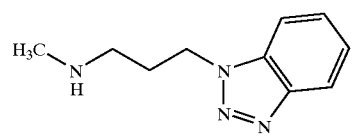

The amine was prepared by a similar procedure as described in Example 77, Step 1 from 3-benzotriazol-1-N-propylamine.

$^1$H NMR (CDCl$_3$): δ1.61 (br s, 1H); 1.68 (s, 1H); 2.06–2.27 (m, 2H); 2.43 (s, 3H); 2.59 (t, J=7 Hz, 2H); 4.74 (t, J=7 Hz, 2H); 7.22–7.61 (m, 3H); 8.00–8.09 (m, 2 H).

Step 2:

By a similar procedure as described in Example 65, the title compound was prepared from 4,5,6,7-tetrahydrobenzimidazole-5-carboxylic acid and (3-benzotriazol-1-yl propyl)methylamine.

$^1$H NMR (DMSO-d$_6$) δ11.48–2.75 (m, 9H): 2.80 and 3.05 (two singlets due to two isomers (s, 3H)); 3.26–3.53 (m, 2H); 4.62–4.84 (m, 2H); 7.28–7.62 (m 2H); 7.83–8.09 (m, 2H): 9.91 (s, 1H); 14.40 (br s, 1H). EVSP MS m/z 338.2 (M)$^+$ 339.2 (M+1)$^+$.

Example 80

4,5,6,7-Tetrahydro-1H-benzimidazole-5-carboxylic acid [3-(4-chlorophenyl)-propyl]methylamide, hydrochloride

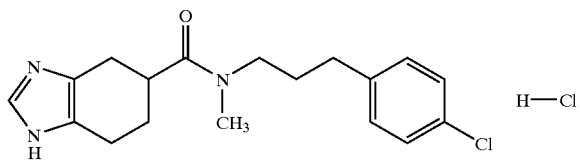

Step 1: 3-(4-Chlorophenyl)propylmethylamine

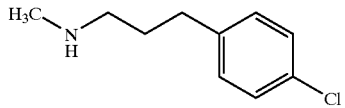

The amine was prepared by a similar procedure as described in Example 77, Step 1 from 3-(4-chlorophenyl) propylamine.

$^1$H NMR (CDCl$_3$): δ1.18 (s, 1H) 1.63–1.86 (m, 2H); 239 (s, 3H): 2.47–2.68 (m, 4H); 7.00–7.24 (m, 4H).

Step 2:

By a similar procedure as described in Example 65, the title compound was prepared from 4,5,6,7-tetrahydrobenzimidazole-5-carboxylic acid and 3-(4-chlorophenyl)propylmethylamine.

$^1$H NMR (DMSO-d$_6$) δ1.56–2.10 (m, 4H). 2.42–3.46 (m, 2H); 2.82 and 3.06 (two singlets due to two isomers (s, 3H)); 7.18–7.39 (m, 4H); 8.89 (s, 1H); 14.56 (s, 1H). LC-MS m/z 332.1 (M+H)$^+$, rt=244, purity=81.8%). EI/SP MS m/z 331.2/ 333.2 (M)$^+$.

Example 81

4,5,6,7-Tetrahydro-1H-benzimidazole-5-carboxylic acid methyl(5-phenylpentyl)-amide, hydrochloride

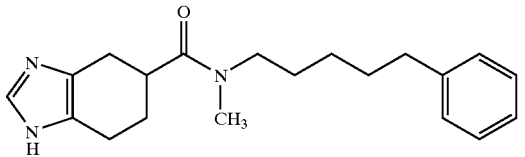

Step 1: 5-Phenylpentylmethylamine

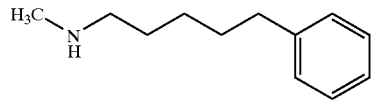

The amine was prepared by a similar procedure as described in Example 77, Step 1 from 5-phenylpentylamine.

$^1$H NMR (CDCl$_3$): δ1.18 (s, 1H); 1.37–1.70 (m, 6H); 2.39(s, 3H); 2.53–2.63 (m, 4H); 7.10–7.28 (m, 5H).

Step 2:

By a similar procedure as described in Example 66, the title compound was prepared from 4,5,6,7-tetrahydrobenzimidazole-5-carboxylic acid and 5-phenylpentylmethylamine as an yellow oil.

$^1$H NMR (DMSO-d$_6$) δ1.12–2.00 (m, 8H); 2.45–2.72 (m, 7H); 2.82 and 3.03 (two singlets due to two isomers (s, 3H)); 3.06–3.48 (m, 2H); 7.06–7.31 (m, 5H); 8.86 (s, 1H); 14.30 (br s, 1H). LC-MS m/z 326.2 (M+H)$^+$, rt=2.86, purity= 99.7%.

Example 82

4,5,6,7-Tetrahydro-1H-benzimidazole-5-carboxylic acid [3-(4-chlorophenoxy)-propyl]methylamide hydrochloride Step 1: 3-(4-Chlorophenoxy)propylmethylamine The amine was prepared by a similar procedure as described in Example 77, Step 1 from 3-(4-chlorophenoxy) propylamine.

$^1$H NMR (CDCl$_3$): δ173 (s, 1H); 1.72–2.02 (m, 2H; 2.42 (s, 3H); 2.70 (t, J=7 Hz, 2H); 3.96 (t, J=6.5 Hz, 2H); 6.78 (d, J=9 Hz, 2H); 7.19 (d, J=9 Hz, 2H.

Step 2:

By similar procedure as described in Example 65, the title compound was prepared from 4,5,6,7-tetrahydrobenzimidazole-5-carboxylic acid and 3-(4-chlorophenoxy)-propylmethylamine.

$^1$H NMR (DMSO-d$_6$) δ1.56–2.07 (m, 4H). 2.55–2.78 (m, 5H); 2.85 and 3.07 (two singlets due to two isomers (s, 3H)); 3.22–3.68 (m, 2H); 3.85–4.06 (m, 2H); 6.82–7.01 (m, 2H); 7.19–7.39 (m, 2H); 8.85 and 8.87 (two singlets due to two isomers (s, 1H)); 14.30 (br s, 1H). LC-MS m/z 348.1 (M+H)$^+$, rt=2.32, purity=96.5%. Microanalysis for C$_{18}$H$_{22}$N$_3$O$_2$Cl, HCl containing 0.25 equiv. H$_2$O:

Calc: C, 55.61%; H, 6.09%; N, 10.81%; Found: C, 55.34%, H, 6.04%, N, 11.19%.

Example 83

4,5,6,7-Tetrahydro-1H-benzimidazole-5-carboxylic acid [3-(3-chlorophenoxy)-propyl]methylamide, hydrochloride

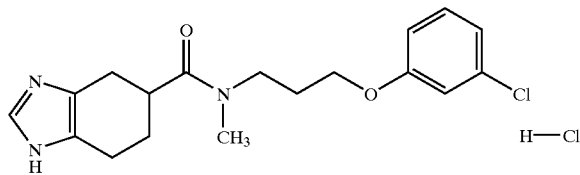

Step 1: 3-(3-Chlorophenoxy)propylmethylamine

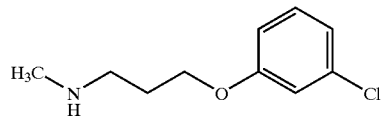

The amine was prepared by a similar procedure as described in Example 77, Step 1 from 3-(3-chlorophenoxy) propylamine.

$^1$H NMR (CDCl$_3$): δ1.82–2.04 (m, 2H). 2.32 (br s, 1H); 2.45 (s, 3H); 2.72 (t, J=7 Hz, 2H); 3.98 (t, J=6 Hz, 2H); 6.70–6.96 (m, 3H); 7.08–7.22 (m, 1 H).

Step 2:

By a similar procedure as described in Example 65, the title compound was prepared from 4,5,6,7-tetrahydrobenzimidazole-5-carboxylic acid and 3-(3-chlorophenoxy)-propylmethylamine.

$^1$H NMR (DMSO-d$_6$) δ1.57–2.04 (m, 4H); 2.53–2.75 (m, 3H); 3.10 and 3.16 (two singlets from the two isomers of the methyl amide, (s, 3H)); 3.22–3.61(m, 4H); 4.0 (t, J=4.5 Hz, 2H); 6.81–7.02 (m, 3H); 7.20–7.37 (m, 1H); 8.86 and 8.88 (two singlets due to two isomers (s, 1H)); 14.44 (br s, 2H),LC-MS m/z 348.1 (M+H)$^+$, rt=2.33, purity=92.4%.

Example 84

4,5,6,7-Tetrahydro-1H-benzimidazole-5-carboxylic acid (4-phenoxybutyl]-methylamide, hydrochloride

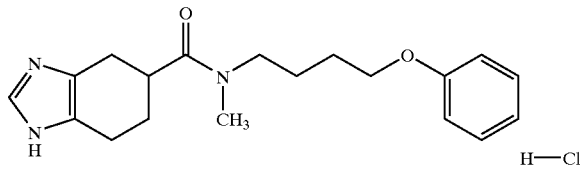

Step 1: 4-Phenoxybutylmethylamine

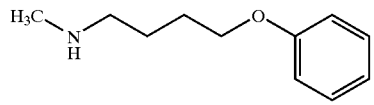

The amine was prepared by a similar procedure as described in Example 77, Step 1 from 4-phenoxybutylamine.

$^1$H NMR (CDCl$_3$): δ1.60–1.92 (m, 4H); 2.45 (s, 3H); 2.66 (t, J=7.0 Hz, 2H); 3.96 (t, J=6.5 Hz, 2H); 6.85–7.01 (m, 3H): 7.23–7.35 (m, 2H).

Step 2:

By a similar procedure as described in Example 65, the title compound was prepared from 4,5,6,7-tetrahydrobenzimidazole-5-carboxylic acid and 4-phenoxybutylmethyl-amino as an yellow oil.

$^1$H NMR (DMSO-d$_6$) δ1.60–2.08 (m, 7H). 2.52–2.75(m, 2H); 3.05 and 3.18 (two singlets from the two isomers of the methyl amide, (s, 3H)); 3.21–3.51(s, 4H); 3.97(m, 2H); 6.83–6.95 (m, 3H); 7.18–7.32 (m, 2H); 8.81 and 8.86 (two singlets due to two isomers (s, 1H)); 14.21(s, 1H). LC-MS m/z 328.1(M+H)$^+$, rt=2.20, purity=99.6%.

Example 85

4,5,6,7-Tetrahydro-1-H-benzimidazole-5-carboxylic acid [4-(4-methylphenoxy)-pentyl]methylamide, hydrochloride

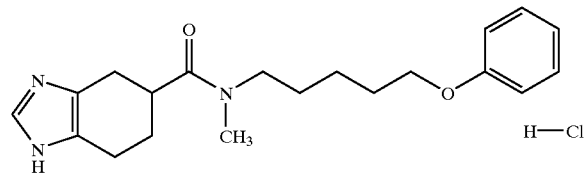

Step 1: 5-Phenoxypentylmethylamine

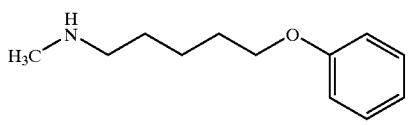

The amine was prepared by a similar procedure as described in Example 77, Step 1 from 5-phenoxypentylamine.

$^1$H NMR (CDCl$_3$): δ1.14 (br s, 1H); 1.51 (m, 4H); 1.79 (p, J=6.8 Hz, 2H); 2.41(s, 3H); 2.59 (t, J=6.7 Hz, 2H); 3.94 (t, J=6.5 Hz, 2H); 6.86–6.95 (m, 3H); 7.22–7.30 (m, 2H).

Step 2:

By a similar procedure as described in Example 65, the title compound was prepared from 4,5,6,7-tetrahydrobenzimidazole-5-carboxylic acid and 5-phenoxypentylmethylamine $^1$H NMR (DMSO-d$_6$) δ1.31–2.07 (m, 8H); 2.55–2.79 (m, 5H); 2.80 and 3.08 (two singlets from the two isomers of the methyl amide (s, 3H); 322–3.49 (m, 2H); 3.87–4.01 (m, 2H); 6.81–6.98 (m, 3H); 7.21–7.33 (m, 2H); 8.87(s, 1H); 14.23(s, 1H). LC-MS m/z 342.3 (M+H)$^+$, rt=2.60, purity=93.7%).

Microanalysis for C$_{20}$H$_{27}$N$_3$O$_2$.HCl:

Calc: C, 63.56%; H, 7.47%; N, 11.12%;. Found: C, 63.39%; H, 7.65%; N, 11.00%.

Example 86

4,5,6,7-Tetrahydro-1-H-benzimidazole-5-carboxylic acid methyl-(4-(4-methylphenoxy)butyl)amide, hydrochloride

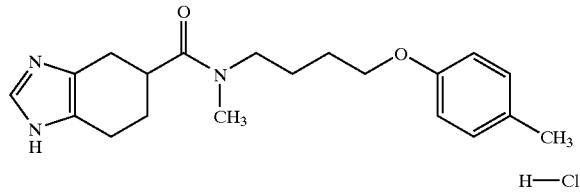

Step 1: Methyl-4-(4-methylphenoxy) butylamine

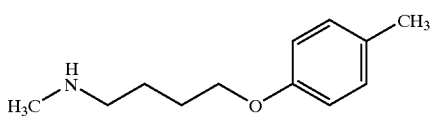

The amine was prepared by a similar procedure as described in Example 77, Step 1 from 4-(4-methylphenoxy) butylamine.

$^1$H NMR (CDCl$_3$): δ1.54–1.88 (m, 4H); 2.21(s, 1H); 2.27 (s, 3H); 2.43 (s, 3H); 2.60 (t, J=7.03 Hz, 2H); 3.94 (t, J=6.27 Hz, 2H); 6.74–6.82 (m, 2H); 7.01–7.10 (m, 2H).

Step 2:

By a similar procedure as described in Example 65, the title compound was prepared from 4,5,6,7-tetrahydrobenzimidazole-5-carboxylic acid end methyl-4-methylphenoxy)butylamine.

$^1$H NMR (DMSO-d$_8$) δ1.55–2.05 (m, 6H); 2.22 (s, 3H); 2.56–2.77 (m, 4H); 2.85 and 3.05 (two singlets from the two isomers of the methyl amide (s, 3H); 3.38–3.55 (m, 2H); 3.88–3.99 (m, 2H); 6.74–8.82 (m, 2H); 7.00–7.09 (m, 2H); 8.87(s, 1H); 14.16(br s, 1H). LC-MS m/z 343.1 (M+H)$^+$, rt=2.54.

Example 87

4,5,6,7-Tetrahydro-1H-benzimidazole-5-carboxylic acid methyl-(4-(3-methylphenoxy)butyl)amide, hydrochloride

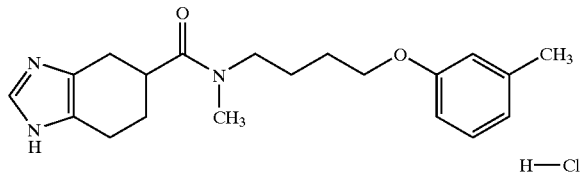

Step 1: Methyl-(4-(3-methylphenoxy)butylamine

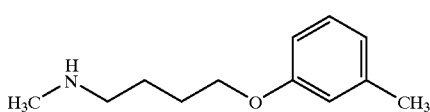

The amine was prepared by a similar procedure as described in Example 77, Step 1 from 4-(3-methylphenoxy) butylamine.

$^1$H NMR (CDCl$_3$): δ1.61–1.89 (m, 4H); 2.32 (s, 3H); 2.43 (s, 3H); 2.62 (t, J=7 Hz, 2H); 3.92(t, J=6 Hz, 2H): 6.78–7.65 (m, 3H); 7.10–7.18 (m, 1H).

Step 2:

By a similar procedure as described in Example 65, the title compound was prepared from 4,5,6,7-tetrahydrobenzimidazole-5-carboxylic acid and methyl-(4-(3-methylphenoxy)butylamine.

$^1$H NMR (DMSO-d$_8$) δ1.54–2.05(m, 6H); 2.26 (d, J=4.3 Hz, 3H); 2.55–2.77 (m, 4H); 2.85 and 3.05 (two singlets from the two isomers of the methyl amide (s, 3H); 3.35–3.51 (m, 2H); 3.90–4.03 (m, 2H); 6.64–6.77 (m, 3H); 7.07–7.18 (m, 1H); 8.86(s, 1H); 14.19 (br s, 1H). LC-MS m/z 342.3 (M+H)$^+$, rt=2.52, purity=100%).

Example 88

Tetrahydro-1H-benzimidazole-5-carboxylic acid methyl-[5-(naphth-1-yloxy)pentyl]amide, hydrochloride

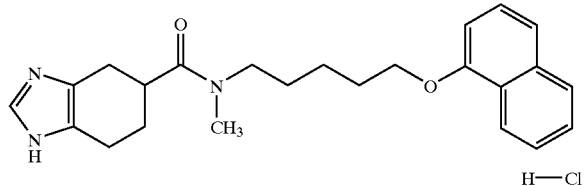

Step 1: Methyl-[5-(naphth-1-yloxy)pentyl]amine

The amine was prepared by a similar procedure as described in Example 77, Step 1 from 5-(naphth-1-yloxy) pentylamine.

$^1$H NMR (CDCl$_3$): δ1.54–1.61 (m, 4H); 1.84–1.97 (m, 2H); 2.41 (s, 3H); 252–2.64 (m, 3H); 4.08 (t, J=6.3 Hz, 2H); 6.72–6.77 (dd, 1H); 7.30–7.50 (m, 4H); 7.71–7.80 (m, 1H); 8.23–8.30 (m, 1H).

Step 2:

By a similar procedure as described in Example 65, the title compound was prepared from 4,5,6,7-tetrahydrobenzimidazole-5-carboxylic acid and methyl-[5-(naphth-1-yloxy)pentyl ]amine.

$^1$H NMR (DMSO-d$_8$) δ1.41–2.06 (m, 8H); 2.59–2.78 (m, 4H); 285 and 3.05 (two singlets from the two isomers of the methyl amide (s, 3H); 3.35–3.59 (m, 2H); 4.11–4.21 (m, 2H); 6.94–6.98 (dd, 1H); 7.35–7.58 (m, 4H); 7.82–7.89 (m, 1H); 8.11–8.20 (m, 1H); 8.87(s, 1H); 14.11 (br s, 1H). LC-MS m/z 392.2 (M+H)$^+$, rt=3.12.

Example 89

4,5,6,7-Tetrahydro-1H-benzimidazole-4-carboxylic acid 2-chlorobenzylamide, hydrochloride

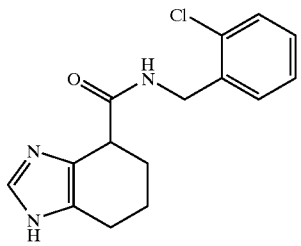

Using the same procedure as described for Example 65, the title compound was obtained from 4,5,6,7-tetrahydro-1H-benzimidazole-4-carboxylic acid and 2-chlorobenzylamine. Mp. 165–167° C. $^1$H NMR (DMSO-d$_6$) δ1.70–1.98 (m, 3H), 2.12 (m, 1H), 2.62 (m, 2H), 3.78 (m, 1H), 4.29 (dd, J=7 Hz, 17 Hz, 1H), 4.47 (dd, J=7 Hz, 17 Hz, 1H) 7.28–7.48 (m, 4H), 8.69 (brs, 1H), 8.92 (s, 1H), 14.20 (brs, 2H). HPLC-MS: m/z×290 (MH$^+$).

Example 90

4,5,6,7-Tetrahydro-1H-benzimidazole-4-carboxylic acid benzylmethylamide, hydrochloride

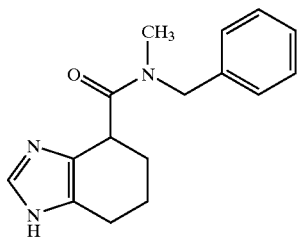

Using the same procedure as described for example 65, the title compound was obtained from 4,5,6,7-tetrahydro-1H-benzimidazole-4-carboxylic acid and methyl(benzyl)amine. Mp. 211–213° C. $^1$H NMR (DMSO-d$_6$) δ1.69–1.94 (m, 3H), 2.02–2.19 (m, 1H), 2.62 (m, 2H), 2.81 and 3.07 (2xs, 3H), 4.29 (m, 1H), 4.41, 4.66, 4.68, and 4.83 (4xd, J=17 Hz, 2H), 7.22–7.45 (m, 5H), 8.92 and 8.95 (2x s, 1H), 14.24 (s, 2H). HPLC-MS: m/z×270 (MH$^+$).

Example 91

4,5,6,7-Tetrahydro-1H-benzimidazole-4-carboxylic acid phenethylamide, hydrochloride

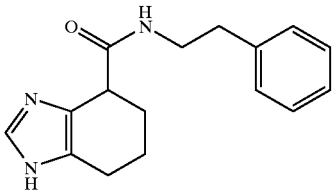

Using the same procedure as described for example 65, the title compound was obtained from 4,5,6,7-tetrahydro-1H-benzimidazole-4-carboxylic acid and (2-phenylethyl)amine. Mp 177–179° C. $^1$H NMR (DMSO-d$_6$) δ1.63–1.89 (m, 3H) 1.98 (m, 1H) 2.58 (m, 2H) 2.75 (t, J=7 Hz. 2H) 3.19–3.48 (m, 2H) 3.63 (t, J=5 Hz, 1H) 7.19–7.32 (m, 5H). 8.29 (t, J=5 Hz, 1H) 8.92 (s, 1H), 14.25 (s, 2H). HPLC-MS: m/z×270 (MH$^+$).

Example 92

([4,5,6,7-Tetrahydro-1H-benzimidazol-4-yl]methyl) amine

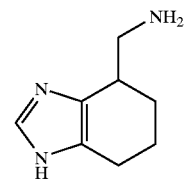

and 2-(4,5,6,7-Tetrahydro-1H-benzimidazol-4-yl) ethylamine

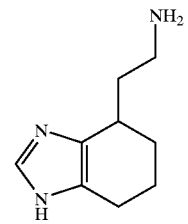

were prepared using a similar procedure as described for Example 52.

By using a similar procedure as described for Example 4 these amines were linked to an insoluble polystyrene resin, acid converted into the amides given in the table below. These amides were isolated, analyzed and tested as trifluoroacetate salts.

| Example | Name | Found MH$^+$ |
| --- | --- | --- |
| 92-001 | 7-Oxo-7-phenylheptanoic acid [2-(4,5,6,7-tetrahydro-1H-benzimidazol-4-yl)ethyl]-amide | 368 |

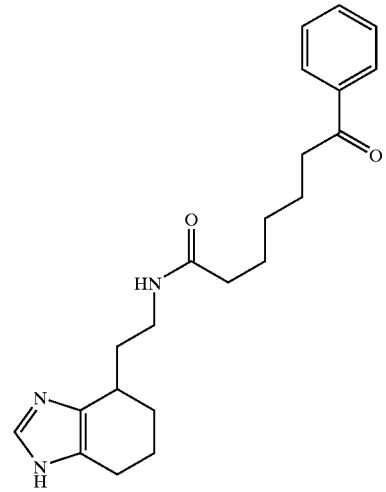

-continued

| Example | Name | Found MH+ |
|---|---|---|
| 92-002 | 3-(4-Chlorophenyl)-N-[2-(4,5,6,7-tetrahydro-1H-benzimidazol-4-yl)ethyl]propionamide | |

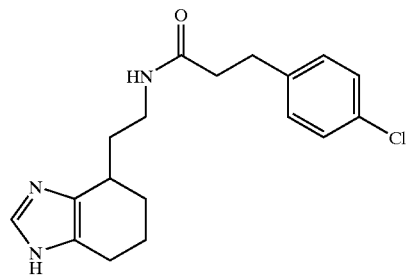

| | | |
|---|---|---|
| 92-003 | 4-(4-Chlorophenyl)-N-[2-(4,5,6,7-tetrahydro-1H-benzimidazol-4-yl)ethyl]butyramide | 346 |

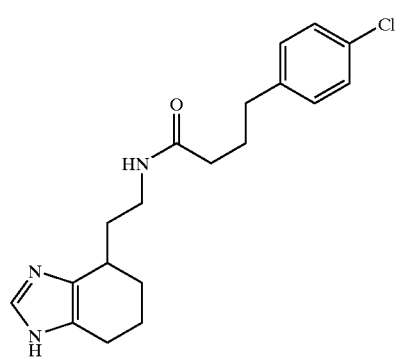

| | | |
|---|---|---|
| 92-004 | 6-Phenylhexanoic acid [2-(4,5,6,7-tetrahydro-1H-benzimidazol-4-yl)ethyl]amide | |

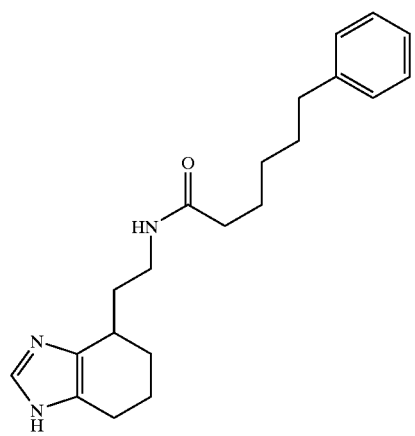

-continued

| Example | Name | Found MH+ |
|---|---|---|
| 92-005 | 2-(2-Chlorophenyl)-N-[2-(4,5,6,7-tetrahydro-1H-benzimidazol-4-yl)ethyl]acetamide | 318 |

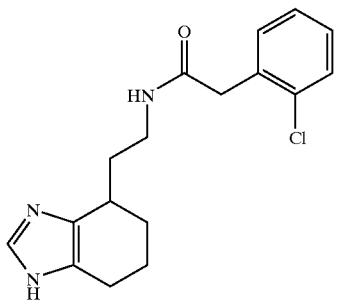

| | | |
|---|---|---|
| 92-006 | 4-Chloro-N-[2-(4,5,6,7-tetrahydro-1H-benzimidazol-4-yl)ethyl]benzamide | |

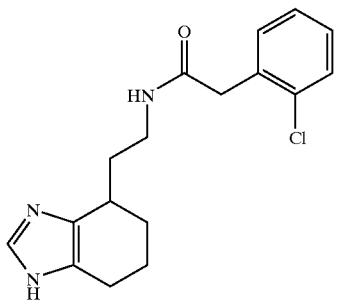

| | | |
|---|---|---|
| 92-007 | 2-Naphth-2-yl-N-[2-(4,5,6,7-tetrahydro-1H-benzimidazol-4-yl)ethyl]acetamide | 334 |

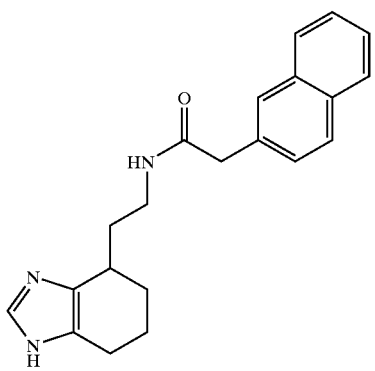

-continued

| Example | Name | Found MH+ |
|---|---|---|
| 92-008 | 5-Phenylpentanoic acid [2-(4,5,6,7-tetra-hydro-1H-benzimidazol-4-yl)-ethyl]amide | |

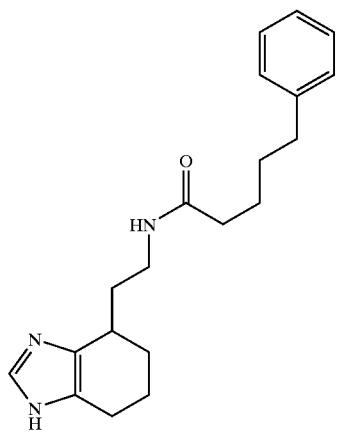

| 92-009 | 2-(4-Chlorophenyl)-N-[2-(4,5,6,7-tetrahydro-1H-benzimidazol-4-yl)ethyl]acetamide | 318 |

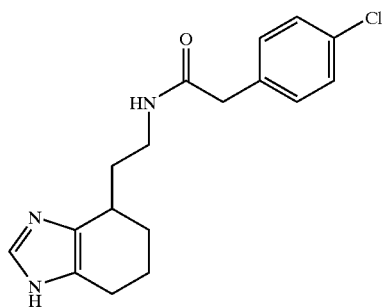

| 92-010 | 2-Naphth-1-yl-N-[2-(4,5,6,7-tetrahydro-1H-benzimidazol-4-yl)ethyl]acetamide | |

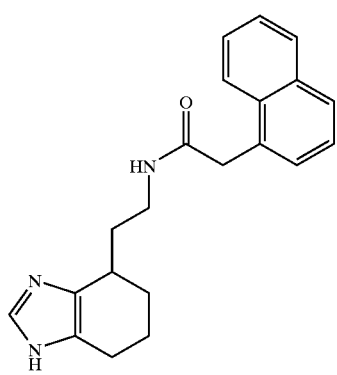

-continued

| Example | Name | Found MH+ |
|---|---|---|
| 92-011 | 7-Oxo-7-phenyheptanoic acid (4,5,6,7-tetrahydro-1H-benzimidazol-4-ylmethyl)-amide | |

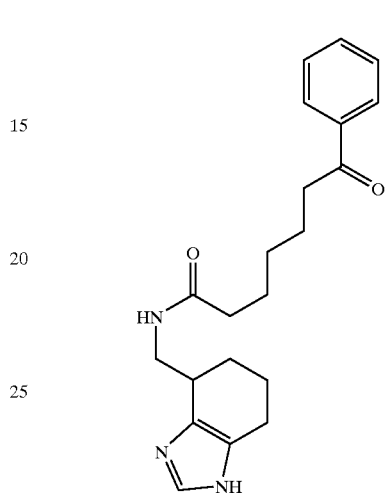

| 92-012 | 3-(4-Chlorophenyl)-N-(4,5,6,7-tetrahydro-1H-benzimidazol-4-ylmethyl)propionamide | 318 |

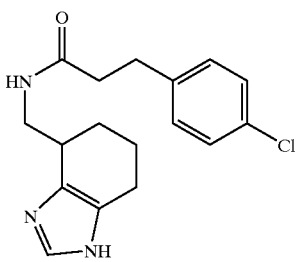

| 92-013 | 4-(4-Chlorophenyl)-N-(4,5,6,7-tetrahydro-1H-benzimidazol-4-ylmethyl)butyramide | |

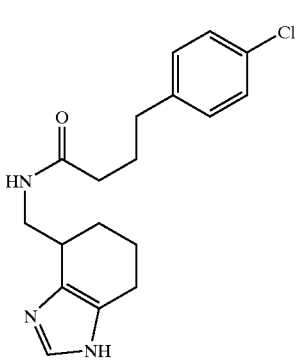

-continued

| Example | Name | Found MH+ |
|---|---|---|
| 92-014 | 6-Phenylhexanoic acid (4,5,6,7-tetrahydro-1H-benzimidazol-4-ylmethyl)amide | 326 |

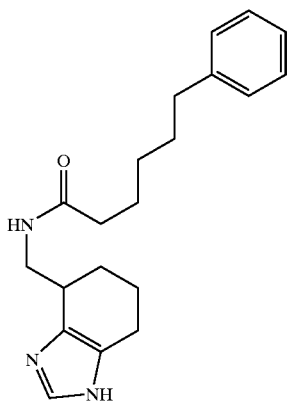

| Example | Name | Found MH+ |
|---|---|---|
| 92-015 | 2-(2-Chlorophenyl)-N-(4,5,6,7-tetrahydro-1H-benzimidazol-4-ylmethyl)acetamide | |

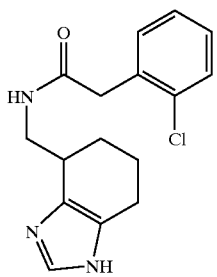

| Example | Name | Found MH+ |
|---|---|---|
| 92-016 | 4-Chloro-N-(4,5,6,7-tetrahydro-1H-benzimidazol-4-ylmethyl)benzamide | 290 |

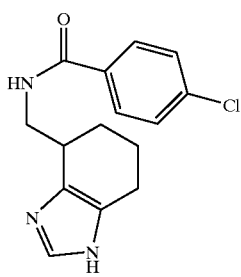

| Example | Name | Found MH+ |
|---|---|---|
| 92-017 | 2-Naphth-2-yl-N-(4,5,6,7-tetrahydro-1H-benzimidazol-4-ylmethyl)acetamide | |

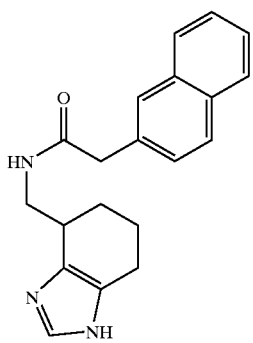

-continued

| Example | Name | Found MH+ |
|---|---|---|
| 92-018 | 5-Phenylpentanoic acid (4,5,6,7-tetrahydro-1H-benzimidazol-4-ylmethyl)amide | 312 |

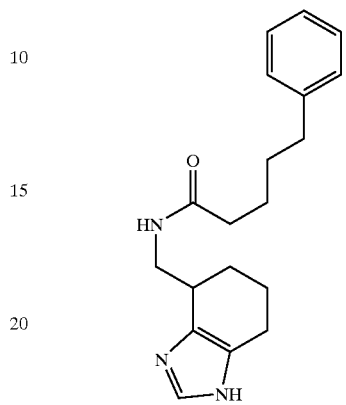

| Example | Name | Found MH+ |
|---|---|---|
| 92-019 | 2-(4-Chlorophenyl)-N-(4,5,6,7-tetrahydro-1H-benzimidazol-4-ylmethyl)acetamide | |

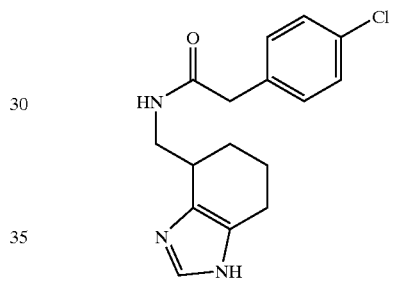

| Example | Name | Found MH+ |
|---|---|---|
| 92-020 | 2-Naphth-1-yl-N-(4,5,6,7-tetrahydro-1H-benzimidazol-4-ylmethyl)acetamide | 320 |

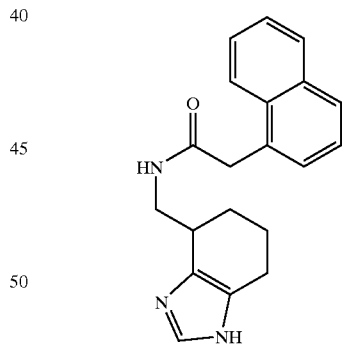

PHARMACOLOGICAL METHODS

The ability of the compounds to interact with the histamine H3 receptor can be determined by the following in vitro binding assays.

Binding assay I

Rat cerebral cortex is homogenized in ice cold K-Hepes, 5 mM $MgCl_2$ pH 7.1 buffer. After two differential centrifugations the last pellet is resuspended in fresh Hepes buffer containing 1 mg/ml bacitracin. Aliquots of the membrane suspension (400 μg/ml) are incubated for 60 min at 25° C. with 30 pM [$^{125}$i]Iodoproxifan, a known histamine H3 receptor antagonist, and the test compound at various concentrations. The incubation is stopped by dilution with ice-cold medium, followed by rapid filtration through Whatman GF/B filters pretreated for 1 hour with 0.5% polyethyleneimine . The radioactivity retained on the filters is counted using a Cobra II auto gamma counter. The radioactivity of the filters is indirectly proportional to the binding affinity of the tested compound. The results are analyzed by nonlinear regression analysis.

Binding assay II

The H3-receptor agonist ligand R-α-methyl[$^3$H]histamine (RAMHA) is incubated with isolated rat cortex cell-membranes at 25° C. for 1 hour, followed by a filtration of the incubate through Whatman GF/B filters. Radioactivity retained on the filters is measured using a beta counter.

Male Wistar rats (150–200 g) are decapitated and cerebral cortex is quickly dissected out and frozen immediately on dry ice. Tissue is kept at −80° C. until membrane preparation. During the membrane preparation the tissue is kept on ice all the time. Rat cerebral cortex is homogenized in 10 volumes (w/w) ice-cold Hepes buffer (20 mM Hepes, 5 mM $MgCl_2$ pH 7.1 (KOH)+1 mg/ml bacitracin) using an Ultra-Turrax homogenizer for 30 seconds. The homogenate is centrifuged at 140 g in 10 min. The supernatant is transferred to a new test tube and centrifuged for 30 min at 23 000 g. Pellet is resuspended in 5–10 ml Hepes buffer, homogenized and centrifuged for 10 min at 23 000 g. This short centrifugation step is repeated twice. After the last centrifugation the pellet is resuspended in 2–4 ml Hepes buffer and the protein concentration is determined. The membranes are diluted to a protein concentration of 5 mg/ml using Hepes buffer, aliquoted and stored at −80° C. until use.

50 μl test-compound, 100 μl membrane (200 μg/ml) 300 μl Hepes buffer and 50 μl R-α-methyl[2H]histamine (1 nm) are mixed in a test tube. The compounds to be bested are dissolved in DMSO and, further diluted in $H_2O$ to the desired concentrations. Radioligand and membranes are diluted in Hepes buffer+1 mg/ml bacitracin. The mixture is incubated for 60 min at 25° C. Incubation is terminated try adding 5 ml ice-cold 0.9% NaCl, followed by rapid filtration through Whatman GF/B filters pre-treated for 1 hour with 0.5% polyethyleneimine. The filters are washed with 2×5 ml ice-cold NaCl. To each filter a 3 ml scintillation cocktail is added and the radioactivity retained is measured with a Packard Tri-Garb beta counter.

$IC_{50}$ values are calculated by non-linear regression analysis of binding curves (6 points minimum) using the windows program GraphPad Prism, GraphPad software, USA.

Binding assay III

The human H3 receptor is cloned by PCR and subcloned into the pcDNA3 expression vector. Cells stably expressing the H3 receptor are generated by transfecting the H3-expression vectors into HEK 293 cells and using G418 to select for H3 clones. The human H3-HEK 293 clones are cultured in DMEM (GIBCO-BRL) with glutamax, 10% foetal calf serum, 1% penicillin/streptavidin and 1 mg/ml G 418 at 37° C. and 5% $CO_2$. Before harvesting, the confluent cells are rinsed with PBS and incubated with Versene (proteinase, GIBCO-BRL) for approximately 5 min. The cells are flushed with PBS and DMEM and the cellsuspension collected in a tube and centrifuged for 5–10 min at 1500 rpm in a Heraeus Sepalech Megafuge 1.0. The pellet is resuspended to 10–20 vol. Hepes buffer (20 mM Hepes, 5 mM $MgCl_2$, pH 7.1(KOH)) and homogenized for 10–20 seconds using an Ultra-Turrax homogenizer. The homogenate is centrifuged for 30 min at 23 000 g. The pellet is resuspended in 5–10 ml Hepes buffer, homogenized 5–10 seconds with the Ultra-Turrax and centrifuged for 10 min at 23 000 g. Following this centrifugation step, the membrane pellet is resuspended in 2–4 ml Hepes buffer, homogenized with a syringe or teflonhomogenizer, and the protein concentration determined. The membranes are diluted to a protein concentration of 1–5 mg/ml in Hepes buffer, aliquoted and kept at −80° C. until use.

Aliquots of the membrane suspension are incubated for 60 min at 25° C. with 30 pM [$^{125}$I]-Iodoproxifan, a known compound with high affinity for the H3 receptor, and the test compound at various concentrations. The incubation is stopped by dilution with ice-cold medium, followed by rapid filtration through Whatman GF/B filters pretreated for 1 hour with 0.5% polyethyleneimine. The radioactivity retained on the filters is counted using a Cobra II auto gamma counter. The radioactivity of the filters is indirectly proportional to the binding affinity of the tested compound. The results are analysed by nonlinear regression analysis.

When tested, the present compounds of the formula (I) generally show a high binding affinity to the histamine H3 receptor.

Preferably, the compounds according to the invention have an $IC_{50}$ value as determined by one or more of the assays of less than 10 μM, more preferred of less than 1 μM, and even more preferred of less than 500 nM, such as of less than 100 nM.

Functional assay I

The ability of the compounds to interact with the histamine H3 receptor as agonists, inverse agonists and/or antagonists, is determined by an in vitro functional assay utilizing membranes from HEK 293 cell expressing the human H3 receptors.

The H3 receptor is cloned by PCR and subcloned into the pcDNA3 expression vector. Cells stably, expressing the H3 receptor are generated by transfecting the H3-expression vectors into HEK 293 cells and using G418 to select for H3 clones. The human H3-HEK 293 clones are cultured in DMEM with glutamax, 10% foetal calf serum. 1% penicillin/streptavidin and 1 mg/ml G 418 at 37° and 5% $CO_2$.

The H3 receptor expressing cells are washed once with phosphate buffered saline (PBS) and harvested using versene (GIBCO-BRL). PBS is added and the cells are centrifuged for 5 min at 188 g. The cell pellet is resuspended in stimulation buffer to a concentration of 1×10$^8$ cells/ml. cAMP accumulation is measured using the Flash Plate® cAMP assay (NEN™ Life Science Products). The assay is generally performed as described by the manufacturer. Briefly, 50 pi cell suspension is added to each well of the Flashplate which also contained 25 μl 40 μM isoprenaline, to stimulate cAMP generation, and 25 μl of test compound (either agonists or inverse agonists alone, or agonist and antagonist in combination). The assay can be run in "agonist-mode" which means that the test compound is added, in (increasing concentration, on its own, to the cells, and cAMP is measured. If cAMP goes up, it is an inverse agonist; if cAMP does not change, it is a neutral antagonist, and if cAMP goes down, it is an agonist. The assay can also be run in the "antagonist-mode" which means that a test compound is added, in increasing concentrations, together with increasing concentrations of a known H3 agonist (eg RAMHA). If the compound is an antagonist, increasing concentrations of it cause a right-ward shift in the H3-agonists dose-response curves. The final volume in each well is 100 μl Test compounds are dissolved in DMSO and diluted in $H_2O$. The mixture is shaken for 5 min, and allowed to stand for 25 min at mom temperature. The reaction is stopped with 100 μl "Detection Mix" per well. The plates are then sealed with plastic, shaken for 30 min, allowed to stand overnight, and finally the radioactivity is counted in the Cobra II auto gamma topcounter. $EC_{50}$ values are calculated by non-linear regression analysis of dose response curves (6 points minimum) using GraphPad Prism. Kb values are calculated by Schild plot analysis.

The ability of the present compounds to reduce weight is determined using the (m, vivo open cage Schedule-fed rat model.

The open cage Schedule-fed rat model

Sprague-Dawley (SD) male rats of an age of about 1 1/2 to 2 months and a weight of about 250 g are habituated to the presence of food (Altromin pelleted rat chow) in their home cage only during three tours in the morning from 9 to 12 a.m. all days a week. Water is present ad libitum. As the consumption of food stabilised after 7 to 9 days, the animals are ready for use.

The animals are tested twice a week. During the test sessions, the test compound is administered intraperitoneally 30 min before the start of the sessions. One group of 9 animals is administered the test compound at a dose of 15 mg/kg and another group of 11 animals is administered the test compound at a dose of 30 mg/kg. A control group of 11 animals is administered the vehicle consisting of NaCl 0.9% and Cremophor 5%. Food and water intake are monitored at 1, 2 and 3 hours post administration.

During the test period the animals are weighed weekly and if necessary extra food is given in order to ensure that the weight gain is 3 to 5 g per week corresponding to the normal weight gain for SD male rats at this age.

Any side effects could rapidly be discovered (barrel-rolling, bushy fur etc.) since the animals are kept in transparent plastic cages to enable continuous monitoring.

What is claimed is:

1. A compound of the formula (Ih):

(Ih)

wherein q is 1, 2 or 3, Z is selected from $C_{1-6}$-alkyl, $C_{2-6}$-alkenyl, aryl, aryloxy, heteroaryl, $C_{3-10}$-cycloalkyl, $C_{3-8}$-heterocyclyl and aryl annulated with $C_{3-8}$-heterocyclyl, which are unsubstituted or substituted with one or more substituents selected from nitro, $-NR^{12}R^{13}$, $-S(=O)_2NR^{12}R^{13}$, $-C(=O)NR^{12}R^{13}$, hydroxy, halogen, cyano, trifluoromethyl, $-OCF_3$, $-OCHF_2$, $-OCH_2CHF_2$, $C_{1-6}$-alkyl, $C_{1-6}$-alkyl substituted with hydroxy, $C_{2-6}$-alkenyl, $C_{2-6}$-alkynyl, $C_{1-6}$-alkoxy, $C_{1-6}$-alkoxy substituted with hydroxy, $C_{1-6}$-alkylthio, $C_{1-6}$-alkylsulfonyl, $-C(=O)OR^{12}$, $C_{1-6}$-alkylcarbonyl, $-C(=NOR^{12})C_{1-6}$-alkyl, $C_{3-10}$-cycloalkyl, $C_{3-10}$cycloalkylcarbonyl, $-C(=NOR^{12})$ $C_{3-10}$-cycloalkyl, aryl-$C_{1-6}$-alkyl, heteroaryl—$C_{1-6}$-alkyl, arylamino, heteroarylamino, aroyl, heteroaroyl, arylsulfonyl, heteroarylsulfonyl, $-C(=NOR^{12})$aryl, $-C(=NOR^{12})$heteroaryl, arylthio, heteroarylthio and heteroaryloxy, wherein $R^{12}$ and $R^{13}$ independently are hydrogen or $C_{1-6}$-alkyl, aryl and aryloxy, which are optionally substituted with one or more substituents selected from $C_{1-6}$-alkyl, $C_{1-6}$-alkoxy, halogen, $-OCF_3$ or $-CF_3$, $C_{1-6}$-alkyl, $C_{2-6}$-alkenyl, or $C_{2-6}$-alkynyl, which are unsubstituted or substituted with one or more substituents selected from heteroaryl, aryl, aryloxy, aroyl, $C_{3-10}$-cycloalkyl, $C_{3-8}$-heterocyclyl and aryl annulated with $C_{3-8}$-heterocyclyl, which are optionally substituted with one or more substituents selected from nitro, $-NR^{12}R^{13}$, $-S(=O)_2NR^{12}R^{13}$, $-C(=O)NR^{12}R^{13}$, hydroxy, halogen, cyano, trifluoromethyl, $-OCF_3$, $-OCHF_2$, $-OCH_2CHF_2$, $C_{1-6}$-alkyl, $C_{1-6}$-alkyl substituted with hydroxy, $C_{2-6}$-alkenyl, $C_{2-6}$-alkynyl, $C_{1-6}$-alkoxy, $C_{1-6}$-alkoxy substituted with hydroxy, $C_{1-6}$-alkylthio, $C_{1-6}$-alkylsulfonyl, $-C(=O)OR^{12}$, $C_{1-6}$-alkylcarbonyl, $-C(=NOR^{12})$ $C_{1-6}$-alkyl, $C_{3-10}$-cycloalkyl, $C_{3-10}$-cycloalkylcarbonyl, $=C(=NOR^{12})C_{3-10}$cycloalkyl, aryl-$C_{1-6}$-alkyl, heteroaryl-$C_{1-6}$-alkyl, arylamino, heteroarylamino, aroyl, heteroaroyl, arylsulfonyl, heteroarylsulfonyl, $-C(=NOR^{12})$aryl, $-C(=NOR^{12})$heteroaryl, arylthio, heteroarylthio and heteroaryloxy, wherein $R^{12}$ and $R^{13}$ independently are hydrogen or $C_{1-6}$-alkyl, aryl and aryloxy, which are optionally substituted with one or more substituents selected from $C^{1-6}$-alkyl, $C^{1-6}$-alkoxy, halogen, $-OCF_3$ or $-CF_3$, and $R^1$ is hydrogen or a group which can be converted to hydrogen in vivo, $R^2$ is hydrogen, $R^3$ and $R^4$ independently are hydrogen or $C_{1-6}$-alkyl, which is unsubstituted or substituted with aryl or heteroaryl, which are unsubstituted or substituted with one or more substituents selected from nitro, $-NR^7R^8$, $-S(=O)_2NR^7R^8$, $-C(=O)NR^7R^8$, hydroxy, halogen, cyano, trifluoromethyl, $-OCF_3$, $-OCHF_2$, $-OCH_2CHF_2$, $C_{1-6}$-alkyl, $C_{2-6}$-alkenyl, $C_{2-6}$-alkynyl, $C_{1-6}$-alkoxy, $C_{1-6}$-alkylthio, $C_{1-6}$-alkylsulfonyl, $-C(=O)OR^7$, $C_{1-6}$-alkylcarbonyl, $-C(=NOR^7)C_{1-6}$-alkyl, $C_{3-10}$-cycloalkyl, $C_{3-10}$-cycloalkylcarbonyl, $-C(=NOR^7)C_{3-10}$-cycloalkyl, aryl-$C_{1-6}$-alkyl, heteroaryl—$C_{1-6}$-alkyl, arylamino, heteroarylamino, aroyl, heteroaroyl, arylsulfonyl, heteroarylsulfonyl, $-C(=NOR^7)$aryl, $-C(=NOR^7)$-heteroaryl, arylthio, heteroarylthio, aryloxy and heteroaryloxy, wherein $R^7$ and $R^8$ independently are hydrogen or $C_{1-6}$-alkyl, and $R^{11}$ is hydrogen or $C_{1-6}$alkyl, or q is 0, Z is $C_{3-8}$-cycloalkyl or $C_{3-8}$heterocyclyl, which is unsubstituted or substituted with one or more substituents selected from nitro, $-NR^{12}R^{13}$, $-S(=O)_2NR^{12}R^{13}$, $-C(=O)NR^{12}R^{13}$, hydroxy, halogen, cyano, trifluoromethyl, $-OCF_3$, $-OCHF_2$, $-OCH_2CHF_2$, $C_{1-6}$-alkyl, $C_{1-6}$-alkyl substituted with hydroxy, $C_{2-6}$-alkenyl, $C_{2-6}$-alkynyl, $C_{1-6}$-alkoxy, $C_{1-6}$alkoxy substituted with hydroxy, $C_{1-6}$-alkylthio, $C_{1-6}$-alkylsulfonyl, $-C(=O)OR^{12}$, $C_{1-6}$-alkylcarbonyl, $-C(=NOR^{12})C_{1-6}$-alkyl, $C_{3-10}$-cycloalkyl, $C_{3-10}$-cycloalkylcarbonyl, $-C(=NOR^{12})$ $C_{3-10}$cycloalkyl, aryl-$C_{1-6}$-alkyl, heteroaryl-$C_{1-6}$-alkyl, arylamino, heteroarylamino, aroyl, heteroaroyl, arylsulfonyl, heteroarylsulfonyl, $-C(=NOR^{12})$aryl, $-C(=NOR^{12})$heteroaryl, arylthio, heteroarylthio and heteroaryloxy, wherein $R^{12}$ and $R^{13}$ independently are hydrogen or $C_{1-6}$-alkyl, aryl and aryloxy, which are optionally substituted with one or more substituents selected from $C_{1-6}$-alkyl, $C_{1-6}$-alkoxy, halogen, $-OCF_3$ or $-CF_3$, and $R^1$, $R^2$, $R^3$, $R^4$ and $R^{11}$ are as defined above, or any optical or geometric isomer or tautomeric form thereof, or a mixture thereof, or a pharmaceutically acceptable salt thereof.

2. A compound according to claim 1, wherein $R^1$ is hydrogen.

3. A compound according to claim 1, wherein $R^3$ and $R^4$ are both hydrogen.

4. A compound according to claim 1, wherein q is 1,2 or 3, and Z is aryl, aryloxy, heteroaryl, $C_{3-10}$-cycloalkyl, $C_{3-8}$-heterocyclyl or aryl annulated with $C_{3-8}$-heterocyclyl, which is unsubstituted or substituted with one or more substituents as defined in claim 1, or $C_{1-6}$-alkyl or $C_{2-6}$-alkenyl, which is substituted with
aryl, aroyl, aryloxy, heteroaryl, $C_{3-10}$-cycloalkyl, $C_{3-8}$-heterocyclyl or aryl annulated with $C_{3-8}$-heterocyclyl, which is unsubstituted or substituted with one or more substituents as defined in claim 1, or q is 0, and Z is $C_{3-10}$-cycloalkyl or $C_{3-8}$-heterocyclyl, which is unsubstituted or substituted with one or more substituents as defined in claim 1.

5. A compound according to claim 4, wherein
q is 1, 2 or 3, and Z is phenyl, phenoxy, naphthyl, naphthyloxy, cyclopentyl, cyclohexyl, piperidyl, quinolinyl pyridyl, thienyl, thiazolyl, 2,3-dihydrobenzofuranyl, benzofuranyl, benzo[1,3]dioxolyl bicyclo[2,2,1]heptyl, adamantyl, benzimidazol, benzotriazolyl or benzothiophenyl, which is unsubstituted or substituted as defined in claim 1, or
$C_{1-4}$-alkyl or $C_{2-6}$-alkenyl, which is substituted with phenyl, phenoxy, naphthyl, naphthyloxy, benzoyl, cyclopentyl, cyclohexyl, piperidyl quinolinyl pyridyl, thienyl, thiazolyl, 2,3-dihydrobenzofuranyl, benzofuranyl, benzo[1,3]dioxolyl bicyclo[2,2,1]heptyl, adamantyl, benzimidazol, benzotriazolyl or benzothiophenyl, which is unsubstituted or substituted as defined in claim 1, or q is 0, and Z is cyclopentyl, cyclohexyl, piperidyl, bicyclo [2,2,1]heptyl or adamantyl which is unsubstituted or substituted as defined in claim 1.

6. A compound according to claim 5, wherein
q is 1, 2 or 3, and 2 is phenyl, phenoxy, naphthyl, naphthyloxy, cyclopentyl, cyclohexyl, piperidyl, pyridyl, thiazolyl, 2,3-dihydrobenzofuranyl, benzo[1,3]dioxolyl or bicyclo[2,2,1]heptyl, which is unsubstituted or substituted as defined in claim 1, or $C_{1-6}$-alkyl or $C_{2-6}$-alkenyl, which is substituted with
phenyl, phenoxy, naphthyl, naphthyloxy, benzoyl, cyclopentyl, cyclohexyl, piperidyl, pyridyl, thiazolyl, 2,3-dihydrobenzofuranyl, benzo[1,3]dioxolyl or bicyclo[2,2,1]heptyl, which is unsubstituted a substituted as defined in claim 1, or q a 0, and Z is cyclopentyl, cyclohexyl, piperidyl or bicyclo [2,2,1]heptyl, which is unsubstituted or substituted as defined in claim 1.

7. A compound according to claim 6, wherein
q is 1, 2 or 3, and Z is phenyl, phenoxy, naphthyl or naphthyloxy, which is unsubstituted or substituted as defined in claim 1, or $C_{1-6}$-alkyl or $C_{2-6}$-alkenyl, which is substituted with phenyl, phenoxy, naphthyl, benzoyl or naphthyloxy, which is unsubstituted or substituted as defined in claim 1.

8. A compound according to claim 7, wherein q is 1, 2 or 3, acid Z is phenyl, which is unsubstituted or substituted as defined in claim 1.

9. A compound according to claim 1, wherein q is 1, 2 or 3, and Z is aryl, aryloxy, heteroaryl, $C_{3-10}$-cycloalkyl, $C_{2-8}$-heterocyclyl or aryl annulated with $C_{3-8}$-heterocyclyl, which is unsubstituted or substituted with one or two substituents selected from $C_{1-6}$-alkylsulfonyl, hydroxy, $C_{1-8}$-alkyl, $C_{1-6}$-alkoxy, halogen, —$OCF_3$, —$CF_3$, —$N(C_{1-6}$-alkyl$)_2$, $C_{1-6}$-alkylthio, $C_{1-6}$-alkoxy substituted with hydroxy and $C_{1-6}$-alkyl substituted with hydroxy, phenyl and phenoxy, which are unsubstituted or substituted as defined in claim 1, or q is 1, and Z is $C_{3-10}$-cycloalkyl or $C_{3-8}$-heterocyclyl, which is unsubstituted or substituted with one or two substituents selected from $C_{1-6}$-alkylsulfonyl, hydroxy, $C_{1-6}$-alkyl, $C_{1-6}$-alkoxy, halogen, —$OCF_3$, —$CF_3$, —$N(C_{1-6}$-alkyl$)_2$, $C_{1-6}$-alkylthio, $C_{1-6}$-alkoxy substituted with hydroxy and $C_{1-6}$-alkyl substituted with hydroxy, phenyl and phenoxy, which are unsubstituted or substituted as defined in claim 1.

10. A compound according to claim 9, wherein q is 1, 2 or 3, and Z is aryl, aryloxy, heteroaryl, $C_{3-10}$-cycloalkyl, $C_{3-8}$-heterocyclyl or aryl annotated with $C_{3-8}$-heterocyclyl, which is unsubstituted or substituted with one or two substituents selected from $C_{3-6}$-alkyl, $C_{1-6}$-alkoxy, —$CF_3$, —$OCF_3$, phenoxy and halogen, or q is 0, and Z is $C_{3-10}$-cycloalkyl or $C_{2-8}$-heterocyclyl, which is unsubstituted or substituted with one or two substituents selected from $C_{1-6}$-alkyl, $C_{1-4}$-alkoxy, —$CF_3$, —$OCF_3$, phenoxy and halogen.

11. A method of treating disorders and diseases related to the histamine H3 receptor, comprising administering an effective amount to the compound of claim 1 to a patient in need thereof.

12. The method of claim 11, wherein the disorder is overweight or obesity.

13. The method of claim 11, wherein the disorder is one of appetite, bulimia, and binge eating, IGT, Type 2 diabetes, allergic rhinitis, ulcer, or anorexia.

* * * * *

UNITED STATES PATENT AND TRADEMARK OFFICE
CERTIFICATE OF CORRECTION

PATENT NO. : 6,756,384 B2
APPLICATION NO. : 10/201865
DATED : June 29, 2004
INVENTOR(S) : Andersen et al.

Page 1 of 1

It is certified that error appears in the above-identified patent and that said Letters Patent is hereby corrected as shown below:

Column 124, line 23, claim 1:
"$C^{1-6}$-alkyl" should read --$C_{1-6}$-alkyl--.
Column 124, line 24, claim 1:
"$C^{1-6}$-alkoxy" should read --$C_{1-6}$-alkoxy--.
Column 125, line 28, claim 5:
"$C_{1-4}$-alkyl" should read --$C_{1-6}$-alkyl--.
Column 125, line 40, claim 6:
"2 is phenyl" should read --Z is phenyl--.
Column 125, line 51, claim 6:
"q a 0" should read --q is 0--.
Column 126, line 19, claim 9:
"$C_{1-8}$-alkyl" should read --$C_{1-6}$-alkyl--.
Column 126, line 37, claim 10:
"annotated" should read --annulated--.
Column 126, line 39, claim 10:
"$C_{3-6}$-alkyl" should read --$C_{1-6}$-alkyl--.
Column 126, line 41, claim 10:
"$C_{2-8}$-heterocyclyl" should read --$C_{3-8}$-heterocyclyl--.

Signed and Sealed this

Seventh Day of August, 2007

JON W. DUDAS
*Director of the United States Patent and Trademark Office*